US012564551B2

(12) United States Patent
Herrmann et al.

(10) Patent No.: US 12,564,551 B2
(45) Date of Patent: Mar. 3, 2026

(54) COMPOSITION OR OAT EXTRACT COMPRISING AVENANTHRAMIDE AND β-GLUCAN

(71) Applicant: SYMRISE AG, Holzminden (DE)

(72) Inventors: Martina Herrmann, Hameln (DE); Holger Joppe, Dassel (DE)

(73) Assignee: SYMRISE AG, Holzminden (DE)

( * ) Notice: Subject to any disclaimer, the term of this patent is extended or adjusted under 35 U.S.C. 154(b) by 499 days.

(21) Appl. No.: 17/909,333

(22) PCT Filed: Mar. 6, 2020

(86) PCT No.: PCT/EP2020/056118
§ 371 (c)(1),
(2) Date: Sep. 2, 2022

(87) PCT Pub. No.: WO2021/175450
PCT Pub. Date: Sep. 10, 2021

(65) Prior Publication Data
US 2023/0124050 A1 Apr. 20, 2023

(51) Int. Cl.

| | |
|---|---|
| ***A61K 8/9794*** | (2017.01) |
| ***A23L 33/105*** | (2016.01) |
| ***A61K 8/42*** | (2006.01) |
| ***A61K 8/73*** | (2006.01) |
| ***A61K 31/167*** | (2006.01) |
| ***A61K 31/192*** | (2006.01) |
| ***A61K 31/716*** | (2006.01) |
| ***A61K 36/899*** | (2006.01) |
| ***A61Q 19/00*** | (2006.01) |

(52) U.S. Cl.
CPC .......... *A61K 8/9794* (2017.08); *A23L 33/105* (2016.08); *A61K 8/42* (2013.01); *A61K 8/73* (2013.01); *A61K 31/167* (2013.01); *A61K 31/192* (2013.01); *A61K 31/716* (2013.01); *A61K 36/899* (2013.01); *A61Q 19/00* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 5,169,660 | A | 12/1992 | Collins et al. | |
| 6,096,770 | A | 8/2000 | Lennox et al. | |
| 6,127,392 | A | 10/2000 | Lennox et al. | |
| 9,636,292 | B2 * | 5/2017 | Sweeney | A61K 8/66 |
| 2005/0042243 | A1 | 2/2005 | Redmond et al. | |
| 2006/0067959 | A1 * | 3/2006 | Nimni | A61K 31/375 514/474 |
| 2006/0089413 | A1 | 4/2006 | Schmaus et al. | |
| 2009/0226537 | A1 | 9/2009 | Schmaus et al. | |
| 2009/0297468 | A1 | 12/2009 | Vielhaber et al. | |
| 2010/0267662 | A1 | 10/2010 | Fielder et al. | |
| 2023/0124050 | A1 | 4/2023 | Herrmann et al. | |

FOREIGN PATENT DOCUMENTS

| | | | |
|---|---|---|---|
| CN | 108096106 | A | 6/2018 |
| EP | 1522304 | A2 | 4/2005 |
| EP | 4114349 | A1 | 1/2023 |
| JP | 2006-514931 | A | 5/2006 |
| KR | 20110032182 | A | 3/2011 |
| KR | 20180044048 | A | 5/2018 |
| WO | WO-00/67626 | A2 | 11/2000 |
| WO | WO-2004/047833 | A2 | 6/2004 |
| WO | WO-2007/062957 | A1 | 6/2007 |
| WO | WO-2021/175450 | A1 | 9/2021 |

OTHER PUBLICATIONS

F. William Collins, Oat Phenolics: Avenanthramides, Novel Substituted N-Cinnamoylanthranilate Alkaloids from Oats Groats and Hulls, *J. Agric. Food Chem.*, 37:60-66 (1989).

Gibeaut et al., "Cell Wall and Enzyme Changes during the Graviresponse of the Leaf-Sheath Pulvinus of Oat (*Avena sativa*)," *Plant Physiol.*, 94:411-16 (1990).

Daou et al., "Oat Beta-Glucan: Its Role in Health Promotion and Prevention of Diseases," *Comprehensive Reviews in Food Science and Food Safety*, 11:355-65 (2012).

Hüseyin Boz, "Phenolic Amides (Avenanthramides) in Oats—A review," *Czech J. Food Sci.*, 33(5):399-404 (2015).

Maliarova et al., "Optimization of Parameters for Extraction of Avenanthramides from Oat (*Avena sativa* L.) Grain Using Response Surface Methodology (RSM)," *J. Braz. Chem. Soc.*, 26(11):2369-78 (2015).

Ren et al., "Chemical Characterization of the Avenanthramide-Rich Extract from Oat and Its Effect on D-Galactose-Induced Oxidative Stress in Mice," *J. Agric. Food Chem.*, 59:206-11 (2011).

Bartlomeiji et al., "Bioactive compounds in cereal grains—occurrence, structure, technological significance and nutrtional benefts—a review," *Food Science and Technology International*, 18(6):559-68 (2011).

Tong et al., "Effects of Cultivar on Phenolic Content and Antioxidant Activity of Naked Oat in China," *Journal of Integrative Agriculture*, 13(8):1809-16 (2014).

Walters et al., "Phenolic acids, avenanthramides, and antioxidant activity of oats defatted with hexane or supercritical fluid," *Journal of Cereal Science*, 79:21-26 (2018).

(Continued)

*Primary Examiner* — Susan Hoffman
(74) *Attorney, Agent, or Firm* — MARSHALL, GERSTEIN & BORUN LLP

(57) ABSTRACT

The present invention relates generally to a composition or an oat extract comprising at least one avenanthramide compound or an analogue thereof and at least one β-glucan compound at predetermined ratios and having a low salt content. In addition, the present invention relates to a method for preparing such an oat extract, an oat extract obtained by said method, and the use of said composition or oat extract for the preparation of foods, food supplements, cosmetic, pharmaceutical or veterinary preparations. Finally, the present invention relates to foods, food supplements, cosmetics, pharmaceuticals or veterinary preparations comprising said composition or oat extract.

9 Claims, 3 Drawing Sheets

(56) References Cited

OTHER PUBLICATIONS

Office Action (and English translation) from JP Application No. 2022-553575 dated Sep. 29, 2023.
Office Action from Canadian Application No. 3,172,769 dated Sep. 14, 2023.

* cited by examiner

COMPOSITION OR OAT EXTRACT COMPRISING AVENANTHRAMIDE AND β-GLUCAN

CROSS-REFERENCE TO RELATED APPLICATIONS

This is a U.S. National Phase of International Application PCT/EP2020/056118, filed Mar. 6, 2020.

TECHNICAL FIELD

The present invention relates generally to a composition or an oat extract comprising at least one avenanthramide compound or an analogue thereof and at least one β-glucan compound at predetermined ratios and having a low salt content. In addition, the present invention relates to a method for preparing such an oat extract, an oat extract obtained by said method, and the use of said composition or oat extract for the preparation of foods, food supplements, cosmetic, pharmaceutical or veterinary preparations. Finally, the present invention relates to foods, food supplements, cosmetic, pharmaceutical or veterinary preparations comprising said composition or oat extract.

BACKGROUND ART

Poaceae, also known as Gramineae, is a large and nearly ubiquitous family of monocotyledonous flowering plants known as grasses. Grasses are an economically important family of plants. They have been grown as feed for domesticated animals for up to 6,000 years, and the grains of grasses such as wheat, rice, maize (corn), barley, sorghum, millet and oat have been and still are the most important human food crops.

Cereal grains are an excellent source of numerous unique substances among biologically active compounds such as dietary fibre (arabinoxylans, β-glucans, cellulose, lignin and lignans), sterols, tocopherols, tocotrienols, phenolic compounds, vitamins and microelements.

Phenolic compounds have antioxidant properties and can protect against degenerative diseases (such as heart disease and cancer) in which reactive oxygen species (i.e. superoxide anions, hydroxyl radicals and peroxy radicals) are involved. A general definition of a phenolic compound is any compound containing a benzene ring with one or more hydroxyl groups. Phenolic acids, flavonoids, condensed tannins, coumarins and alkylresorcinols are examples. In cereal grains, these compounds are located mainly in the pericarp, and they can be concentrated by decorticating the grain to produce bran. Phenolic compounds can be grouped into flavonoids (sub-classified as flavonols, flavones, isoflavones, anthocyanins, flavanols, flavanones, etc.) and non-flavonoids. Phenolic compounds can exist as free phenols or in glycosidic form. They tend to be relatively polar and typically dissolve in pure or aqueous alcohols such as ethanol and methanol or aqueous acetone. Many phenolic compounds in cereals (such as phenolic acids and flavonoids) are also reported in fruits and vegetables, but some phenols are unique to one plant species, such as for example oat avenanthramides [Dykes et al., Cereal Foods World 2007, 105-111]. Among cereals, only oats contain avenanthramides. These compounds are antipathogens, which are produced by the plant in response to the exposure to pathogens such as fungus.

Beta-glucans are among the principal fractions of cereal grain dietary fibre. They occur in the walls of aleurone layer cells and bran. Average total β-glucan content in grains of barley, oat, rye and wheat is 4.0-7.0%, 2.2-7.8%, 1.2-2.9% and 0.4-1.4%, respectively. (1→3), (1→4)-β-D-glucans, which are commonly referred to as β-glucans, consist of D-glucopyranose residues linked by β-(1→4)-glycosidic bonds which separate every two, three or four D-glucopyranose units by one β-(1→3)-glycosidic linkage. The structure of β-glucans dictates their physicochemical (solubility in water, viscosity and gel formation) and functional characteristics. Beta-glucans have numerous benefits, such as reducing the occurrence of coronary heart disease, decreasing the level of LDL cholesterol and lipids in blood serum, reducing blood pressure, improving sensitivity to insulin and enabling the control of blood glucose levels, as well as antioxidant and anti-inflammatory activity [Siurek et al., Food Science and Technology International 2012, 18(6), 559-568].

Oats exist in two main species, *Avena sativa* L. and *Avena nuda* L. (synonyms include *Avena sativa* subsp. *nuda* (L.) after Gillet & Magne, and *Avena sativa* var. *nuda* (L.) after Körn). *A. sativa*, also known as common or husked oat, is primarily grown in cool temperate climates, especially in the cool and moist regions of Northern Europe and North America. *A. nuda* is known as naked or huskless oat because the husk is removed when the crop is harvested, and it has a free threshing character similar to wheat. Husked oats represent the majority of global oat production, except in China, where naked oat is the most common type.

Avenanthramides (in the following abbreviated as Avns or Avn for a single avenanthramide compound), phenolic amides containing anthranilic acid and hydroxycinnamic acid moieties, are a group of naturally occurring phenolic amides in both *A. sativa* and *A. nuda* oats (see Table 1). Oats contain approximately 40 different types of Avns, which are present in both oat grains and leaves. The most abundant are Avn A (N-(4'-hydroxycinnamoyl)-5-hydroxyanthranilic acid), Avn B (N-(4'-hydroxy-3'-methoxycinnamoyl)-5-hydroxyanthranilic acid), and Avn C (N-(3',4'-dihydroxycinnamoyl)-5-hydroxyanthranilic acid), see FIG. 1 and Table 1. They are constitutively expressed in the kernels, appearing in almost all milling fractions, but occur at their highest concentrations in the bran and outer layers of the kernel [Boz H., Czech Journal of Food Sciences 2015, 33(5): 399-404]. The total content of avenanthramides (Avns) in oat grain has been found to be about 2 to 700 mg/kg (0.0002 to 0.07%), depending on the cultivar and agronomic treatment [Maliarova M. et al., Journal of the Brazilian Chemical Society 2015, 26(11), 2369-2378].

A number of studies have demonstrated that Avns have strong antioxidant activity both in vitro and in vivo, as well as anti-inflammatory, anti-irritant, anti-atherogenic and anti-proliferative activities which may prevent or limit cellular oxidative dysfunctions and the development of oxidative stress-related diseases, such as neurodegenerative and cardiovascular diseases, and provide additional protection against skin irritation, aging, CHD and cancer [Perrelli A. et al., Oxidative Medicine and Cellular Longevity 2018, DOI: 10.1155/2018/6015351].

The antioxidant activity of Avns has been found to be 10 to 30 times higher than those of the typical cereal components ferulic acid, gentisic acid, phydroxybenzoic acid, protocagtechuic acid, syringic acid, vanillic acid and vanillin. The Avns differ in the antioxidant activity, Avn C having the highest activity, followed by Avn B and Avn A. Avns enriched oat extracts inhibit LDL oxidation in vitro. Both, animal studies and human clinical trials confirmed that oats antioxidants have the potential of reducing cardiovascular risks by lowering serum cholesterol, inhibiting LDL cholesterol oxidation and peroxidation. Another study has indicated that the consumption of oats and oats bran may reduce the risk of colon cancer not only because of their high fiber contents but also due to Avns. Furthermore, Avns enriched oat extracts have been shown to inhibit atherosclerosis and activation of the NF-kB transcription factor, which is the regulator of infection and inflammation [Hüiseyin Boz, Phenolic Amides (Avenanthramides) in Oats—A Review, Czech J. Food Sci., 33, 2015 (5), 399-404].

The extraction of Avns from oats was carried out using various solvent compositions such as pure or diluted ethanol and methanol. Extraction procedures were achieved over different times at room temperature or under controlled heating, such as naked oats, 50% aqueous ethanol [Tong L et al., Journal of Integrative Agriculture 2014, 13, 1809].

Maliarova, M. et al., Journal of the Brazilian Chemical Society 2015, 26(11), 2369-2378 compared the efficiency of methanol, ethanol and isopropanol on the extraction of Avns from naked oat bran. The optimum conditions for the highest yield of Avns were a methanol concentration of 70%, an extraction temperature of 55° C. and an extraction time of 165 minutes.

In oats, a principal component of the soluble fibres comprises oat β-glucans. It is located in the endosperm cell walls, which are thickest adjacent to the aleurone layer, in the sub-aleurone layer. The process of isolating and purifying oat β-glucan is extremely difficult. The extraction methodologies for oat β-glucans are based on solubility in hot water and alkaline solutions. Purification can be achieved for example by separating the co-extracted proteins by isoelectric precipitation, and precipitating the β-glucan using ammonium sulphate, 2-propanol or ethanol [Daou C. and Zhang H., Comprehensive Reviews in Food Science and Food Safety 2012, 11, 355-365].

Cereal phenolic compounds and β-glucan compounds have potent beneficial biological activities, making them valuable and highly interesting natural active ingredients for cosmetic, nutritional and health use for topical and/or oral applications for humans and animals. However, a problem of the hitherto described extraction processes aimed at preparing extracts rich in phenolic compounds (such as Avns) or β-glucan compounds is that only enrichment of one of the two substance classes can be achieved. Due to their different solubility properties and consequent extractability, they are extractable by different solvents and thus normally occur in different extracts or extract fractions, i.e. β-glucans in water extracts and phenolic compounds in pure or aqueous alcohol (such as ethanol and methanol) or aqueous acetone extracts. Furthermore, they are present in very different concentration ranges in the oat grains, i.e. average total content of Avns about 0.0002 to 0.07% and average total content of β-glucans about 2.2 to 7.8%, respectively.

Since both substance classes exhibit highly interesting biological benefits, such as antioxidant and anti-inflammatory activities, a more potent and pronounced overall activity of a cereal extract can be expected from an extract or extract fraction containing both types of compounds at the same time.

EP 1 185 241 A2 and EP 1 522 304 A2 describe the preparation of an Avn-enriched oat extract with 1 to 1500 parts per million (ppm) of Avns, obtained by extracting oatmeal with 50% aqueous ethanol at 40° C. for 30 minutes, clarifying the extract by adjusting the pH to 2.5 (Example 1) or 3.5 (Example 2) using 1N hydrochloric acid and adding ethanol, followed by membrane filtration through a membrane of $<10^4$ molecular weight cut-off (MWCO, Example 1) or 5000 MWCO (Example 2). The Avn-enriched extract obtained contains less than 0.01 wt % of β-glucan. Oat β-glucans having molecular weights of 35 to 3100 kDa [Siurek et al., Food Science and Technology International 2012, 18(6), 559-568] are thus removed by membrane filtration with the described cut-offs.

Ren et al., Journal of Agricultural and Food Chemistry 2011, 59, 206-211 describe the preparation of an Avn-enriched extract (ARE) from naked oats provided by the Chinese Academy of Agricultural Sciences (Beijing, China). The dry and cleaned oats were processed in a mill to obtain the oat bran fraction. The oat bran sample was extracted with ethanol/water/acetic acid (80:20:0.1 v/v/v) in a solid-liquid ratio of 1:8 for 2 hours at 40° C. and then centrifuged at 1250 g for 10 minutes. The supernatant was filtered, and the solid residues were further extracted twice at 40° C. using the same solvent. All of the three extracted supernatants were pooled, concentrated and then loaded onto an AB-8 resin. The AB-8 resin was washed using 0.1% acetic acid, and the absorbed Avns were subsequently eluted off the column using 95% ethanol. The ethanol fraction was sprayed, and the resultant ARE powder was analysed by HPLC using standards of analytical or chromatographic grade purity. The three major Avns, namely Avn C (=Bc), Avn A (=Bp), and Avn B (=Bf), accounted for 6.07%, 4.37% and 5.36%, respectively. As β-glucans are extractable by water or alkaline aqueous solution, the Avn-enriched extract (ARE) obtained cannot be expected to simultaneously contain a considerable content of β-glucans.

SUMMARY OF THE INVENTION

The primary aim of the present invention is therefore to provide a new composition or an oat extract comprising Avns and β-glucans with improved beneficial biological activities and properties due to the presence of both substance classes and to provide a new process which allows oat Avns and β-glucans to be enriched at the same time, thereby providing an extract fraction with improved beneficial biological activities and properties due to the presence of both substance classes in one extract fraction. Ideally, the extract fraction obtained would contain both substance classes at about equal concentration ranges. The extract fraction obtained should also be provided in a stable, easily storable liquid or solid form which is easy to use and dose, by using cosmetically or pharmaceutically accepted liquid or solid carriers or solvents and carriers compatible with use in food or food supplements.

It was surprisingly discovered that oat Avns and β-glucans enriched in this way can be obtained by a specific extraction process followed by an adsorption-desorption step using a suitable adsorber resin.

In a first aspect, the present invention relates to a composition or an oat extract comprising or consisting of at least one avenanthramide or an analogue thereof, at least one β-glucan and salts, wherein:

the weight ratio of the at least one avenanthramide or an analogue thereof or the total avenanthramides or analogues thereof to the at least one β-glucan or to the total β-glucans is in a range of 1:4 to 4:1, in particular 1:3 to 3:1; and the content of salts is ≤1.0 wt %, in particular ≤0.5 wt %; based on the dry weight of the composition or the dry weight of the oat extract.

In a second aspect, the present invention relates to a method for preparing an oat extract, comprising the steps:

(1) providing an oat source;
(2) extracting the oat source using at least one extracting solvent (extractant) at a temperature of 30 to 80° C., to obtain an extract mixture or suspension;
(3) removing the extracted insoluble oat source from the extract mixture or suspension, to obtain an extract solution;
(4) removing the organic extracting solvent from the extract solution, to obtain an aqueous extract solution
(5) providing and conditioning a sorbent and providing the sorbent in an adsorption apparatus;
(6) passing the aqueous extract solution through the sorbent in the adsorption apparatus, to adsorb the ingredients of the aqueous extract solution;
(7) eluting the adsorbed ingredients of the aqueous extract solution from the sorbent using at least one eluent solvent, to obtain an eluate; and
(8) optionally removing the eluent solvent from the eluate, to obtain an oat extract fraction.

In a third aspect, the present invention relates to an oat extract obtainable using the method according to the present invention.

In a fourth aspect, the present invention relates to the use of the composition or oat extract according to the present invention as a dermatological cosmetic for skin care, scalp care, hair care, nail care or in the prevention and/or treatment of skin conditions, intolerant and sensitive skin, skin irritation, skin reddening, wheals, pruritus (itching), skin aging, wrinkle formation, loss of skin volume, loss of skin elasticity, pigment spots, pigment abnormalities, or dry skin, i.e. for moisturising the skin.

In a fifth aspect, the present invention relates to the composition or oat extract according to the present invention for use as a medicament, in particular for use in the prevention and/or treatment of dermatological or keratological diseases, in particular of dermatological or keratological diseases having a barrier related, inflammatory, immunoallergic, atherogenic, xerotic or hyperproliferative component or in the prevention and/or treatment of dermatological diseases associated with increased ROS production or in the prevention and/or treatment of cardiovascular diseases, allergic reactions, coronary heart disease, for decreasing the level of LDL cholesterol and lipids in blood serum, for reducing blood pressure, for improving sensitivity to insulin and for enabling the control of blood glucose levels.

In a sixth aspect, the present invention relates to the use of the composition or oat extract according to the present invention for preparing foods, food supplements, cosmetic, pharmaceutical or veterinary preparations.

Finally, the present invention relates to foods, food supplements, cosmetic, pharmaceutical or veterinary preparations comprising the composition or oat extract according to the present invention.

Figure 1:
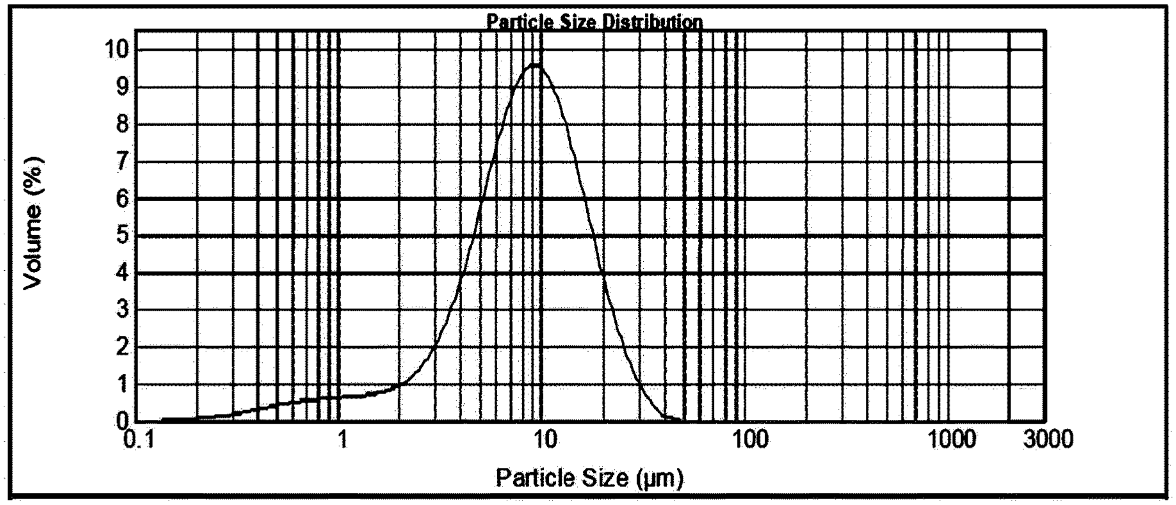
FIG. 1 is a diagram showing the particle size distribution of a spray-dried oat extraction fraction in combination with maltodextrin DE 17-20.

The invention is specified in the appended claims. The invention itself, and its preferred variants, other objects and advantages, are however also apparent from the following detailed description in conjunction with the accompanying examples and figures.

DETAILED DESCRIPTION OF THE INVENTION

In a first aspect, the present invention relates to a composition or oat extract comprising or consisting of at least one avenanthramide or an analogue thereof, at least one β-glucan and salts, wherein:

the weight ratio of the at least one avenanthramide or an analogue thereof or of the total avenanthramides or analogues thereof to the at least one β-glucan or to the total β-glucans is in a range of 1:4 to 4:1, in particular 1:3 to 3:1; and the content of salts is ≤1 wt %, in particular ≤0.5 wt %; based on the dry weight of the composition or the dry weight of the oat extract.

The composition or oat extract according to the present invention comprises or consists of at least one avenanthramide or an analogue thereof and at least one β-glucan as its main ingredients.

As used in this document, the phrase "at least one of" means that the composition or the oat extract can comprise for example either one avenanthramide or more than one avenanthramide or can comprise for example either one β-glucan or more than one β-glucan. Additionally, the phrase "at least one of", when applied to a list, means any combination of the items specified in the list.

The composition according to the first aspect of the present invention is prepared by combining the ingredients specified, as described in further detail below.

The extract according to the first aspect of the present invention is prepared from oats. The two main species of oats are *Avena sativa* L. and *Avena nuda* L. (synonyms include *Avena sativa* subsp. *nuda* (L.) after Gillet & Magne, and *Avena sativa* var. *nuda* (L.) after Körn). *A. sativa* is also known as common or husked oat. *A. nuda* is known as naked or huskless oat because the husk is removed when the crop is harvested. Oats can be processed and separated into constituent fractions including oat grains, husks and trichomes. In a preferred variant, the starting material for the oat extract is milled or non-milled grains of the species *Avena sativa* or *Avena nuda* or oat straw.

Within the context of the present invention, the term "oat extract" is generally meant to encompass a compound or mixture of compounds obtained from oats. The extract can be obtained by extraction from any oat species, fresh or dried, or parts thereof, such as grains, husks, trichomes or oat straw. Altering the composition of the extracting solvent can change the extract composition, thereby enhancing or reducing its biological activity. Work by Collins, resulting in U.S. Pat. No. 5,169,660, was able to show for the first time that avenanthramides occur naturally and can be extracted from oat grains.

Within the context of the present invention, the term "avenanthramide(s)" (anthranilic acid amides) is understood to mean a member of a group of phenolic alkaloids found mainly in oats (*Avena sativa*) but also present in white cabbage butterfly eggs (*Pieris brassicae* and *P. rapae*) and in fungus-infected carnations (*Dianthus caryophyllus*).

The avenanthramides in the composition of the present invention can be isolated and purified from natural sources such as grains, wherein they appear to be most concentrated in the peripheral regions or husks or straw. More than 50 distinct avenanthramides have been isolated from oat grains [Collins, Journal of Agricultural and Food Chemistry, 37 (1989), 60-66].

Avns can be represented by the following general Formula 1:

Formula 1

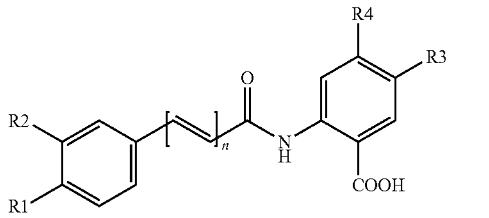

The following Table 1 shows examples of naturally occurring isolated and/or synthesised Avns based on general Formula 1.

TABLE 1

| Avenanthramide *) | CAS number | n | R1 | R2 | R3 | R4 |
|---|---|---|---|---|---|---|
| A | 108605-70-5 | 1 | OH | H | OH | H |
| B | 108605-69-2 | 1 | OH | OMe | OH | H |
| C | 116764-15-9 | 1 | OH | OH | OH | H |
| D | 115610-36-1 | 1 | OH | H | H | H |
| E | 93755-77-2 | 1 | OH | OMe | H | H |
| F | 116764-16-0 | 1 | OH | OH | H | H |
| G | 116764-17-1 | 1 | OH | H | H | OH |
| H | 116764-18-2 | 1 | OH | OMe | H | OH |
| K | 116764-19-3 | 1 | OH | OH | H | OH |
| X | 1158480-77-3 | 1 | OH | H | OH | OMe |
| Y (2 **) | 154992-25-3 | 1 | OH | OMe | OH | OMe |
| Z | 1158480-80-8 | 1 | OH | OH | OH | OMe |
| AA | 157799-28-5 | 1 | OH | H | OH | OH |
| BB | 2304718-64-5 | 1 | OH | OMe | OH | OH |
| CC | 1819995-77-1 | 1 | OH | OH | OH | OH |
| O(L **) | 172549-38-1 | 2 | OH | H | OH | H |
| P | 1358438-37-5 | 2 | OH | OMe | OH | H |
| Q | 2227208-43-5 | 2 | OH | OH | OH | H |
| L | 2301866-39-5 | 2 | OH | H | H | H |
| M | 101618-11-5 | 2 | OH | OMe | H | H |
| N | 101618-21-7 | 2 | OH | OH | H | H |
| R | 1191042-39-3 | 2 | OH | H | H | OH |
| S | 2301866-43-1 | 2 | OH | OMe | H | OH |
| T | 2301864-63-9 | 2 | OH | OH | H | OH |
| U | 2301864-86-6 | 2 | OH | H | OH | OMe |
| V | 2304718-63-4 | 2 | OH | OMe | OH | OMe |
| W | 2304718-62-3 | 2 | OH | OH | OH | OMe |
| OO | 2301866-28-2 | 2 | OH | H | OH | OH |
| PP | 2301864-57-1 | 2 | OH | OMe | OH | OH |
| QQ | 2301864-89-9 | 2 | OH | OH | OH | OH |

*) Abbreviations Collins [de Bruijn et al., Food Chemistry (2018), doi: https://doi.org/10.1016/j.foodchem.2018.11.013, supplementary information Table S1]
**) More commonly used, non-Collins abbreviations The most abundant avenanthramides in oats are: avenanthramide A (also called 2p, AF-1 or Bp), avenanthramide B (also called 2f, AF-2 or Bf), avenanthramide C (also called 2c, AF-6 or Bc), avenanthramide L (non-Collins abbreviation; CAS number 172549-38-1) (also called avenanthramide O (Collins abbreviation) or 2pd), avenanthramide P (also called 2fd) and avenanthramide Q (also called 2 cd). A number of studies have demonstrated that these natural products have anti-inflammatory, anti-oxidant, anti-itch, anti-irritant and anti-atherogenic activities.

The naturally occurring avenanthramide compounds isolated from natural sources can alternatively also be produced by organic synthesis. Methods of synthesis known in the art are illustrated for example in U.S. Pat. Nos. 6,096,770 and 6,127,392, Japanese Patent No. J60019 754 A and Hungarian Patent No. HU 200 996 B.

Said synthetic prepared avenanthramide substances are identical to the corresponding naturally occurring avenanthramide compounds as extracted from oats.

The non-naturally occurring avenanthramides analogues in the composition of the present invention which are in accordance with the following Formula 2 and endowed with important biological properties have been artificially produced by organic synthesis methodologies, such as for example those given in WO 2004/047833 A1 or WO 2007/062957 A1:

Formula 2

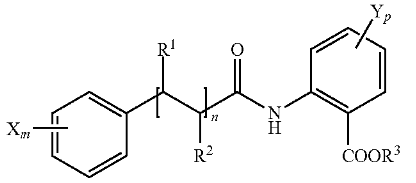

where m=0, 1, 2 or 3, p=0, 1 or 2, and n=0, 1 or 2, with the proviso that if n=1 or 2, then p+m>0, and if n=1 or 2, then $R^1$ and $R^2$, in respective pairs, respectively denote H or together denote another chemical bond (as for example in cinnamic acid derivatives), and if m=1, 2 or 3, then each X independently denotes OH, Oalkyl or Oacyl, and if p=1 or 2, then each Y independently denotes OH, Oalkyl or Oacyl, and if p+m>0, then at least one of X and Y is selected from the group consisting of OH and Oacyl, and where $R^3$ is —H or an alkyl (in particular —$CH_3$, or other straight-chain or branched alkyl chains with 2 to 30 C atoms; in this context, $R^3$ is also —H for the corresponding pharmaceutically acceptable salts).

Particularly preferred compounds of Formula 2 according to the invention are those in which:

n=1 or 2 and p+m>0; and/or p+m>0 and X or Y at least one of X and Y is selected from the group consisting of OH and Oalkyl.

Particularly preferably, a compound of Formula 2 is used in which n=1 and p+m>2, with the proviso that at least two of X and Y are together selected from the group comprising OH and Oalkyl.

It is also preferable to use a compound of Formula 2 in which n=1 and m=1, 2 or 3, with the proviso that at least one X is selected from the group comprising OH and Oalkyl, and/or P=1 or 2, with the proviso that at least one Y is selected from the group comprising OH and Oalkyl.

If n has the value 1, then $R^1$ and $R^2$ are each preferably H, although it is also possible for $R^1$ and $R^2$ together to be another chemical bond.

With regard to the definition of Formula 2 and the specific avenanthramide compounds disclosed in WO 2004/047833 A1 or WO 2007/062957 A1, the corresponding disclosure in said documents is hereby incorporated by reference.

The avenanthramide analogue compound of Formula 2 is preferably selected from the group consisting of:
2
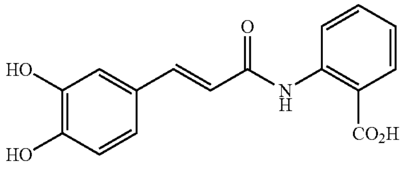
3
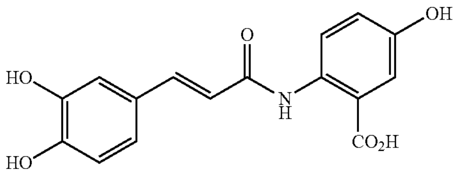
4
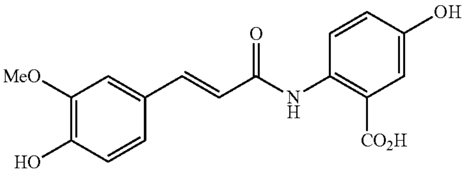
5
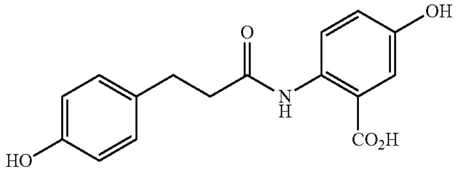
6
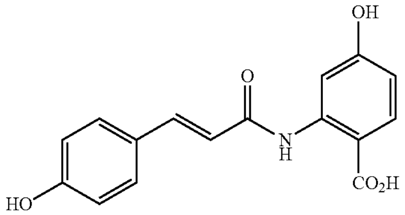
7
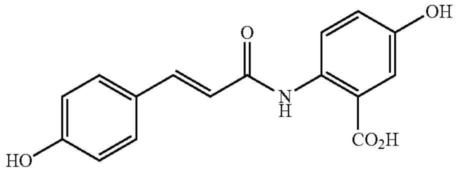
8
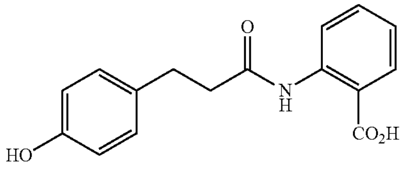
9
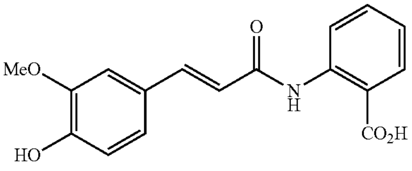
-continued
10
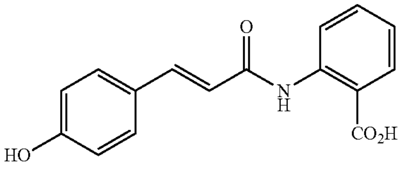
11
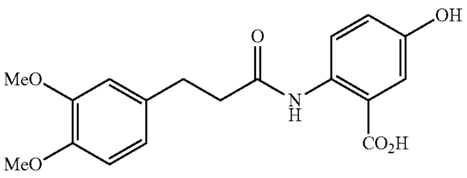
12
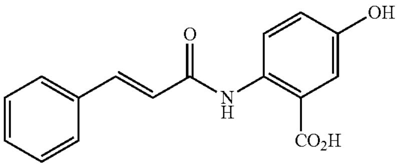
13
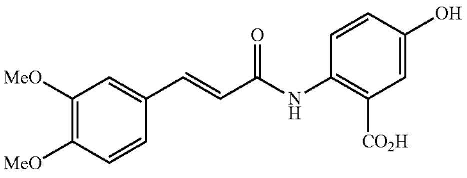
30
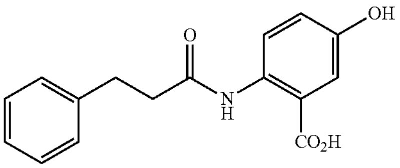
31
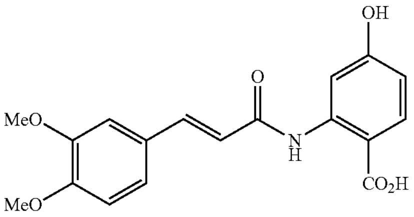
32
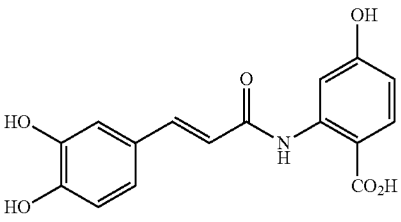
33
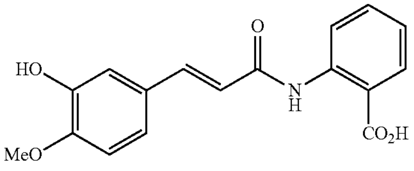

-continued
36
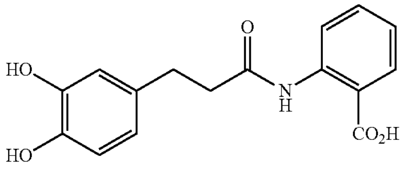
37
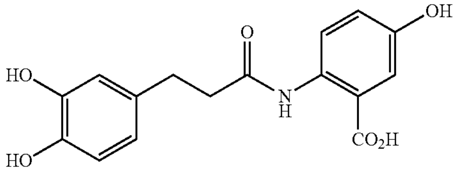
38
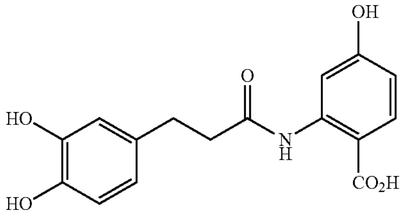
39
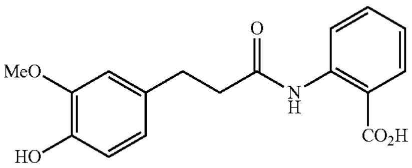
40
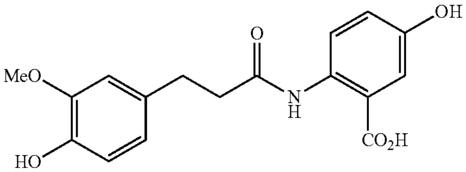
41
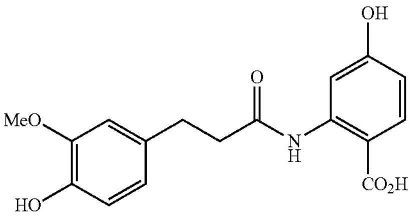
42
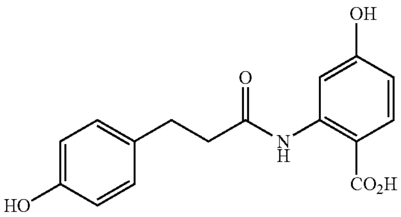
43
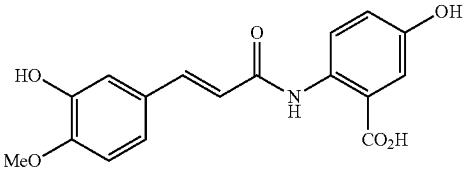
-continued
44
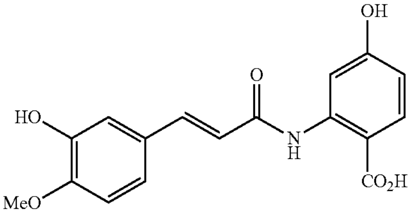
45
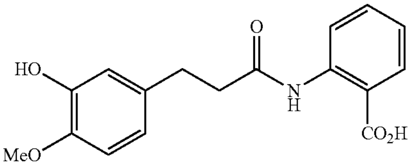
46
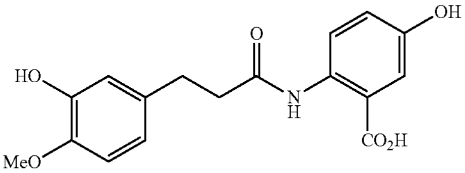
47
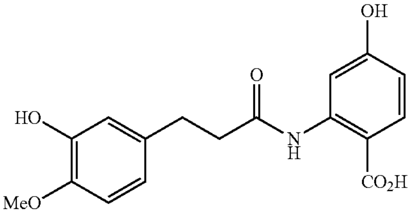
48
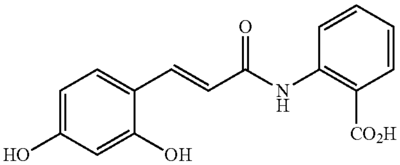
49
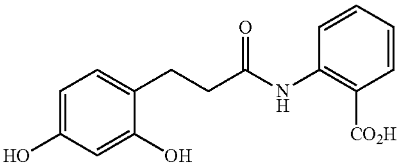
50
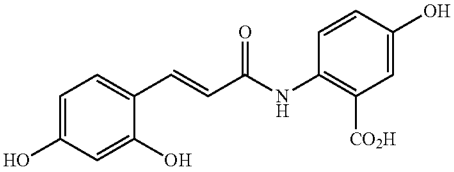
51
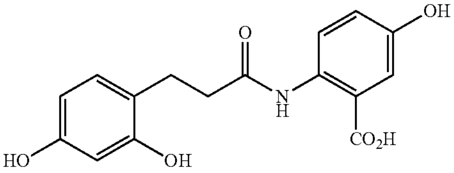

-continued
52
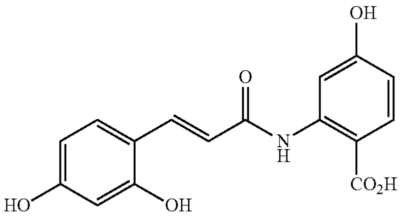
53
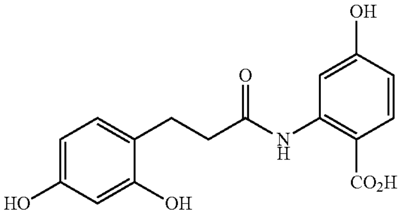
54
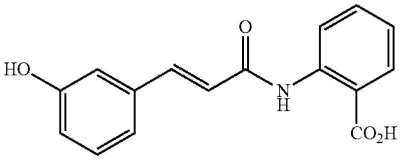
55
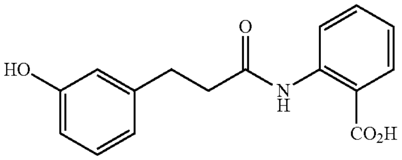
56
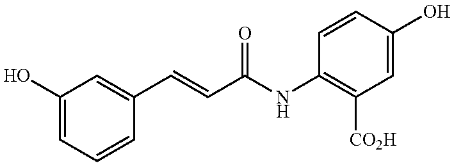
57
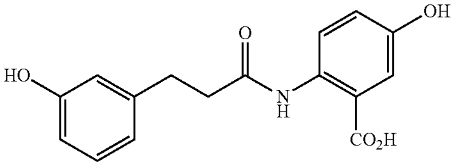
58
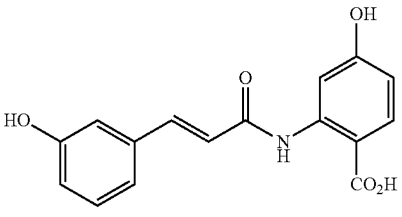
59
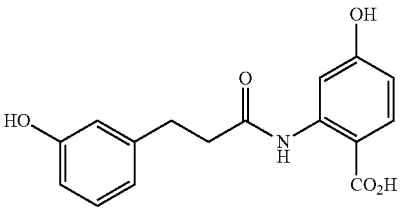
-continued
60
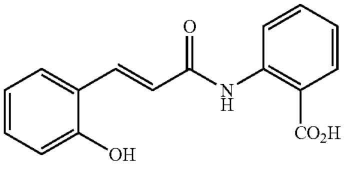
61
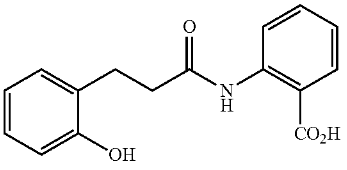
62
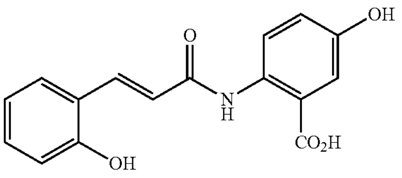
63
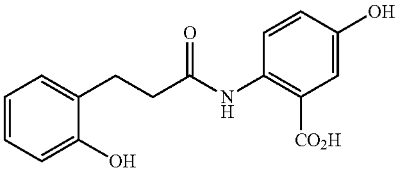
64
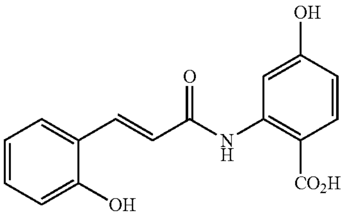
65
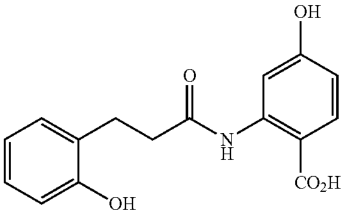
The above illustrations relate essentially to compounds of Formula 2 in which n=1.
However, the use of compounds of Formula 2 in which n=0 is also frequently preferred, in which case it preferably holds that m+p=0, or m+p>1 or 2, with the proviso that at least two of the substituents X and Y are selected from the group comprising OH and Oalkyl.

It is particularly preferable to use compounds of Formula 2 (where n=0) selected from the group comprising:
20
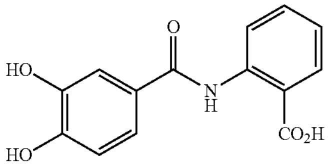
21
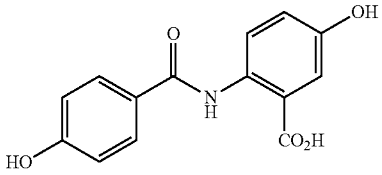
22
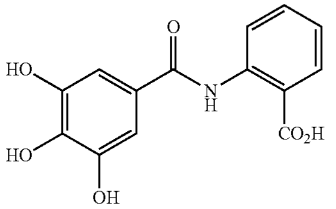
23
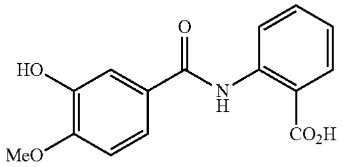
24
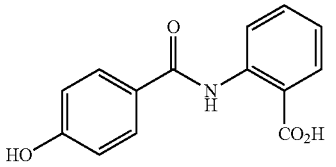
25
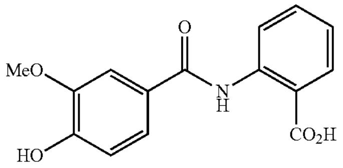
26
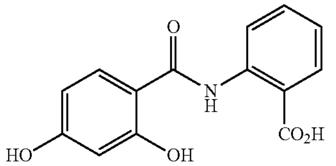
27
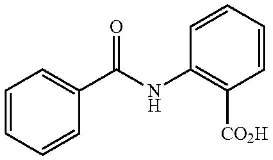
-continued
28
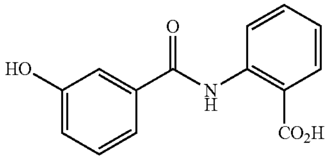
29
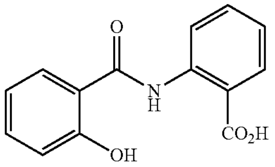
34
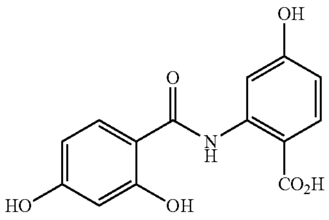
35
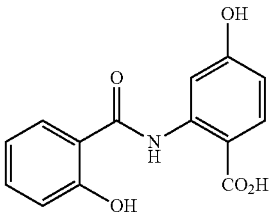
66
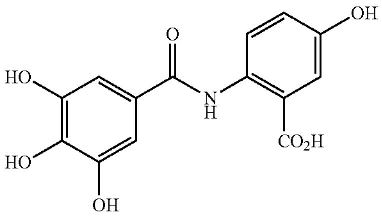
67
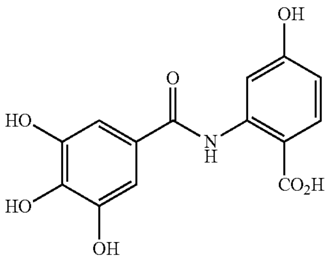
68
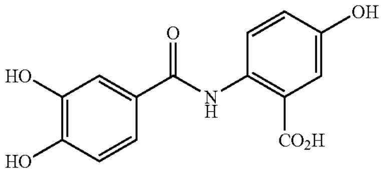

-continued

69

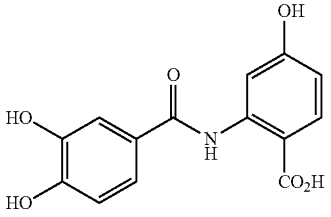

70

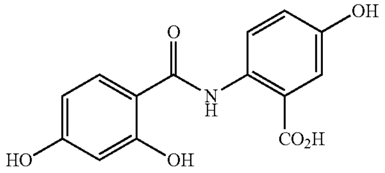

71

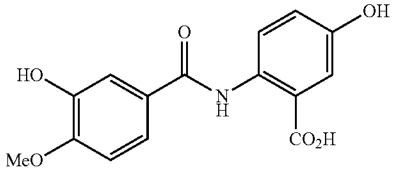

72

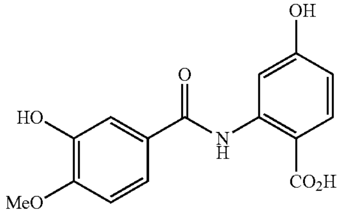

73

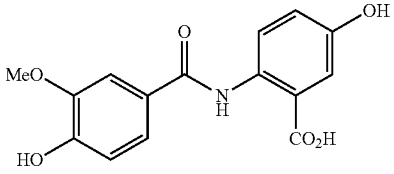

74

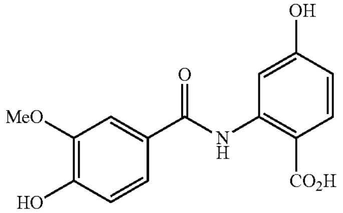

75

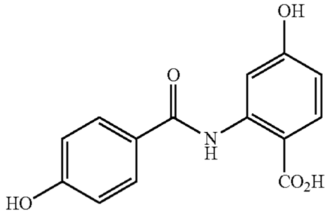

76

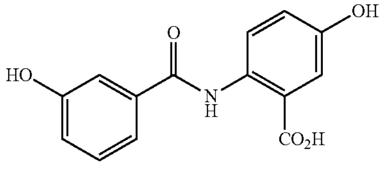

-continued

77

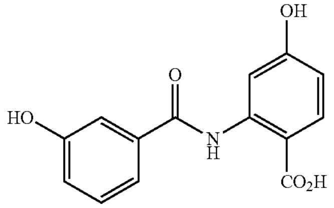

78

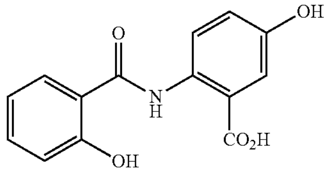

79

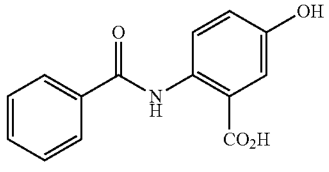

80

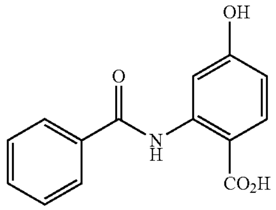

In the compounds described as particularly preferred and indicated by their structural formulae, $R^3$ is always H.

Instead of these preferred compounds, it is also preferable in each case to use the corresponding compounds in which $R^3$ is $CH_3$ or a linear or branched alkyl having 2 to 30 C atoms.

From the above avenanthramide analogue compounds No. 8 (dihydroavenanthramide D) and No. 27 are particularly preferred.

Besides the above natural occurring avenanthramides and non-natural occurring avenanthramides analogues, novel avenanthramide analogues have been produced in recombinant yeast, including N-(4'-hydroxycinnamoyl)-3-hydroxyanthranilic acid (YAvn I) and N-(3'-4'-dihydroxycinnamoyl)-3-hydroxyanthranilic acid (YAvn II), which were generated by engineering a *Saccharomyces cerevisiae* strain with two plant genes (4cl-2 from tobacco and hct from globe artichoke) encoding key proteins involved in the biosynthesis of phenolic esters. Remarkably, YAvn I and YAvn II share structural similarities with Avn A and Avn C, respectively.

In the context of the present invention naturally occurring avenanthramides obtained from naturally sources or naturally occurring avenanthramides produced synthetically are preferred and are used likewise.

The term "avenanthramide or an analogue thereof" is intended to also include their various isomers that exist, notably the naturally occurring trans-isomers as well as the cis-isomers, such as avenanthramides with cis-isomerized double bond (Formula 1 or 2 with n=1) or 1 or 2 cis-isomerized double bonds (Formula 1 or 2 with n=2) induced e.g. by photoisomerization due to light exposure.

In particular, within the context of the present invention, the avenanthramide is any one of the avenanthramide compounds represented by the general Formula 1 and defined in Table 1 or any isomer thereof or the avenanthramide analogue is any one of the avenanthramide analogue compounds represented by the general Formula 2 and its definition as described above or any isomer thereof.

In a preferred variant of the present invention according to the first aspect, the composition comprises at least one avenanthramide selected from the group consisting of avenanthramides A, B, C, G, H, K, L and R.

In another variant, the composition of the present invention comprises a mixture of two, three, four or even more different avenanthramides selected from the group consisting of avenanthramides A, B, C, G, H, K, L (non-Collins abbreviations; CAS number 172549-38-1) (also called avenanthramide O (Collins abbreviation) or 2pd) and R. The mixtures or combinations of avenanthramides can thus include any one of the following combinations of avenanthramides: A/B; A/C; A/G; A/H; A/K; A/L; A/R; B/C; B/G; B/H; B/K; B/L; B/R; C/G; C/H; C/K; C/L; C/R; G/H; G/K; G/L; G/R; H/K; H/L; H/R; K/L; K/R; L/R; A/B/C; A/B/G; A/B/H; A/B/K; A/B/L; A/B/R; A/C/G; A/C/H; A/C/K; A/C/L; A/C/R; A/G/H; A/G/K; A/G/L; A/G/R; A/H/K; A/H/L; A/H/R; A/K/L; A/K/R; A/L/R; B/C/G; B/C/H; B/C/K, B/C/L; B/C/R; C/G/H; C/G/K, C/G/L; C/G/R, G/H/K; G/H/L; G/H/R; H/K/L, H/K/R; K/L/R; A/B/C/G; A/B/C/H; A/B/C/K; A/B/C/L; A/B/C/R; A/C/G/H; A/C/G/K; A/C/G/L; A/C/G/R; A/G/H/K; A/G/H/L; A/G/H/R; A/H/K/L; A/H/K/R; A/K/L/R; B/C/G/H; B/C/G/K; B/C/G/L; B/C/G/R; C/G/H/K; C/G/H/L; C/G/H/R; G/H/K/L; G/H/K/R and H/K/L/R.

The most preferred mixtures of avenanthramides are however A/B, A/C, B/C and A/B/C.

In addition to the above avenanthramide compounds or avenanthramide combinations, the composition can further comprise one or more avenanthramide(s) other than the avenanthramides A, B, C, G, H, K, L (non-Collins abbreviations; CAS number 172549-38-1) (also called avenanthramide O (Collins abbreviation) or 2pd) and R, such as avenanthramides D, E, F U, X, Y (also termed 2), AA, CC or OO or any of the remaining avenanthramide compounds specified in Table 1.

The oat extract according to the first aspect of the present invention, obtained by the method described in detail below, comprises at least one avenanthramide selected from the group consisting of avenanthramides A, B, C, G, H, K, L (non-Collins abbreviations; CAS number 172549-38-1) (also called O (Collins abbreviation) or 2pd) and R.

In another variant, the oat extract comprises a mixture of two, three, four or even more different avenanthramides selected from the group consisting of avenanthramides A, B, C, F, G, H, L (non-Collins abbreviations; CAS number 172549-38-1) (also called O (Collins abbreviation) or 2pd) and R. The mixtures or combinations of avenanthramides can thus include any of the following combinations of avenanthramides: A/B; A/C; A/G; A/H; A/K; A/L; A/R; B/C; B/G; B/H; B/K; B/L; B/R; C/G; C/H; C/K; C/L; C/R; G/H; G/K; G/L; G/R; H/K; H/L; H/R; K/L; K/R; L/R; A/B/C; A/B/G; A/B/H; A/B/K; A/B/L; A/B/R; A/C/G; A/C/H; A/C/K; A/C/L; A/C/R; A/G/H; A/G/K; A/G/L; A/G/R; A/H/K; A/H/L; A/H/R; A/K/L; A/K/R; A/L/R; B/C/G; B/C/H; B/C/K, B/C/L; B/C/R; C/G/H; C/G/K, C/G/L; C/G/R, G/H/K; G/H/L; G/H/R; H/K/L, H/K/R; K/L/R; A/B/C/G; A/B/C/H; A/B/C/K; A/B/C/L; A/B/C/R; A/C/G/H; A/C/G/K; A/C/G/L; A/C/G/R; A/G/H/K; A/G/H/L; A/G/H/R; A/H/K/L; A/H/K/R; A/K/L/R; B/C/G/H; B/C/G/K; B/C/G/L; B/C/G/R; C/G/H/K; C/G/H/L; C/G/H/R; G/H/K/L; G/H/K/R and H/K/L/R.

The most preferred mixtures of avenanthramides in the oat extract are however A/B, A/C, B/C and A/B/C.

In addition to the above avenanthramide compounds or avenanthramide combinations, the oat extract can further comprise one or more avenanthramide(s) other than the avenanthramides A, B, C, G, H, K, L (non-Collins abbreviations; CAS number 172549-38-1) (also called O (Collins abbreviation) or 2pd) and R, which naturally occur in oats, such as avenanthramides D, E, F U, X, Y (also termed 2), AA, CC or OO or any of the remaining avenanthramide compounds specified in Table 1.

The at least one avenanthramide or mixture of avenanthramides, as described above, may be present in the composition or in the oat extract at a concentration or total amount of 0.5 to 7.0 wt %, based on the dry weight of the composition or the dry weight of the oat extract. In a preferred variant, the composition or oat extract comprises the at least one avenanthramide or mixture of avenanthramides at a concentration or total amount of 1.0 to 6.5 wt %, still more preferred at a concentration or total amount of 2.0 to 5.0 wt %, based on the dry weight of the composition or the dry weight of the oat extract.

In a preferred variant, in the composition or in the oat extract the total amount of the avenanthramides is 1.1 to 2.5 times higher than the total amount of avenanthramides A, B and C, still more preferred the total amount of the avenanthramides is 1.3 to 2.0 times higher than the total amount of avenanthramides A, B and C.

The composition or oat extract further comprises at least one β-glucan compound. β-glucans are a group of high molecular β-D-glucose polysaccharides which are commonly designated as β-glucans and which naturally occur in the cell walls of cereals, bacteria and fungi and exhibit significantly different physiochemical properties depending on the source. In cereals (oat and barley) β-glucans are composed of mixed-linkage (1→3) (1→4)-β-D-glucose units, while it is composed of mixed-linkage of (1→3) (1→6)-β-D-glucose units in mushrooms and yeasts.

β-glucans consist of D-glucopyranose residues linked by β-(1→4) glycosidic bonds/linkages which separate every two, three or four D-glucopyranose unit by one β-(1→3) glycosidic bond/linkage; cellulose like fragments consisting of three and four glucose residues are designated as DP3 and DP4, respectively.

The principal component of oat soluble fiber is the linear polysaccharide (1→3), (1→4)-β-D-glucan, usually called β-glucan; these glucans have a molecular weight of 35 to 3100 kDA, a DP3 value of 54.2 to 60.9, a DP4 value of 33.8 to 36.7 and a DP3/DP4 ratio of 1.5 to 2.3 [Siurek et al., Food Science and Technology International 2012, 18(6), 559-568].

Within the context of the present invention, the at least β-glucan is selected from glucans with a mixed β-(1→3)-β-(1→4)-linked glucopyranosyl backbone and having a different molecular weight, which are preferably derived from a cereal source, still more preferred derived from a oat source.

β-glucans are known to have numerous benefits, such as reducing the occurrence of coronary heart disease, decreasing the level of LDL cholesterol and lipids in blood serum, reducing blood pressure, improving sensitivity to insulin and enabling the control of blood glucose levels, as well as antioxidant and anti-inflammatory activity.

The amount of β-glucan present in the composition or oat extract according to the present invention can be between 1.0 and 3.3 wt %, based on the dry weight of the composition or the dry weight of the oat extract. In a preferred variant, the concentration of the at least one β-glucan or the total β-glucans is 1.5 to 2.8 wt %, still more preferred is 1.7 to 2.6 wt %, based on the dry weight of the composition or the dry weight of the oat extract.

The concentration of the at least one avenanthramide or an analogue thereof or the total avenanthramides or analogues thereof and the at least β-glucan or the total β-glucans in the composition or oat extract is selected or adjusted in such a way that the weight ratio of the at least one avenanthramide or an analogue thereof or the total avenanthramides or analogues thereof to the at least one β-glucan or to the total β-glucans is in a range of 1:4 to 4:1. In a preferred variant, the composition or oat extract comprises the at least one avenanthramide or an analogue thereof or the total avenanthramides or analogues thereof and the at least β-glucan or the total β-glucans at a weight ratio in a range of 1:3 to 3:1, more preferably in a range of 1:2 to 2:1 and even more preferably in a range of 1:1.5 to 1.5:1. A most preferred composition or oat extract is one in which the concentration of the at least one avenanthramide or an analogue thereof or the total avenanthramides or analogues thereof to the at least one β-glucan or all the β-glucans is almost equal, i.e. in a ratio of 1:1.

The composition or oat extract according to the first aspect of the present invention is characterised by a very low salt content, i.e. a salt content of ≤1.0 wt %, based on the dry weight of the composition or oat extract as compared to avenanthramide/β-glucan compositions or oat extracts of the prior art. The salt content is mainly composed of cations and anions, preferably selected from the group consisting of $Na^+$, $K^+$, $Mg^{2+}$, $Ca^{2+}$, $Cl^-$, $SO_4^{2-}$ and $PO_4^{3-}$. In a preferred variant, the salt content in the composition or oat extract is even lower, at ≤0.5 wt %, still more preferred at ≤0.25 wt %, based on the dry weight of the composition or the dry weight of the oat extract.

Such a low salt content is advantageous. On the one hand, oil-in-water (o/w) emulsions are the most popular type of over-the-counter personal care emulsions. In such emulsions, the external phase is aqueous, including water and water-soluble components, and the internal phase comprises oil and oil-soluble components. High concentrations of ionised materials (cations and anions) in solution can destabilise the emulsion interface. Lowering the salt content can therefore be considered to be beneficial to emulsion stability. On the other hand, metal ions have a powerful influence on chemical processes and on the performance of many products, as they can for example catalyse the degradation of ingredients used in personal care products. Lowering the content of metal cations can therefore be considered to be beneficial to product and ingredient stability.

The composition or oat extract according to the first aspect of the present invention is further characterised by a relatively low content of free amino acids. The total content of free amino acids ranges from 0.5 to 1.5 wt %, preferably from 0.5 to 1.0 wt %, and is more preferably 0.6 to 0.9 wt %. In the amino acid fraction of the composition or oat extract, phenylalanine and tryptophan are the most dominant amino acids.

L-Phenylalanine and tryptophan are essential α-amino acids meaning that they cannot be synthesized de novo in humans and other animals but must be obtained through nutrients.

L-Phenylalanine is the natural precursor for tyrosine, which is further converted into the monoamine neurotransmitter catecholamines dopamine, norepinephrine (noradrenaline), and epinephrine (adrenaline) or in the cutaneous pigment melanin. The human epidermis has the capacity for total catecholamine biosynthesis. The biosynthesis of the catecholamines depends on the availability of L-tyrosine synthesized from the L-phenylalanine.

L-Phenylalanine may be introduced with dietary products (e.g. eggs, chicken, liver, beef, milk, cheese, soybeans) or nutritional supplements (e.g. aspartame), which are industrially produced by use of *Escherichia coli*. It is widely used in medicine for the treatment of different diseases (e.g. depression, attention deficit-hyperactivity disorder, Parkinson's disease, chronic pain, osteoarthritis, rheumatoid arthritis).

Tryptophan is required for normal growth, is used for the synthesis of proteins and it serves as an in vivo precursor for several bioactive compounds including nicotinamide (vitamin B6), serotonin, melatonin, tryptamine, kynurenine, 3-hydroxykynurenine, and quinolinic and xanthurenic acids.

In another preferred variant of the present invention according to the first aspect, the composition or oat extract comprises or consists of:

0.5 to 7.0 wt %, preferably 1.0 to 6.5 wt %, of total avenanthramides, preferably avenanthramides A, B and C;

1.0 to 3.3 wt %, preferably 1.5 to 2.8 wt %, of total β-glucans;

≤1.0 wt %, preferably ≤0.5 wt %, of salts;

0.5 to 1.5 wt %, preferably 0.6 to 0.9 wt %, of total free amino acids;

>0.05 wt %, preferably >0.075 wt %, of phenylalanine; and

>0.25 wt %, preferably >0.3 wt %, of tryptophan;

based on the dry weight of the composition or the dry weight of the oat extract.

The composition or oat extract according to the first aspect of the present invention, as described above, exhibits an excellent anti-oxidative capacity by means of radical-scavenging activity, as demonstrated in Example 4 below, which makes it beneficial as an antioxidant. The composition or oat extract according to the present invention has a radical-scavenging activity of at least 70% or even more, as determined using an ABTS assay. In a preferred variant of the present invention, the composition or oat extract according to the present invention has a radical-scavenging activity of at least 90% and more preferably at least 95%.

The term "antioxidant" as used in this document refers to a substance or composition that, when present in a mixture or structure containing an oxidisable substrate molecule (such as an oxidisable biological molecule or oxidisable indicator), significantly delays, prevents or even inhibits oxidation of the oxidisable substrate molecule. Antioxidants can act by scavenging biologically important reactive free radicals or other reactive oxygen species (such as the $O^{2-}$, $H_2O_2$, HOCl, ferryl, peroxyl, peroxynitrous and alkoxyl species) or by preventing their formation or by catalytically converting the free radical or other reactive oxygen species into a less reactive species.

The composition or oat extract with enriched avenanthramide and β-glucan, ideally with the two substances in almost equal concentration, exhibit improved beneficial biological activities and properties such as anti-oxidative capacity, due to the presence of both substances. The composition or oat extract can be provided in a easily storable liquid or solid form which is stable (i.e. exhibits oxidative and light stability) and easy to use and dose, by using cosmetically or pharmaceutically accepted liquid or solid carriers, as demonstrated in the examples below.

In a second aspect, the present invention relates to a method for preparing an oat extract, comprising the steps of:

(1) providing an oat source;
(2) extracting the oat source using at least one extracting solvent at a temperature of 30 to 80° C., to obtain an extract mixture or suspension;
(3) removing the extracted insoluble oat source from the extract mixture or suspension, to obtain an extract solution;
(4) removing the organic extracting solvent from the extract solution, to obtain an aqueous extract solution
(5) providing and conditioning a sorbent and providing the sorbent in an adsorption apparatus;
(6) passing the aqueous extract solution through the sorbent in the adsorption apparatus, to adsorb the ingredients of the aqueous extract solution;
(7) eluting the adsorbed ingredients of the aqueous extract solution from the sorbent using at least one eluent solvent, to obtain an eluate; and
(8) optionally removing the eluent solvent from the eluate, to obtain an oat extract fraction.

In the first step of the method according to the present invention, an oat source of any oat species, fresh or dried, or parts thereof, such as grains, husks, trichomes or oat straw, is provided as a starting material. The two main species of oats are *Avena sativa* L. and *Avena nuda* L. (synonyms include *Avena sativa* subsp. *nuda* (L.) after Gillet & Magne, and *Avena sativa* var. *nuda* (L.) after Körn). *A. sativa* is also known as common or husked oat. *A. nuda* is known as naked or huskless oat because the husk is removed when the crop is harvested. Oats can be processed and separated into constituent fractions including oat grains, husks and trichomes. In a preferred variant, the starting material for the oat extract is milled or non-milled grains of the species *Avena sativa* or *Avena nuda* or oat straw.

The results show that the extract obtained from whole, i.e. non-milled grains contains a higher total content of avenanthramides A to C than the extract obtained from milled grains. By contrast, the β-glucan content of the extract from milled grains is higher than in the extract from whole, i.e. non-milled grains.

In a second step, any one of the oat sources described above is extracted using at least one extracting solvent (extractant), to obtain an extract mixture or suspension. Extraction is preferably performed with stirring or by using a shaker.

The extracting solvent (extractant) for favourably extracting the oat source and enriching the avenanthramides and β-glucan is selected from the group consisting of mixtures of water and an organic solvent, wherein the organic solvent is preferably a solvent suitable for foodstuffs or cosmetic or pharmaceutical preparations. It goes without saying that such solvents need be suitable for and compatible with the preparation of foods, cosmetics or pharmaceutical preparations.

In a more preferred variant, the extracting solvent comprises a mixture of water and an alcohol or acetone. The alcohol is preferably selected from the group consisting of methanol, ethanol, n-propanol, isopropanol, n-butanol, isobutanol, t-butanol and mixtures, i.e. combinations, thereof. The most preferred extracting solvents (extractant) for the extraction step of the present invention are methanol, ethanol, n-propanol, isopropanol or acetone or any mixtures respective combinations of said solvents, each in mixture with water. Use of pure water as extracting solvent is not favourable, since water does not extract β-glucan. The use of pure organic solvents is also not advantageous, due to the co-extraction of triglycerides.

The mixing ratio of water to the organic solvent, preferably water to the alcohol or water to acetone, in the extracting solvent is in a range of 10:90 to 90:10 (v/v), preferably in a range of 20:80 to 80:20 (v/v) and most preferably in a range of 30:70 to 70:30 (v/v), based in each case on the resulting extracting solvent.

Particularly preferred extracting solvents (extractants) are: methanol/water (3:7), methanol/water (1:1), methanol/water (7:3), ethanol/water (3:7), ethanol/water (1:1), ethanol/water (1:4), ethanol/water (7:3), isopropanol/water (3:7), isopropanol/water (1:1), isopropanol/water (7:3), acetone/water (3:7), acetone/water (1:1), acetone/water (7:3). Oat extracts obtained by said extracting solvents (extractants) contain Avns and β-glucan in the above described beneficial ratio (see Example 13 and Table 20).

In order to improve the extraction yield, the oat source is extracted at a temperature ranging from 30 to 80° C., preferably from 40 to 70° C. and more preferably from 50 to 60° C. The results show that the extraction yield for milled oat grains increases with increasing temperatures between 40 and 70° C. The total content of avenanthramides A to C increases in parallel between 40 and 60° C., but then deceases at 70° C. Extracting from milled oats gives the best results in terms of yield and avenanthramide content at temperatures between 50 and 60° C., which is therefore preferred. Extracting from non-milled oat grains provides a higher content of avenanthramides A to C at a temperature of 50 to 60° C.

In an optional version of the method according to the present invention, the extract mixture or suspension obtained in the extraction step is cooled, preferably to room temperature.

In addition, the extraction step is performed for a sufficiently long time to extract the soluble substances from the oat source, preferably over a period of at least two hours in order to provide a beneficial and maximum extract yield.

In order to exhaust the extraction process, the extraction step can be repeated, and the extracted oat source can be extracted again with fresh extracting solvent, using an extracting solvent either with the same or a different composition as the first extracting solvent. Extracting solvents with differing polarity can for example be used in order to extend the spectrum of substances to be extracted. The oat source can be extracted two or even three times. In this case, the resulting extract mixtures from the extraction steps are combined.

The extract mixture or suspension thus obtained comprises two fractions: (a) a liquid fraction which contains the extracted oat substances which are soluble in the extracting solvent; and (b) a solid fraction containing the extracted oat source which is insoluble in the extracting solvent.

In a following step of the method according to the second aspect of the present invention, both the liquid and solid fractions of the extract fraction are separated, i.e. the extracted insoluble oat source is removed from the extract mixture or suspension to obtain an extract solution. This separating step can be performed either by sedimentation, discharge of the extract solution, filtration or centrifugation by known methods and conditions. In a preferred version, the solid fraction is separated from the liquid fraction by centrifugation and filtration. The obtained extract solution contains the soluble oat substances such as avenanthramides, β-glucans, salts and amino acids.

In a next step and before the adsorption step, the organic component of the extracting solvent (extractant) is largely or completely removed from the extract solution obtained in the preceding step by distillation, preferably under vacuum. In so doing, an aqueous extract solution is obtained. The aqueous extract solution comprises the organic solvent component in an amount of at most 5% (v/v). The thus obtained aqueous extract solution is optionally diluted with water in order to prevent precipitation of the extracted substances. The aqueous extract solution thus obtained is then processed in the following adsorption step.

In a fifth step of the method according to the second aspect of the present invention, a sorbent is provided and transferred into an adsorption apparatus.

In accordance with the present invention, any suitable adsorption materials (sorbents) which are usually provided for an adsorption/desorption process can be used in step (5) of the method according to the present invention.

Polymeric adsorbent resins exhibit specific properties and selectivity for the purification and extraction of target molecules and are very different from one another. Polymeric adsorbents are spherical synthetic polymers with a defined pore structure and high surface area. They interact with molecules in different ways depending on the surrounding conditions such as temperature, pH, competing molecules, solvents, etc. The hydrophobicity of synthetic adsorbents is governed by the chemical structure of the resin and is the most important characteristic when selecting a suitable adsorbent for a target compound. Aromatic polystyrene adsorbents, such as PuroSorb™ and Macronet® resins, have a strong affinity for hydrophobic molecules.

An apparatus suitable for the present invention is generally a column made of glass or stainless steel, the internal volume of which usually ranges from a few millilitres to a thousand litres, preferably from 1 to 500 litres and more preferably from 20 to 400 litres.

Preferred adsorption materials (sorbents) used in a column according to the invention include various crosslinked polystyrenes, preferably copolymerisates of ethyl vinyl benzene and divinylbenzene, vinyl pyrrolidone and divinylbenzene, vinyl pyridine and divinylbenzene, styrene and divinylbenzene, copolymerisates of acrylic acid, divinyl benzene and aliphatic diene, but also other polymers, such as preferably polyaromatics, polystyrenes, poly(meth)acrylates, polypropylenes, polyesters and polytetrafluoroethylene, etc.

Of these, examples of preferred sorbents used in the method according to the present invention include polymerisates such as Lewatit®, which is a styrene-divinylbenzene copolymer with trialkyl ammonium groups in chloride form, and Amberlite, which is a polystyrene polymerisate or an acrylic ester-based polymerisate.

Before the sorbent is transferred into an adsorption apparatus, the sorbent is preferably washed and conditioned in water in accordance with the supplier's instructions, in order to optimise the adsorption capacity of the sorbent.

In the adsorption step of the method according to the invention, the aqueous extract solution containing the extracted soluble oat substances is applied to the column and passed through the sorbent in the adsorption apparatus, whereby the soluble oat substances such as avenanthramides and β-glucans, originating from the oat source, are adsorbed onto the sorbent.

Due to the selectivity of the sorbent material, inorganic salts such as $Na^+$, $K^+$, $Mg^{2+}$ and $Ca^{2+}$ cations and $Cl^-$, $SO_4^{2-}$ and $PO_4^{3-}$ anions are adsorbed onto the sorbent material to a minor degree only and largely remain in the extract solution passing through the column.

In another preferred embodiment of the adsorption step in the method according to the invention, the flow rate of the aqueous extract solution is adjusted to within a range of 1 to 20 l/m, at least during part of the adsorption procedure. Within this context, the parameter of the flow rate is jointly responsible for the local distribution coefficients between the adsorption material and the extracted oat substances in the extract solution. The flow rate is preferably within a range of 2.5 to 15 l/min and more preferably 5 to 10 l/min.

In another preferred embodiment of the adsorption process in the method according to the invention, the temperature of the extract solution is within a range of 10 to 70° C., at least during part of the adsorption procedure. The parameter of the temperature is likewise jointly responsible for the local distribution coefficient. A temperature range of 20 to 60° C. is more preferred, and a temperature range of 20 to 50° C. is particularly preferred.

The adsorption step is performed by passing the aqueous extract solution through the column at a gravity-induced flow. In another preferred embodiment, the adsorption step is performed using a counterpressure. The counterpressure inside the adsorption apparatus is within a range of 0.1 to 4.0 bars during the adsorption procedure. The counterpressure inside the adsorption apparatus is the pressure produced by the resistance of the adsorption material when the extract solution is pumped through the adsorption apparatus in step (5) of the adsorption procedure. A counterpressure within a range of 0.3 to 2.5 bars is preferred, and a range of 0.8 to 1.5 bars is particularly preferred.

In a following step of the method according to the second aspect of the present invention, the adsorbed substances originating from the extract solution are desorbed from the sorbent by elution using at least one eluent solvent, to obtain an eluate.

The eluent solvent for favourably desorbing the adsorbed oat substances, in particular the at least one avenanthramide or an analogue thereof and the at least β-glucan, is selected from the group consisting of organic solvents or any mixtures thereof with water, wherein the organic solvents are preferably solvents suitable for foodstuffs or cosmetic or pharmaceutical preparations. It goes without saying that such solvents need be suitable for and compatible with the preparation of foods, cosmetics or pharmaceutical preparations.

The organic eluent solvent is preferably selected from the group consisting of methanol, ethanol, n-propanol, isopropanol, n-butanol, isobutanol, t-butanol, acetone or any mixtures, i.e. combinations, thereof. Methanol, ethanol and isopropanol are preferably used as the eluent solvent. The most preferred eluent solvents for the eluting step are ethanol and isopropanol. The above organic eluent solvents are either used in pure form or in any mixture with water.

The mixing ratio of water to organic solvent, preferably water to alcohol, is in a range of 10:90 to 90:10 (v/v), preferably in a range of 20:80 to 80:20 (v/v) and most preferably in a range of 30:70 to 70:30 (v/v), based in each case on the resulting eluent solvent.

In a preferred variant, the desorbing step in the method according to the present invention is performed using a single, i.e. a pure, eluent solvent. Most preferred is the use of pure ethanol.

One preferred variant of the desorption step according to the invention is characterised by a flow rate of the eluent solvent which is adjusted to within a range of 1 to 20 l/m. Within this context, the parameter of the flow rate is jointly responsible for the local distribution coefficients between the adsorption material and the substances to be desorbed. The flow rate is preferably within a range of 2.5 to 15 l/min and more preferably 5 to 10 l/min.

In another preferred variant, the temperature of the eluent solvent of the desorption step in the method according to the invention is in a range of 10 to 70° C., at least during part of the desorption step. The parameter of the temperature is also jointly responsible for the local distribution coefficient between the sorbent and the eluent solvent. A temperature range of 15 to 60° C. is more preferred, and a temperature range of 20 to 50° C. is particularly preferred.

The desorption step in the method according to the present invention is performed by passing the eluent solvent through the column at a gravity-induced flow. In another preferred variant, the desorption step is characterised by a counterpressure inside the apparatus which is in a range of 0.05 to 2.0 bars during the desorption procedure. The counterpressure inside the apparatus is the pressure produced by the resistance of the adsorption material when the eluent solvent is pumped through the adsorption apparatus and is indicated by a manometer. A counterpressure within a range of 0.1 to 1.5 bars is preferred, and a range of 0.2 to 1.0 bars is particularly preferred.

In accordance with another preferred embodiment of the adsorption and desorption processes in the method according to the present invention, the adsorption procedure and desorption procedure can exhibit the same direction or opposite directions.

Following the desorption step in the method according to the second aspect of the present invention, an eluate is obtained which contains the adsorbed and desorbed substances originating from the oat source extract solution.

The eluate thus obtained, preferably an alcoholic eluate, can be used as such in the preparation of foods, food supplements, cosmetic, pharmaceutical or veterinary preparations. Optionally, the eluent solvent can be removed partially or completely from the eluate, to obtain a concentrated or dried oat extract fraction. The eluent solvent is preferably removed by vacuum evaporation or distillation.

In a preferred variant of the method according the present invention, the column and the sorbent are washed with water between the adsorption step (6) and the desorption step (7), in order to remove non-absorbed substances from the sorbent and to yield a pure oat extract in the subsequent method steps. Optionally, excess water in the adsorption apparatus is removed by vacuum or by blowing nitrogen through the sorbent.

The method according to the second aspect of the present invention results in an oat extract fraction which is characterised in that it comprises or consists of at least of one avenanthramide or an analogue thereof, at least one β-glucan and salts. The weight ratio of the least one avenanthramide or an analogue thereof or the total avenanthramides or analogues thereof to the at least β-glucan or to the total β-glucans is in a range of 1:4 to 4:1, preferably in a range of 1:3 to 3:1, more preferably in a range of 1:2 to 2:1 and even more preferably in a range of 1:1.5 to 1.5:1. A most preferred oat extract is one in which the concentration of the at least one avenanthramide or an analogue thereof or the total avenanthramides or analogues thereof to the at least one β-glucan or all the β-glucans is almost equal, i.e. 1:1. The salt content of the oat extract is ≤1.0 wt %, in particular ≤0.5 wt %, based on the dry weight of the composition or oat extract.

Surprisingly, an oat extract enriched in oat avenanthramides and β-glucans can be obtained by performing the extraction step in combination with an adsorption-desorption step using an adsorber resin within the context of the method according to the present invention, wherein the avenanthramides and β-glucans are ideally present at almost equal concentrations. An oat extract is thus provided which combines the beneficial biological activities and properties of both avenanthramides and β-glucans in one extract fraction.

In a third aspect of the present invention, an oat extract is provided which is obtainable using the method according to the second aspect of the present invention. With regard to its ingredients, preferred variants, properties and beneficial effects, reference is made to the detailed description of the composition or oat extract according to the first aspect of the present invention.

As demonstrated by the following examples, the oat extract fraction obtained by the method according to the present invention can be provided in a stable, easily storable liquid or solid form which is easy to use and dose, by using cosmetically or pharmaceutically accepted liquid or solid carriers.

Another beneficial effect is that the oat extract fraction with enriched avenanthramides and β-glucan can be spray-dried in combination with liquid or solid carriers. Spray-dried solid powders or granulates have the advantage that they are easy to handle and dose. Spray-drying is a very gentle drying technique, as it requires only a very short exposure (of less than one minute) to higher temperatures, making it particularly suitable for sensitive ingredients. It is also a relatively cheap technique, which also allows solutions with low dry matter and low viscosity to be dried. Spray-drying is a well-established drying technology, available at commercial scale, which also allows the use of additives such as dextrins or cyclodextrins, other modified starches or gum acacia, to influence the product parameters.

The particle size can also be adapted from smaller particles (around 0.07 mm) to large particles (up to around 0.4 mm) depending on the respective needs and requirements, for example by producing agglomerated powders using for example spray bed drying technology. This allows free-flowing and almost dust-free powders to be prepared.

The spray-dried oat extract fraction with enriched avenanthramides and β-glucan is also completely stable against oxidative degradation and against light-induced degradation, as demonstrated by the examples below.

The composition or oat extract according to the present invention is preferably used in combination with polyols such as 1,2-propanediol (propylene glycol), 1,3-propanediol, 1,2-butanediol, 1,3-butanediol (butylene glycol), 1,2-pentanediol, 1,2-hexanediol and glycerol alone or as mixture with water which are known compound commonly used as ingredient in cosmetics. As clearly shown in Example 9, the oat extract fraction with enriched avenanthramides and β-glucan in combination with glycerol and 1,2-pentanediol is stable against oxidative degradation and against light-induced degradation. The oat extract fraction with enriched avenanthramides and β-glucan is also brighter in colour than the extracts according to the prior art.

Due to the presence of both avenanthramides and β-glucans at almost equal concentrations, and the enhanced anti-oxidant, anti-inflammatory, anti-itching, anti-irritant and anti-atherogenic activities of both avenanthramides and β-glucan, the composition or oat extract fraction with enriched avenanthramides and β-glucan according to the present invention can be favourably used as a dermatological cosmetic or as a medicament in the prevention and treatment of dermatological disorders. Due to their anti-oxidant and strong cholesterol and triglyceride lowering properties of avenanthramides and β-glucan, which is known for over two decades, the composition and oat extract fraction according to the present invention, can also be favourably used in the prevention and/or treatment of dermatological diseases associated with increased ROS production or prevention and/or treatment of cardiovascular diseases and of allergic reactions.

A fourth aspect of the present invention therefore relates to the use of the composition or oat extract according to the first aspect of the present invention as a cosmetic or medicament.

Because of its improved beneficial biological activities and properties, due to the presence of both avenanthramides and β-glucans, the composition or oat extract according to the first aspect of the present invention is beneficially suitable in skin care, scalp care, hair care, nail care or in the prevention and/or treatment of skin conditions, intolerant and sensitive skin, skin irritation, skin reddening, wheals, pruritus (itching), skin aging, wrinkle formation, loss of skin volume, loss of skin elasticity, pigment spots, pigment abnormalities, or dry skin, i.e. for moisturising the skin.

In addition, the composition or oat extract according to the first aspect of the present invention is beneficially suitable for use in the prevention and/or treatment of dermatological or keratological diseases, preferably of dermatological or keratological diseases having a barrier related, inflammatory, immunoallergic, atherogenic, xerotic or hyperproliferative type component or in the prevention and/or treatment of dermatological diseases associated with increased ROS production or in the prevention and/or treatment of cardiovascular diseases, allergic reactions, coronary heart disease, for decreasing the level of LDL cholesterol and lipids in blood serum, for reducing blood pressure and for improving sensitivity to insulin and for enabling the control of blood glucose levels.

The dermatological or keratological disorders are selected from the group consisting of eczema, psoriasis, seborrhea, dermatitis, erythema, pruritus (itching), otitis, inflammation, irritation, fibrosis, *Lichen planus, Pityriasis rosea Pityriasis versicolor*, autoimmune bullous diseases, urticarial, angiodermal and allergic skin reactions, and wound healing, and/or the skin diseases associated with increased ROS production are selected from the group consisting of atopic dermatitis, neurodermitis, psoriasis, rosacea, acneiform eruptions, sebostasis and xerosis.

The use of the composition or oat extract for these respective purposes corresponds to a method for imparting the respective therapeutic activity to a substance by adding a therapeutically effective amount of the composition or oat extract.

Within the context of the present invention, an effective amount of a composition is the amount of each active component that is sufficient to show a benefit, such as a reduction in a symptom associated with the disorder, disease or condition to be treated. When applied to a combination, as in the present case, the term refers to the amount of the combined active ingredients resulting in the benefit.

Due to its marked radical-scavenging activity, and therefore anti-oxidative effect, the composition or oat extract according to the first aspect of the present invention is beneficially suitable for the preparation of foods, food supplements or veterinary products.

The composition or oat extract according to the present invention can be easily incorporated into conventional foods, food supplements, cosmetic, pharmaceutical or veterinary preparations.

A final aspect of the present invention therefore relates to foods, food supplements, cosmetic, pharmaceutical or veterinary preparations which comprise the composition or oat extract according to the present invention and/or are obtained using the method according to the present invention. In a preferred variant of the present invention, a functional food which includes the composition or oat extract according to the present invention is provided as an effective ingredient for preventing or ameliorating the above disorders.

In a preferred variant, the foods, food supplements, cosmetic, pharmaceutical or veterinary preparations comprise the composition or oat extract according to the present invention or are obtained using the method according to the present invention in an amount of 0.0001 to 10 wt %, more preferred 0.0005 to 5 wt %, most preferred 0.001 to 1 wt %, based on the total weight of the composition.

Within this context, it is also possible—and in some cases advantageous—to combine the composition or oat extract according to the present invention or the cosmetic or pharmaceutical preparations that contain a composition or an oat extract according to the present invention with other active compounds, for example other synergistically intensifying substances, such as anti-inflammatories, antibacterial or antimycotic substances, substances having a reddening-alleviating or itch-alleviating action, lenitive substances, moisturisers and/or cooling agents and/or antioxidants, preservatives, (metal) chelating agents, penetration enhancers, and/or cosmetically or pharmaceutically acceptable excipients, as in detail described and exemplified below.

An active substance means a substance or compound that imparts a primary utility to a composition or formulation. Examples of such active substances include antioxidants, preservatives, (metal) chelating agents, penetration enhancers, etc. An excipient refers to an inactive substance used to formulate cosmetics or pharmaceuticals as a result of processing or manufacture.

Since dermatological conditions or diseases are often associated with dry skin, scratched skin, skin lesions or even inflammation, the composition or oat extract or cosmetic and/or pharmaceutical preparations that contain a composition or an oat extract according to the present invention particularly advantageously contains a skin-moisturising and/or moisture-retaining substance, a cooling agent, an osmolyte, a keratolytic substance, a nurturing substance, an anti-inflammatory, antibacterial or antimycotic substance and/or a substance having a reddening-alleviating or itch-alleviating action and/or a lenitive substance.

Itching occurs with particular intensity when the skin is dry. The use of skin-moisturising and/or moisture-retaining substances can significantly alleviate itching. The composition or oat extract or cosmetic or pharmaceutical preparations that contain a composition or an oat extract according to the present invention can therefore also be particularly advantageously combined with one or more skin-moisturising and/or moisture-retaining substances. The composition or oat extract or cosmetic or pharmaceutical preparations according to the present invention can therefore advantageously also contain the following moisturising and/or moisture-retaining substances: sodium lactate, urea, urea derivatives, alcohols, glycerol, diols such as propylene glycol, hexylene glycol, 1,2-pentanediol, 1,2-hexanediol, 1,2-heptanediol, 1,2-octanediol, 1,2-nonanediol, 1,2-decanediol or mixtures of said diols, in particular mixtures of 1,2-hexanediol and 1,2-octanediol, collagen, elastin or hyaluronic acid, diacyl adipates, petrolatum, urocanic acid, lecithin, panthenol, phytantriol, lycopene, (pseudo-)ceramides, glycosphingolipids, cholesterol, phytosterols, chitosan, chondroitin sulphate, lanolin, lanolin esters, amino acids, alpha-hydroxy acids (such as citric acid, lactic acid, malic acid) and their derivatives, mono-, di- and oligosaccharides such as glucose, galactose, fructose, mannose, fructose and lactose, polysugars such as β-glucans, in particular 1,3-1,4-β-glucan from oats, alpha-hydroxy fatty acids, triterpene acids such as betulinic acid or ursolic acid, and algae extracts.

Depending on the substance, the concentration of the moisture retention regulators used is between 0.1 and 10% (m/m) and preferably between 0.5 and 5% (m/m), based on the total weight of a ready-to-use cosmetic or pharmaceutical end product. These data apply in particular to such diols as are advantageously to be used, such as hexylene glycol, 1,2-pentanediol, 1,2-hexanediol, 1,2-octanediol and 1,2-decanediol, as well as mixtures of 1,2-hexanediol and 1,2-octanediol.

The use of cooling agents can alleviate itching. The composition or oat extract or cosmetic or pharmaceutical preparations that contain a composition or an oat extract according to the present invention can therefore also be particularly advantageously combined with one or more cooling agent(s). Preferred individual cooling agents for use within the framework of the present invention are listed below. The person skilled in the art can add many other cooling agents to this list; the cooling agents listed can also be used in combination with one another: l-menthol, d-menthol, racemic menthol, menthone glycerol acetal (trade name: Frescolat® MGA), menthyl lactate (trade name: Frescolat® ML; menthyl lactate is preferably l-menthyl lactate, in particular l-menthyl l-lactate), substituted menthyl-3-carboxamides (such as menthyl-3-carboxylic acid N-ethyl amide), 2-isopropyl-N-2,3-trimethyl butanamide, substituted cyclohexane carboxamides, 3-menthoxypropane-1,2-diol, 2-hydroxyethyl menthyl carbonate, 2-hydroxypropyl menthyl carbonate, N-acetylglycine menthyl ester, isopulegol, hydroxycarboxylic acid menthyl esters (such as menthyl 3-hydroxybutyrate), monomenthyl succinate, 2-mercaptocyclodecanone, menthyl 2-pyrrolidin-5-one carboxylate, 2,3-dihydroxy-p-menthane, 3,3,5-trimethyl cyclohexanone glycerol ketal, 3-menthyl-3,6-di- and trioxaalkanoates, 3-menthyl methoxyacetate and icilin.

Cooling agents which are preferred due to their particular synergistic effect are l-menthol, d-menthol, racemic menthol, menthone glycerol acetal (trade name: Frescolat® MGA), menthyl lactate (preferably l-menthyl lactate, in particular l-menthyl l-lactate (trade name: Frescolat® ML)), substituted menthyl-3-carboxamides (such as menthyl-3-carboxylic acid N-ethyl amide), 2-isopropyl-N-2,3-trimethyl butanamide, substituted cyclohexane carboxamides, 3-menthoxypropane-1,2-diol, 2-hydroxyethyl menthyl carbonate, 2-hydroxypropyl menthyl carbonate and isopulegol.

Particularly preferred cooling agents are l-menthol, racemic menthol, menthone glycerol acetal (trade name: Frescolat® MGA), menthyl lactate (preferably l-menthyl lactate, in particular l-menthyl l-lactate (trade name: Frescolat® ML)), 3-menthoxypropane-1,2-diol, 2-hydroxyethyl menthyl carbonate and 2-hydroxypropyl menthyl carbonate.

Very particularly preferred cooling agents are l-menthol, menthone glycerol acetal (trade name: Frescolat® MGA) and menthyl lactate (preferably l-menthyl lactate, in particular l-menthyl l-lactate (trade name: Frescolat® ML).

Depending on the substance, the concentration of the cooling agents used is preferably between 0.01 and 20 wt % and particularly preferably between 0.1 and 5 wt %, based on the total weight of a ready-to-use cosmetic or pharmaceutical end product.

The composition or oat extract or cosmetic or pharmaceutical preparations that contain a composition or an oat extract according to the present invention can also be used together with one or more osmolyte(s). Examples of osmolytes which may be mentioned here include substances from the group comprising sugar alcohols (myoinositol, mannitol, sorbitol), quaternary amines such as taurine, choline, betaine, betaine glycine, ectoin, diglycerol phosphate, phosphorylcholine or glycerophosphorylcholines, amino acids such as glutamine, glycine, alanine, glutamate, aspartate or proline, phosphatidylcholine, phosphatidylinositol, inorganic phosphates, and polymers of said compounds, such as proteins, peptides, polyamino acids and polyols. All osmolytes simultaneously have a skin-moisturising action.

Preferably, keratolytic substances can also be combined with the composition or oat extract according to the present invention. Keratolytic compounds include the large group of alpha-hydroxy acids. Salicylic acid is for example preferably used.

In cosmetic or pharmaceutical preparations containing the composition or oat extract according to the present invention for the topical cosmetic or pharmaceutical treatment of for example dry and/or itchy skin, a high proportion of in particular nurturing substances is also particularly advantageous because of the reduced trans-epidermal water loss due to lipophilic components. In one preferred embodiment, the cosmetic or pharmaceutical preparations contain one or more nurturing animal and/or vegetable fats and oils such as olive oil, sunflower oil, refined soybean oil, palm oil, sesame oil, rapeseed oil, almond oil, borage oil, evening primrose oil, coconut oil, shea butter, jojoba oil, sperm oil, tallow, neatsfoot oil and lard, and optionally other nurturing components such as fatty alcohols having 8 to 30 C atoms. The fatty alcohols used here can be either saturated or unsaturated and either linear or branched. Nurturing substances which can be particularly preferably combined with the mixtures according to the present invention also include in particular ceramides, understood here to mean N-acylsphingosines (fatty acid amides of sphingosine) or synthetic analogues of such lipids (so-called pseudo-ceramides) which markedly improve the water retention capacity of the stratum corneum; phospholipids, such as soy lecithin, egg lecithin and cephalins; and petrolatum, paraffin oils and silicone oils, the latter including inter alia dialkyl- and alkylarylsiloxanes such as dimethylpolysiloxane and methylphenylpolysiloxane and their alkoxylated and quaternised derivatives.

The composition or oat extract or cosmetic or pharmaceutical preparations that contain the composition or oat extract according to the present invention can also contain other anti-inflammatory active compounds or active compounds exhibiting anti-reddening and anti-itching activity. Within this context, any anti-inflammatory active compounds and active compounds that alleviate reddening and itching and are suitable or customary in cosmetic and/or dermatological applications can be used. Advantageously, the anti-inflammatory active compounds and active compounds which alleviate reddening and/or itching that are used are steroidal anti-inflammatory substances of the corticosteroid type, such as for example hydrocortisone, dexamethasone, dexamethasone phosphate, methylprednisolone or cortisone, wherein this list may be expanded by adding other steroidal anti-inflammatory agents. Non-steroidal anti-inflammatory agents can also be used, for example: oxicams, such as piroxicam or tenoxicam; salicylates, such as aspirin, Disalcid®, Solprin® or fendosal; acetic acid derivatives, such as diclofenac, fenclofenac, indomethacin, sulindac, tolmetin or clindanac; fenamates, such as mefenamic, meclofenamic, flufenamic or niflumic acid; propionic acid derivatives, such as ibuprofen, naproxen, benoxaprofen; or pyrazoles, such as phenylbutazone, oxyphenylbutazone, febrazone or azapropazone. Alternatively, natural anti-inflammatory substances and substances that alleviate reddening and/or itching can be used. Plant extracts, special highly active plant extract fractions and also highly pure active substances isolated from plant extracts can be used. Extracts, fractions and active substances from chamomile, *Aloe vera, Commiphora* species, *Rubia* species, willows, willow-herb, ginger, marigold, arnica, *Glycyrrhiza* species, *Echinacea* species, *Rubus* species and pure substances such as inter alia bisabolol, apigenin, apigenin-7-glucoside, gingerols such as [6]-gingerol, paradols such as [6]-paradol, boswellic acid, phytosterols, glycyrrhizine, glabridin or licochalcone A are particularly preferred. The preparations containing histamine-release inhibitors can also contain mixtures of two or more anti-inflammatory active compounds.

The composition or oat extract or cosmetic or pharmaceutical preparations that contain the composition or oat extract according to the present invention can also contain active compounds for preservative purposes, wherein any preservatives may be used which are suitable or customary in cosmetic and/or dermatological applications and which are advantageously selected from the group consisting of preservatives such as inter alia benzoic acid, its esters and salts; propionic acid and its salts; salicylic acid and its salts; 2,4-hexanoic acid (sorbic acid) and its salts; formaldehyde and paraformaldehyde; 2-hydroxybiphenyl ether and its salts; 2-zincsulphidopyridine N-oxide; inorganic sulphites and bisulphites; sodium iodate; chlorobutanol; 4-hydroxybenzoic acid and its salts and esters; dehydroacetic acid; formic acid; 1,6-bis(4-amidino-2-bromophenoxy)-n-hexane and its salts; the sodium salt of ethylmercury-(II)-thiosalicylic acid; phenylmercury and its salts; 10-undecylenic acid and its salts; 5-amino-1,3-bis(2-ethylhexyl)-5-methylhexahydropyrimidine; 5-bromo-5-nitro-1,3-dioxane; 2-bromo-2-nitro-1,3-propanediol; 2,4-dichlorobenzyl alcohol; N-(4-chlorophenyl)-N'-(3,4-dichlorophenyl)urea; 4-chloro-m-cresol; 2,4,4'-trichloro-2'-hydroxy-diphenyl ether; 4-chloro-3,5-dimethylphenol; 1,1'-methylene-bis(3-(1-hydroxymethyl-2,4-dioximidazolidin-5-yl)urea); poly (hexamethylene biguanide) hydrochloride; 2-phenoxyethanol; hexamethylenetetramine; 1-(3-chloroallyl)-3,5,7-triaza-1-azoniaadamantane chloride; 1-(4-chlorophenoxy)-1(1H-imidazol-1-yl)-3,3-dimethyl-2-butanone; 1,3-bis(hydroxymethyl)-5,5-dimethyl-2,4-imidazolidinedione; benzyl alcohol; Octopirox®; 1,2-dibromo-2,4-dicyanobutane; 2,2'-methylene-bis(6-bromo-4-chloro-phenol); bromochlorophene; mixture of 5-chloro-2-methyl-3 (2H)-isothiazolinone and 2-methyl-3(2H)isothiazolinone with magnesium chloride and magnesium nitrate; 2-benzyl-4-chlorophenol; 2-chloroacetamide; chlorhexidine; chlorhexidine acetate; chlorhexidine gluconate; chlorhexidine hydrochloride; 1-phenoxy-propan-2-ol; N-alkyl(C12-C22) trimethylammonium bromide and chloride; 4,4-dimethyl-1,3-oxazolidine; N-hydroxymethyl-N-(1,3-di(hydroxymethyl)-2,5-dioxoimidazolidin-4-yl)-N'-hydroxymethylurea; 1,6-bis(4-amidinophenoxy)-n-hexane and its salts; glutaraldehyde 5-ethyl-1-aza-3,7-dioxabicyclo(3.3.0)octane; 3-(4-chlorophenoxy)-1,2-propanediol; hyamine; alkyl(C8-C18) dimethylbenzylammonium chloride; alkyl(C8-C18) dimethylbenzylammonium bromide; alkyl(C8-C18) dimethylbenzylammonium saccharinate; benzylhemiformal; 3-iodo-2-propynyl butylcarbamate; or sodium ((hydroxymethyl)amino)acetate.

Other antibacterial or antimycotic active substances can also particularly advantageously be used in the composition or oat extract or cosmetic or pharmaceutical preparations that contain the composition or oat extract according to the present invention, wherein any antibacterial or antimycotic active substances can be used which are suitable or customary in cosmetic and/or dermatological applications. In addition to the large group of conventional antibiotics, other products which are advantageous here include those relevant to cosmetics such as in particular triclosan, climbazole, octoxyglycerin, Octopirox® (1-hydroxy-4-methyl-6-(2,4,4-trimethylpentyl)-2(1H)-pyridone 2-aminoethanol salt), chitosan, farnesol, glycerol monolaurate or combinations of said substances, which are used inter alia against underarm odour, foot odour or dandruff.

The composition or oat extract or cosmetic and/or pharmaceutical preparations that contain a composition or an oat extract according to the present invention can also contain one or more lenitive substances, wherein any lenitive substances can be used which are suitable or customary in cosmetic and/or pharmaceutical applications such as alpha-bisabolol, azulene, guaiazulene, 18-beta-glycyrrhetinic acid, allantoin, *Aloe vera* juice or gel, extracts of *Hamamelis virginiana* (witch hazel), *Echinacea* species, *Centella asiatica*, chamomile, *Arnica montana, Glycyrrhiza* species, algae, seaweed and *Calendula officinalis*, and vegetable oils such as sweet almond oil, baobab oil, olive oil and panthenol, Laureth-9, Trideceth-9 and 4-t-butylcyclohexanol.

In addition, the composition or oat extract or cosmetic or pharmaceutical preparations that contain a composition or an oat extract according to the present invention can also particularly advantageously be used in combination with perspiration-inhibiting active compounds (antiperspirants) for controlling body odour. Perspiration-inhibiting active compounds used include in particular aluminium salts, such as aluminium chloride, chlorohydrate, nitrate, sulphate, acetate, etc. The use of zinc, magnesium or zirconium compounds can however also be advantageous. Aluminium salts and, to a somewhat lesser extent, aluminium/zirconium salt combinations have proven useful in cosmetic and dermatological antiperspirants. Partially neutralised aluminium hydroxychlorides, which are therefore more tolerable to the skin but are not quite as effective, are also noteworthy. Substances other than aluminium salts can also be used, such as for example: (a) protein-precipitating substances such as inter alia formaldehyde, glutaraldehyde, natural and synthetic tanning agents and trichloroacetic acid, which cause surface closure of the sweat glands; (b) local anaesthetics, including dilute solutions of for example lidocaine, prilocaine or mixtures of the same, which switch off the sympathetic supply to the sweat glands by blocking the peripheral nerve paths; (c) zeolites of the X, A or Y type, which reduce sweat secretion and also act as adsorbents for bad odours; and (d) botulinus toxin (the toxin of the bacterium *Clostridium botulinum*), which is also used in hyperhidrosis (pathological increase in sweat secretion), and the action of which is based on irreversibly blocking the release of the transmitter substance acetylcholine which is relevant to sweat secretion.

A combination with (metal) chelating agents can also be advantageous in the composition or oat extract or the cosmetic or pharmaceutical preparations that contain a composition or an oat extract according to the present invention, wherein any metal chelating agents can be used which are suitable or customary in cosmetic and/or dermatological applications. Preferred (metal) chelating agents include α-hydroxy fatty acids, phytic acid, lactoferrin, α-hydroxy acids, such as inter alia gluconic acid, glyceric acid, glycolic acid, isocitric acid, citric acid, lactic acid, malic acid, mandelic acid, tartaric acid, as well as humic acids, bile acids, bile extracts, bilirubin, biliverdin or EDTA, EGTA and their derivatives. The use of one or more chelating agent(s) improves the stability of the composition or oat extract or the cosmetic or pharmaceutical preparations that contain a composition or an oat extract according to the present invention In order to be used, the preparations containing the composition or oat extract according to the present invention are applied to the skin and/or hair in an adequate amount in such manner as is customary with cosmetics and dermatological products. Within this context, cosmetic and dermatological preparations that contain a mixture according to the present invention and which additionally act as a sunscreen offer particular advantages. Advantageously, these preparations contain at least one UVA filter and/or at least one UVB filter and/or at least one inorganic pigment. Within this context, the preparations can take various forms such as are for example customarily employed for this type of preparation, such as for example solutions, water-in-oil (W/O) emulsions, oil-in-water (O/W) emulsions or multiple emulsions such as water-in-oil-in-water (W/O/W) emulsions, gels, hydrodispersions, solid sticks or aerosols.

The composition or oat extract or cosmetic or pharmaceutical preparations that contain a composition or an oat extract according to the present invention can advantageously be combined with substances that absorb UV radiation in the UVB range, the total amount of filter substances being for example 0.01 to 40% (m/m), preferably 0.1 to 10% (m/m), in particular 1.0 to 5.0% (m/m), based on the dry weight of the preparations, in order to provide cosmetic preparations that protect the hair and/or skin against the entire range of ultraviolet radiation. They can also serve as sunscreens for hair. If the preparations according to the present invention contain UVB filter substances, these can be oil-soluble or water-soluble. Advantageous oil-soluble UVB filters include: 3-benzylidene camphor derivatives, preferably 3-(4-methylbenzylidene)camphor, 3-benzylidenecamphor; 4-aminobenzoic acid derivatives, preferably 2-ethylhexyl 4-(dimethylamino)benzoate, amyl 4-(dimethylamino)benzoate; esters of cinnamic acid, preferably 2-ethylhexyl 4-methoxycinnamate, isopentyl 4-methoxycinnamate; esters of salicylic acid, preferably 2-ethylhexyl salicylate, 4-isopropylbenzyl salicylate, homomenthyl salicylate; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably di(2-ethylhexyl) 4-methoxybenzalmalonate, 2,4,6-trianilino-(p-carbo-2'-ethyl-1'-hexyloxy)-1,3,5-triazine. Advantageous water-soluble UVB filters include salts of 2-phenylbenzimidazole-5-sulphonic acid, such as its sodium, potassium or triethanolammonium salts, as well as the sulphonic acid itself; sulphonic acid derivatives of benzophenones, preferably 2-hydroxy-4-methoxybenzophenone-5-sulphonic acid and its salts; sulphonic acid derivatives of 3-benzylidene camphor, such as for example 4-(2-oxo-3-bornylidenemethyl)benzenesulphonic acid, 2-methyl-5-(2-oxo-3-bornylidene-methyl)sulphonic acid and their salts and also 1,4-di(2-oxo-10-sulpho-3-bornylidenemethyl)-benzene and its salts (the corresponding 10-sulphato compounds, such as the corresponding sodium, potassium and triethanolammonium salts), and benzene-1,4-di(2-oxo-3-bornylidenemethyl-10-sulphonic acid.

It can also be advantageous to employ UVA filters, such as are customarily contained in cosmetic preparations. These substances are preferably derivatives of dibenzoylmethane, in particular 1-(4'-tert-butylphenyl)-3-(4'-methoxyphenyl) propane-1,3-dione and 1-phenyl-3-(4'-isopropylphenyl)propane-1,3-dione. The amounts used for the UVB combination can be used analogously.

The composition or oat extract or the cosmetic or pharmaceutical preparations, that contain a composition or an oat extract according to the present invention can advantageously also be combined with other cosmetic auxiliaries such as are customarily used in such preparations, such as for example antioxidants, perfume oils, anti-foaming agents, colorants, pigments having a colouring action, thickeners, surface-active substances, emulsifiers, plasticising substances, moistening and/or moisture-retaining substances, fats, oils, waxes or other conventional constituents of a cosmetic preparation, such as alcohols, polyols, polymers, foam stabilisers, electrolytes, organic solvents or silicone derivatives. Any conceivable antioxidants, perfume oils, anti-foaming agents, colorants, pigments having a colouring action, thickeners, surface-active substances, emulsifiers, plasticising substances, moistening and/or moisture-retaining substances, fats, oils, waxes, alcohols, polyols, polymers, foam stabilisers, electrolytes, organic solvents or silicone derivatives that are suitable or customary in cosmetic and/or dermatological applications can be used here in accordance with the invention.

A high content of treatment substances is usually advantageous in preparations containing the composition or oat extract according to the present invention for the topical prophylactic or cosmetic treatment of the skin. In accordance with a preferred embodiment, the compositions contain one or more animal and/or vegetable treatment fats and oils, such as olive oil, sunflower oil, purified soybean oil, palm oil, sesame oil, rapeseed oil, almond oil, borage oil, evening primrose oil, coconut oil, shea butter, jojoba oil, sperm oil, beef tallow, neatsfoot oil and lard, and optionally other treatment constituents such as for example C8-C30 fatty alcohols. The fatty alcohols used here can be saturated or unsaturated and straight-chain or branched, wherein examples include decanol, decenol, octanol, octenol, dodecanol, dodecenol, octadienol, decadienol, dodecadienol, oleyl alcohol, ricinoleyl alcohol, erucic alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol, as well their guerbet alcohols; this list may be extended as desired to include other alcohols which structurally are chemically related. The fatty alcohols preferably originate from natural fatty acids and are usually prepared from the corresponding esters of the fatty acids by reduction. Fatty alcohol fractions formed by reduction from naturally occurring fats and fat oils can also be used, such as for example beef tallow, peanut oil, colza oil, cottonseed oil, soybean oil, sunflower oil, palm kernel oil, linseed oil, maize oil, castor oil, rapeseed oil, sesame oil, cocoa butter and cocoa fat.

The treatment substances that can preferably be combined with the composition or oat extract according to the present invention can also include: ceramides, being understood to be N-acylsphingosines (fatty acid amides of sphingosine) or synthetic analogues of such lipids (so-called pseudo-ceramides) which clearly improve the water retention capacity of the stratum corneum; phospholipids, for example soy lecithin, egg lecithin and cephalins; vaseline, paraffin and silicone oils, the latter including inter alia dialkyl- and alkylarylsiloxanes such as dimethylpolysiloxane and methylphenylpolysiloxane, as well as their alkoxylated and quaternised derivatives.

Hydrolysed animal and/or vegetable proteins can also advantageously be added to the preparations containing the composition or oat extract according to the present invention. Advantageous examples in this regard include in particular elastin, collagen, keratin, lactoprotein, soy protein, oat protein, pea protein, almond protein and wheat protein fractions or corresponding hydrolysed proteins, as well as their condensation products with fatty acids, and also quaternised hydrolysed proteins, wherein the use of hydrolysed vegetable proteins is preferred.

If a cosmetic or dermatological preparation containing the composition or oat extract according to the present invention is a solution or lotion, then solvents which can be used include: water or aqueous solutions; fatty oils, fats, waxes and other natural and synthetic fatty bodies, preferably esters of fatty acids with alcohols having a low C number, such as isopropanol, propylene glycol or glycerol, or esters of fatty alcohols with alkanoic acids having a low C number or with fatty acids; alcohols, diols or polyols having a low C number, and their ethers, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products. Mixtures of the abovementioned solvents are in particular used. In the case of alcoholic solvents, water can be an additional constituent.

The composition or oat extract or cosmetic or pharmaceutical preparations that contain a composition or an oat extract according to the present invention can also contain antioxidants, wherein any antioxidants suitable or customary in cosmetic and/or dermatological applications can be used. Advantageously, the antioxidants are selected from the group consisting of amino acids (for example glycine, histidine, tyrosine, tryptophan) and their derivatives, imidazoles (for example urocanic acid) and their derivatives, peptides such as D,L-carnosine, D-carnosine, L-carnosine and their derivatives (for example anserine), carotenoids, carotenes (for example α-carotene, β-carotene, lycopene) and their derivatives, lipoic acid and its derivatives (for example dihydrolipoic acid), aurothioglucose, propylthiouracil and other thiols (for example thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilauryl thiodipropionate, distearyl thiodipropionate, thiodipropionic acid and their derivatives (esters, ethers, peptides, lipids, nucleotides, nucleosides and salts) as well as sulphoximine compounds (for example buthionine sulphoximines, homocysteine sulphoximines, buthionine sulphones, penta-, hexa-, hepta-thionine sulphoximine) in very low tolerated doses, and also (metal) chelating agents, for example α-hydroxy fatty acids, palmitic acid, phytic acid, lactoferrin, α-hydroxy acids (for example citric acid, lactic acid, malic acid), humic acid, bile acid, bile extracts, bilirubin, biliverdin, EDTA, EGTA and their derivatives, unsaturated fatty acids and their derivatives (for example γ-linolenic acid, linoleic acid, oleic acid), folic acid and its derivatives, ubiquinone and ubiquinol and their derivatives, Vitamin C and its derivatives (for example ascorbyl palmitate, magnesium ascorbyl phosphate, ascorbyl acetate), tocopherols and their derivatives (for example Vitamin E acetate), Vitamin A and its derivatives (for example Vitamin A palmitate) and also coniferyl benzoate of benzoin resin, rutinic acid and its derivatives, ferrulic acid and its derivatives, butylhydroxytoluene, butylhydroxyanisole, nordihydroguaiacic acid, nordihydroguaiaretic acid, trihydroxybutyrophenone, uric acid and its derivatives, mannose and its derivatives, zinc and its derivatives (for example ZnO, $ZnSO_4$), selenium and its derivatives (such as selenium methionine), stilbenes and their derivatives (such as stilbene oxide, trans-stilbene oxide), as well as the derivatives (such as salts, esters, ethers, sugars, nucleotides, nucleosides, peptides and lipids) of said active compounds such as are suitable in accordance with the invention.

The composition or oat extract or cosmetic or pharmaceutical preparations that contain a composition or an oat extract according to the present invention can also contain vitamins and vitamin precursors, wherein any vitamins and vitamin precursors which are suitable or customary in cosmetic and/or dermatological applications can be used. Particular mention may be made here of vitamins and vitamin precursors such as tocopherols, Vitamin A, nicotinic acid and nicotinamide, other B-complex vitamins, in particular biotin, and Vitamin C. Other examples within this group which are preferably used include pantothenyl alcohol and its derivatives, in particular its esters and ethers, as well as derivatives of pantothenyl alcohols obtained cationically, such as for example pantothenyl alcohol triacetate, pantothenyl alcohol monoethyl ether and its monoacetate and also cationic pantothenyl alcohol derivatives.

The composition or oat extract or cosmetic or pharmaceutical preparations that contain a composition or an oat extract according to the present invention can also contain active compounds having a skin-lightening action, wherein any skin-lightening active compounds that are suitable or customary in cosmetic and/or dermatological applications can be used in accordance with the invention. Advantageous skin-lightening active compounds in this regard include kojic acid, hydroquinone, arbutin, ascorbic acid, magnesium ascorbyl phosphate, resorcinols, liquorice root extracts and their constituents glabridin or licochalcone A, or extracts from *Rumex* and *Ramulus* species, extracts from pine species (*Pinus*) or extracts from *Vitis* species which contain inter alia skin-lightening stilbene derivatives.

The composition or oat extract or cosmetic preparations that contain a composition or an oat extract according to the present invention can also contain active compounds having a skin-tanning action, wherein any skin-tanning active compounds that are suitable or customary in cosmetic and/or dermatological applications can be used. Dihydroxyacetone (DHA; 1,3-dihydroxy-2-propanone) may be mentioned here by way of example. DHA can be provided in either monomer or dimer form, the proportion of dimers being predominant in the crystalline form.

The composition or oat extract or cosmetic or pharmaceutical preparations that contain a composition or an oat extract according to the present invention can also contain mono-, di- and oligo-saccharides such as for example glucose, galactose, fructose, mannose and lactose.

The composition or oat extract or cosmetic or pharmaceutical preparations that contain a composition or an oat extract according to the present invention can also contain plant extracts, which are usually prepared by extraction of the complete plant, but which in individual cases are also prepared exclusively from the blossom and/or leaves, wood, bark or roots of the plant. With regard to the plant extracts which can be used in accordance with the present invention, reference is made in particular to the extracts listed in the table starting on page 44 of the third edition of *Leitfaden zur Inhaltsstoffdeklaration kosmetischer Mittel* (Guide to the Declaration of Constituents of Cosmetic Agents), published by *Industrieverband Körperpflegemittel und Waschmittel e.V.* (IKW) (Industrial Association for Toiletries and Detergents), Frankfurt. Particularly advantageous extracts include aloe, Hamamelis, algae, oak bark, willow-herb, stinging nettles, dead nettles, hops, chamomile, milfoil, arnica, calendula, burdock root, horse-tail, hawthorn, linden blossom, cucumber, almonds, pine needles, horse chestnut, sandalwood, juniper, coconut, mango, apricot, orange, lemon, lime, grapefruit, apple, green tea, grapefruit seed, wheat, oats, barley, sage, thyme, basil, rosemary, birch, mallow, bitter-crass, willow bark, restharrow, coltsfoot, althaea, ginseng and ginger root. Of these, particularly preferred extracts include aloe vera, chamomile, algae, rosemary, calendula, ginseng, cucumber, sage, stinging nettles, linden blossom, arnica and Hamamelis. Mixtures of two or more plant extracts can also be employed. Extraction agents that can be used for preparing said plant extracts include water, alcohols and mixtures thereof. Preferred alcohols in this context are the lower alcohols such as ethanol and isopropanol, but also polyhydric alcohols such as ethylene glycol, propylene glycol and butylene glycol, specifically both as a sole extracting agent and in mixtures with water. The plant extracts can be used in pure form or dilute form in accordance with the invention.

The composition or oat extract or cosmetic or pharmaceutical preparations that contain a composition or an oat extract according to the present invention can also contain anionic, cationic, non-ionic and/or amphoteric surfactants, especially if crystalline or microcrystalline solids, for example inorganic micropigments, are to be incorporated into the preparations according to the present invention. Surfactants are amphiphilic substances that are able to dissolve organic, non-polar substances in water. Surfactants are generally classified according to the nature and charge of the hydrophilic part of the molecule. Four groups can be differentiated here: anionic surfactants, cationic surfactants, amphoteric surfactants and non-ionic surfactants.

Anionic surfactants usually contain carboxylate, sulphate or sulphonate groups as functional groups. In aqueous solution, they form negatively charged organic ions in the acid or neutral medium. Cationic surfactants are characterised almost exclusively by the presence of a quaternary ammonium group. In aqueous solution, they form positively charged organic ions in the acid or neutral medium. Amphoteric surfactants contain both anionic and cationic groups and accordingly behave like anionic or cationic surfactants in aqueous solution, depending on the pH value. They have a positive charge in a strongly acid medium and a negative charge in an alkaline medium. In the neutral pH range, by contrast, they are zwitterionic. Polyether chains are typical of non-ionic surfactants. Non-ionic surfactants do not form ions in an aqueous medium.

Anionic surfactants that can advantageously be used include: acyl amino acids (and their salts), such as: acyl glutamates, for example sodium acyl glutamate, di-TEA-palmitoyl aspartate and sodium caprylic/capric glutamate; acyl peptides, for example palmitoyl-hydrolysed lactoprotein, sodium cocoyl-hydrolysed soy protein and sodium/potassium cocoyl-hydrolysed collagen; sarcosinates, for example myristoyl sarcosinate, TEA-lauroyl sarcosinate, sodium lauroyl sarcosinate and sodium cocoyl sarcosinate; taurates, for example sodium lauroyl taurate and sodium methyl cocoyl taurate; acyl lactylates, for example lauroyl lactylate and caproyl lactylate; alaninates; carboxylic acids and derivatives, such as for example lauric acid, aluminium stearate, magnesium alkanolate and zinc undecylenate; ester carboxylic acids, for example calcium stearoyl lactylate, laureth-6 citrate and sodium PEG-4 lauramide carboxylate; ether carboxylic acids, for example sodium laureth-13 carboxylate and sodium PEG-6 cocamide carboxylate; phosphoric acid esters and salts, such as for example DEA-oleth-10 phosphate and dilaureth-4 phosphate; sulphonic acids and salts, such as acyl isethionates, for example sodium/ammonium cocoyl isethionate; alkyl aryl sulphonates; alkyl sulphonates, for example sodium cocomonoglyceride sulphonate, sodium C12-14 olefin sulphonate, sodium lauryl sulphoacetate and magnesium PEG-3 cocamide sulphate; sulphosuccinates, for example dioctyl sodium sulphosuccinate, disodium laureth sulphosuccinate, disodium lauryl sulphosuccinate and disodium undecylenamido MEA-sulphosuccinate; and sulphuric acid esters, such as alkyl ether sulphate, for example sodium, ammonium, magnesium, MIPA, TIPA laureth sulphate, sodium myreth sulphate and sodium C12-13 pareth sulphate, and alkyl sulphates, for example sodium, ammonium and TEA lauryl sulphate.

Cationic surfactants that can advantageously be used include: alkyl amines, alkyl imidazoles, ethoxylated amines and quaternary surfactants.

Quaternary surfactants contain at least one N atom that is covalently bonded to four alkyl or aryl groups. This leads to a positive charge, irrespective of the pH value. Alkyl betaine, alkyl amidopropyl betaine and alkyl amidopropyl hydroxysulphaine are advantageous. The cationic surfactants used can also preferably be chosen from the group of quaternary ammonium compounds, in particular benzyl trialkyl ammonium chlorides or bromides, such as for example benzyl dimethylstearyl ammonium chloride, as well as alkyl trialkyl ammonium salts, for example cetyl trimethyl ammonium chloride or bromide, alkyl dimethyl hydroxyethyl ammonium chlorides or bromides, dialkyl dimethyl ammonium chlorides or bromides, alkyl amide ethyl trimethyl ammonium ether sulphates, alkyl pyridinium salts, for example lauryl or cetyl pyridinium chloride, imidazoline derivatives and compounds of a cationic nature, such as amine oxides, for example alkyl dimethyl amine oxides or alkyl aminoethyl dimethyl amine oxides. Cetyl trimethyl ammonium salts can particularly advantageously be used.

Amphoteric surfactants that can advantageously be used include: acyl/dialkyl ethylene diamine, for example sodium acyl amphoacetate, disodium acyl amphodipropionate, disodium alkyl amphodiacetate, sodium acyl amphohydroxypropyl sulphonate, disodium acyl amphodiacetate and sodium acyl amphopropionate; N-alkyl amino acids, for example aminopropyl alkyl glutamide, alkyl aminopropionic acid, sodium alkyl imidodipropionate and lauroamphocarboxyglycinate.

Non-ionic surfactants that can advantageously be used include: alcohols; alkanolamides, such as cocamides MEA/DEA/MIPA, amine oxides, such as cocoamidopropylamine oxide; esters formed by esterification of carboxylic acids with ethylene oxide, glycerol, sorbitan or other alcohols; ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkyl polyglycosides, such as lauryl glucoside, decyl glycoside and cocoglycoside; sucrose esters and ethers; polyglycerol esters, diglycerol esters, monoglycerol esters; methyl glucose esters, ester of hydroxy acids.

The use of a combination of anionic and/or amphoteric surfactants with one or more non-ionic surfactants is also advantageous. The surface-active substance can be present in a concentration of between 1 and 98% (m/m) in the preparations containing histamine-release inhibitors in accordance with the invention, based on the dry weight of the preparations.

The composition or oat extract or cosmetic or pharmaceutical preparations that contain a composition or an oat extract according to the present invention can also be formulated in a form suitable for topical application, for example as lotions, aqueous or aqueous-alcoholic gels, vesicle dispersions or as simple or complex emulsions (O/W, W/O, O/W/O or W/O/W), liquids, semi-liquids or solids, such as milks, creams, gels, cream-gels, pastes or sticks, and can optionally be packaged as an aerosol and take the form of mousses or sprays. These compositions are prepared according to usual methods.

For preparing emulsions, the oil phase can advantageously be chosen from the following group of substances: mineral oils, mineral waxes; fatty oils, fats, waxes and other natural and synthetic fatty bodies, preferably esters of fatty acids with alcohols having a low C number, for example with isopropanol, propylene glycol or glycerol, or esters of fatty alcohols with alkanoic acids having a low C number or with fatty acids; alkyl benzoates; silicone oils such as dimethyl polysiloxanes, diethyl polysiloxanes, diphenyl polysiloxanes and mixed forms thereof. Advantageously, esters of saturated and/or unsaturated, branched and/or straight-chain alkane carboxylic acids having a chain length of 3 to 30 C atoms and saturated and/or unsaturated, branched and/or straight-chain alcohols having a chain length of 3 to 30 C atoms, from the group of esters of aromatic carboxylic acids and saturated and/or unsaturated, branched and/or straight-chain alcohols having a chain length of 3 to 30 C atoms can be used. Preferred ester oils include isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of such esters, for example jojoba oil.

The oil phase can also advantageously be chosen from the group comprising branched and straight-chain hydrocarbons and waxes, silicone oils, dialkyl ethers, the group comprising saturated or unsaturated, branched or straight-chain alcohols, and fatty acid triglycerides, specifically triglycerol esters of saturated and/or unsaturated, branched and/or straight-chain alkane carboxylic acids having a chain length of 8 to 24, in particular 12 to 18 C atoms. The fatty acid triglycerides can for example advantageously be chosen from the group comprising synthetic, semi-synthetic and natural oils, for example olive oil, sunflower oil, soybean oil, peanut oil, rapeseed oil, almond oil, palm oil, coconut oil, palm kernel oil and the like. Arbitrary admixtures of such oil and wax components can also advantageously be used. In some cases, it is also advantageous to use waxes, for example cetyl palmitate, as the sole lipid component of the oil phase; the oil phase is advantageously chosen from the group consisting of 2-ethylhexyl isostearate, octyldodecanol, isotridecyl isononanoate, isoeicosane, 2-ethylhexyl cocoate, C12-15 alkyl benzoate, caprylic-capric acid triglyceride and dicaprylyl ether. Mixtures of C12-15 alkyl benzoate and 2-ethylhexyl isostearate, mixtures of C12-15 alkyl benzoate and isotridecyl isononanoate and mixtures of C12-15 alkyl benzoate, 2-ethylhexyl isostearate and isotridecyl isononanoate are particularly advantageous. The hydrocarbons paraffin oil, squalane and squalene can also advantageously be used. The oil phase can advantageously also contain or consist entirely of cyclic or linear silicone oils, although an additional content of other oil phase components in addition to the silicone oil or oils is preferably used. Cyclomethicone (for example, decamethylcyclopentasiloxane) can advantageously be used as the silicone oil. However, other silicone oils can also advantageously be used, such as for example undecamethylcyclotrisiloxane, polydimethylsiloxane and poly(methylphenylsiloxane). Mixtures of cyclomethicone and isotridecyl isononanoate and of cyclomethicone and 2-ethylhexyl isostearate are also particularly advantageous.

The aqueous phase of preparations that contain the composition or oat extract according to the present invention and are provided in the form of an emulsion can include: alcohols, diols or polyols having a low C number, and their ethers, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, as well as alcohols having a low C number, such as ethanol, isopropanol, 1,2-propanediol, glycerol and in particular one or more thickeners, which can advantageously be chosen from the group comprising silicon dioxide, aluminium silicates, polysaccharides and their derivatives, such as hyaluronic acid, xanthan gum, hydroxypropyl methyl cellulose, and particularly advantageously from the group comprising polyacrylates, preferably a polyacrylate from the group comprising so-called carbopols, such as type 980, 981, 1382, 2984, 5984 carbopols, each on their own or in combinations.

The composition or oat extract or cosmetic or pharmaceutical preparations that contain a composition or an oat extract according to the present invention and are provided in the form of an emulsion advantageously contain one or more emulsifiers commonly used in the art for preparing cosmetic or pharmaceutical preparations.

The composition or oat extract or cosmetic or pharmaceutical preparations containing a composition or an oat extract according to the present invention may also include a cosmetically or pharmaceutically acceptable carrier, such as (without being limited to) one of the following which are commonly used in the art: lactose, dextrose, sucrose, sorbitol, mannitol, starch, acacia rubber, calcium phosphate, alginate, gelatine, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oil and the like. The cosmetic or pharmaceutical preparations may also include lubricants, wetting agents, sweeteners, flavouring agents, emulsifiers, suspensions, preserving agents and the like, in addition to the above components. Suitable pharmaceutically acceptable carriers and preparations are described in detail in Remington's Pharmaceutical Sciences ($19^{th}$ edition, 1995).

The pharmaceutical preparation may be administered orally or parenterally. If administered parenterally, the pharmaceutical composition may be administered by intravenous injection, subcutaneous injection, intramuscular injection, intraperitoneal injection, local administration, dermal administration, nasal administration or the like.

A suitable dosage of the pharmaceutical preparation according to the present invention may be variously prescribed depending on factors such as method of formulation, age, body weight, gender or morbid condition, food, administration time, administration route, excretion rate and reaction sensitivity of the patient.

The pharmaceutical composition according to the present invention may be manufactured in a unit dosage form, by being formulated using the pharmaceutically acceptable carrier and/or excipient according to a method that can be easily executed by an average person skilled in the art to which the present invention pertains.

The present invention shall now be described in detail with reference to the following examples, which are merely illustrative of the present invention, such that the content of the present invention is not limited by or to the following examples.

EXAMPLES

Examples of the present invention are described below. The invention should not however be construed as being limited to the examples detailed.

Example 1: Extraction of Milled and Non-Milled Naked Oat (*Avena nuda*) Grains Plant materials are typically milled, crushed or cut into small pieces to allow for more exhaustive extraction. The extraction of milled and non-milled naked oat grains was therefore compared.

100 grams of organic naked oat grains (the Salomon cultivar, bought from Bohlenser Mühle and cultivated in Germany), either as such or milled, was extracted using 300 grams of 50% aqueous ethanol (w/w) for 2 hours at 60° C. with stirring. The mixture was cooled to room temperature, and the grains were separated from the extract solution by centrifugation and filtration. The extracting solvents were removed by vacuum using an evaporator, and the dry extracts obtained were weighed to determine the extraction yields.

Avns were quantified in the dry extract by HPLC using an acetonitrile/water/0.1% formic acid gradient on an ODS-AQ column (YMC) at 330 nm, and β-glucan and monomeric glucose were quantified using a β-glucan assay kit (mixed-linkage) of Megazyme in accordance with the supplier's instructions.

This assay kit is specific for mixed-linkage (1→3, 1→4) β-glucan as occurring in cereals such as oats, barley and derived products such as e.g. oat fibre products, malt and beer.

Assay principle: Samples are suspended and hydrated in a buffer solution of pH 6.5 and then incubated with purified lichenase enzyme and filtered. An aliquot of the filtrate is then hydrolyzed to completion with purified β-glucosidase. The D-glucose produced is determined afterwards using a glucose oxidase/peroxidase reagent.

TABLE 2

Characterisation of naked oat extracts

| Extract | Dry extract yield* [wt %] | Content: Avn C [ppm] | Avn A [ppm] | Avn B [ppm] | Total of Avns A to C [ppm] | Avn L [ppm] | Glucose [wt %] | β-Glucan [wt %] |
|---|---|---|---|---|---|---|---|---|
| Whole (non-milled) grains | 2.1 | 1176 | 2308 | 2416 | 5900 | n.d. | 0.21 | 0.91 |
| Milled grains | 4.5 | 627 | 1087 | 1377 | 3091 | n.d. | 0.33 | 2.21 |

*Based on oat grains
n.d. = not determined

The results show that the aqueous ethanolic extract obtained from whole (non-milled) grains contains a 1.9-fold higher total content of Avns A to C (5900 ppm versus 3091 ppm) than the extract obtained from milled grains. By contrast, the β-glucan content of the aqueous ethanolic extract from milled grains is 2.4 times higher than in the extract from whole (non-milled) grains. Extraction of non-milled, whole naked oat grains has the additional benefit that it allows much easier, faster and thus cheaper separation of the plant material from the extract solution after extraction.

Example 2: Extraction of Milled and Non-Milled Common Oat (*Avena sativa*) Grains 50 grams of common oat grains (the Max cultivar, cultivated in Germany), either as such or milled, was extracted using 300 grams of 50% aqueous ethanol (w/w) for 2 hours at different temperatures with stirring. The mixture was cooled to room temperature, and the grains were separated from the extract solution by centrifugation and filtration. The extracting solvents were removed by vacuum using an evaporator, and the dry extracts obtained were weighed to determine the extraction yields. Avns were quantified in the dry extracts as described in Example 1.

TABLE 3

Characterisation of common oat extracts extracted at different temperatures

| Extract | Extraction temperature [° C.] | Dry extract yield* [wt %] | Content: Avn C [ppm] | Avn A [ppm] | Avn B [ppm] | Total of Avns A to C [ppm] | Avn L [ppm] |
|---|---|---|---|---|---|---|---|
| Milled grains | 40 | 3.5 | 454 | 505 | 921 | 1880 | n.d. |
| Milled grains | 50 | 3.8 | 541 | 531 | 906 | 1978 | n.d. |
| Milled grains | 60 | 3.8 | 549 | 555 | 952 | 2056 | n.d. |

TABLE 3-continued

Characterisation of common oat extracts extracted at different temperatures

| Extract | Extraction temperature [° C.] | Dry extract yield* [wt %] | Content | | | | |
|---|---|---|---|---|---|---|---|
| | | | Avn C [ppm] | Avn A [ppm] | Avn B [ppm] | Total of Avns A to C [ppm] | Avn L [ppm] |
| Milled grains | 70 | 4.4 | 519 | 508 | 867 | 1894 | n.d. |
| Whole (non-milled) grains | 60 | 1.0 | 1038 | 1238 | 1880 | 4157 | n.d. |

*Based on oat grains
n.d. = not determined

The results show that for milled oat grains, extraction yield increases with increasing temperature from 3.5% at 40° C. up to 4.4% at 70° C. The total content of Avns A to C increases in parallel from 1880 ppm at 40° C. to 2056 ppm at 60° C., but then decreases to 1894 ppm at 70° C. Thus, based on the yield and Avn content, the extraction of milled common oats at temperatures between 50 and 60° C. gives the best results.

Extraction of non-milled common oat grains at the most suitable temperature of 60° C. resulted in the dry extract having a 2.0-fold higher content of Avns A to C than the extract obtained from milled oat grains.

Example 3: Preparation of an Extract Fraction of *Avena nuda* (Naked Oat) Grains Containing Avns and β-Glucan 1000 grams of non-milled organic naked oat grains (bought from Bohlenser Mühle and cultivated in Germany; the same batch as used in Example 1) was extracted using 2000 grams of 50% aqueous ethanol (w/w) for 2 hours at 60° C. with stirring. The mixture was cooled to room temperature, and the grains were separated from the extract solution by centrifugation and filtration. The extracted grains were extracted a second time using another 1500 grams of 50% aqueous ethanol (w/w) for 2 hours at 60° C. with stirring, and the extract solution was separated as described above. The extract solutions of the two extractions were combined, to give 2700 grams. The dry-matter content and extraction yield was determined by removing the extracting solvents by vacuum using an evaporator from a 118-gram aliquot, resulting in 1.57 grams of dry extract, corresponding to a dry extract yield of 3.6 wt %.

Ethanol was removed from the rest of the extract solution by vacuum using an evaporator, to give 900 grams of aqueous extract solution. The dry-matter content of the resulting aqueous extract solution was determined, and 100 grams of water was added, to give 1000 grams of a 3.0 wt % solution. The pH value was adjusted to 3.0 using hydrochloric acid, and the precipitate formed was removed by centrifugation.

250 grams of Lewatit® VP OC 1064 MD PH resin (Lanxess), washed in accordance with the supplier's instructions and conditioned in water, was filled into a 4 cm diameter open glass column, and the aqueous extract solution was submitted to it. The solution was passed through the column at a gravity-induced flow. The column was then washed with 300 grams of water, and excess water was removed by vacuum or by blowing nitrogen through the resin. The adsorbed extract ingredients were then eluted from the resin using 600 grams of ethanol.

The water filtrate and washing water were combined and lyophilised, to obtain 20 grams of dry water fraction, corresponding to a yield of 2.0 wt % based on oat grains.

The ethanol was removed from the ethanolic eluate by vacuum, to obtain 7.5 grams of dry ethanol fraction, corresponding to a yield of 0.8 wt % based on oat grains.

The dried extract fractions were characterised as described in Example 1.

TABLE 4

Characterisation of naked oat extract and extract fractions

| Extract | Dry extract yield* [wt %] | Content | | | | | | |
|---|---|---|---|---|---|---|---|---|
| | | Avn C [ppm] | Avn A [ppm] | Avn B [ppm] | Total of Avns A to C [ppm] | Avn L [ppm] | Glucose [wt %] | β-Glucan [wt %] |
| Dried aqueous ethanol extract | 3.6 | 837 | 1482 | 1815 | 4134 | n.d. | 0.16 | 1.05 |
| Dried water filtrate | 2.0 | 105 | 148 | 226 | 478 | n.d. | 1.58 | 0.71 |
| Dried ethanol eluate | 0.8 | 4840 | 7862 | 9537 | 22239 | n.d. | 0.17 | 2.79 |

*Based on oat grains
n.d. = not determined

The results show that the dried ethanol eluate fraction contains a 5.4-fold higher content of Avns (total Avns A to C content of 22239 ppm versus 4134 ppm) than the dried aqueous ethanol extract.

Surprisingly, the dried ethanol eluate fraction also contains a 2.7-fold higher content of β-glucan than the dried aqueous ethanol extract, and a 3.9-fold higher content than the dried water filtrate fraction, even though β-glucans are water-soluble. With a total Avns A to C content of 2.2 wt %

(22239 ppm) and 2.8 wt % of β-glucan, the dried ethanol eluate fraction interestingly contains a very similar content of both substance classes in the same extract fraction.

The dried aqueous ethanolic extract and the dried ethanol eluate fraction were also analysed for their content of cations and anions by ion chromatography, and for free amino acids by HPLC with after-column ninhydrin derivatisation.

TABLE 5

Content of cations, anions and free amino acids in an aqueous ethanol extract and an ethanol eluate fraction

| | Content wt % | |
|---|---|---|
| Analyte | Dried aqueous ethanol extract | Dried ethanol eluate fraction |
| $Na^+$ | 0.01 | 0.01 |
| $K^+$ | 2.06 | 0.01 |
| $Mg^{2+}$ | 0.09 | 0.01 |
| $Ca^{2+}$ | 0.06 | 0.02 |
| Chloride | 0.47 | 0.15 |
| Sulphate | 2.00 | 0.01 |
| Phosphate | 0.69 | 0.02 |
| Total free amino acids, including: | 2.44 | 0.60 |
| Aspartic acid | 0.1035 | 0.0019 |
| Threonine | 0.0442 | 0.0012 |
| Serine | 0.0616 | 0.0014 |
| Asparagine | 0.7728 | 0.0135 |
| Glutamic acid | 0.3687 | 0.0090 |
| Glycine | 0.0518 | 0.0013 |
| Alanine | 0.1326 | 0.0020 |
| Isoleucine | 0.0245 | 0.0073 |
| Leucine | 0.0251 | 0.0140 |
| Tyrosine | 0.0371 | 0.0267 |
| Phenylalanine | 0.0236 | 0.0892 |
| Alanine, β- | 0.0746 | 0.0198 |
| Tryptophan, 5-Hydroxy | 0.0587 | 0.0008 |
| Lysine | 0.0641 | 0.0018 |
| Tryptophan | 0.0858 | 0.3695 |
| Arginine | 0.1876 | 0.0050 |
| Proline | 0.4873 | 0.0248 |

The results show that the content of salts in the dried ethanol eluate fraction is much lower than that of the dried aqueous ethanol extract, as can be seen from the cations and anions determined (0.24% versus 5.40% in total).

This has two advantages. On the one hand, oil-in-water (o/w) emulsions are the most popular type of over-the-counter personal care emulsions. In such emulsions, the external phase is aqueous, including water and water-soluble components, and the internal phase comprises oil and oil-soluble components. High concentrations of ionised materials (cations and anions) in solution can destabilise the emulsion interface. In fact, adding salt to emulsified materials is a common strategy used in water treatment plants to destabilise emulsions and separate or purify the materials therein. Lowering the salt content can therefore be considered to be beneficial to emulsion stability.

On the other hand, metal ions have a powerful influence on chemical processes and on the performance of many products, as they can for example catalyse the degradation of ingredients used in personal care products. Lowering the content of metal cations can therefore be considered to be beneficial to product and ingredient stability.

The results also show that the dried ethanol eluate fraction contains four times less total free amino acids than the dried aqueous ethanol extract (2.44 versus 0.60%). Interestingly, however, the dried ethanol eluate fraction contains 3.8 times more phenylalanine and 4.3 times more tryptophan than the dried aqueous ethanol extract.

Example 4: ABTS Assay

Since Avns and β-glucan are known to exhibit anti-oxidant efficacy, the radical-scavenging activity of the extract and extract fractions obtained in Example 3 was determined using an ABTS assay.

The anti-oxidative capacity of test substances was measured with the aid of the ABTS assay. 2,2'-azino-bis(3-ethylbenzothiazoline-6-sulphonic acid) (ABTS) was transformed by potassium persulphate into the blue-green radical cation ABTS•+. The radical cations were reduced through the addition of antioxidants (test substances), and discoloration took place which was determined photometrically at 734 nm.

$$\text{Inhibition}[\%] = 100 - \left(\frac{A\ \text{test substance}}{A\ \text{control}} \times 100\right)$$

where A test substance means absorption of the wells with the test substance and A control means absorption of the wells without the test substance.

The IC50 was calculated from the inhibition of radical formation [%] in a series of dilutions of tested samples. This is the concentration at which radical formation is inhibited by 50%. The results are shown in Table 6.

TABLE 6

Activity based on the inhibition of radical formation (mean value from at least two independent tests)

| Test sample | IC50 [wt %] | Radical-scavenging activity at 0.005 wt % |
|---|---|---|
| Dried aqueous ethanol extract (Example 3) | 0.0130 | 48% |
| Dried water filtrate (Example 3) | 0.0210 | 22% |
| Dried ethanol eluate (Example 3) | 0.0023 | 98% |

Comparison of the IC50 values shows that the dried ethanol eluate fraction is 5.7 times more active than the dried aqueous ethanol extract and 9.1 times more active than the dried water filtrate fraction.

Example 5: Preparation of an Extract Fraction of *Avena nuda* (Naked Oat) Grains Containing Avns and β-Glucan—Comparing pH 3.0 and Non-Adjusted pH 501 grams of non-milled organic naked oat grains (the Salomon cultivar, bought from Bohlenser Mühle and cultivated in Germany; a different batch to that used in Examples 1 or 3) was extracted using 800 grams of 50% aqueous ethanol (w/w) for 2 hours at 60° C. with stirring and extracted twice as described in Example 3. The extract solutions of the two extractions were combined, to give 1070 grams. The dry-matter content and extraction yield was determined by removing the extracting solvents by vacuum using an evaporator from a 115-gram aliquot, resulting in 1.54 grams of dry extract, corresponding to a dry extract yield of 2.9 wt %.

The remaining extract solution was divided into two parts. In the first part: (A) The ethanol was removed from 485 grams of it (6.5 grams of dry extract) by vacuum using an evaporator, to give 130 grams which were diluted by adding water to give 500 grams of aqueous extract solution (1.3 wt % dry matter). The pH value was then adjusted to 3.0 by means of hydrochloric acid.

250 grams of Lewatit® VP OC 1064 MD PH resin (Lanxess), washed in accordance with the supplier's instructions and conditioned in water, was filled into a 4 cm diameter glass column, and the pH-adjusted aqueous extract solution was submitted to it. The solution was passed through the column at a gravity-induced flow. The filtrate obtained was re-submitted onto the column twice. The column was then washed with 200 grams of water, and excess water was removed by vacuum or by blowing nitrogen through the resin. The adsorbed extract ingredients were then eluted from the resin using 600 grams of ethanol.

The water filtrate and washing water were combined and lyophilised, to obtain 4.0 grams of dry water fraction, corresponding to a yield of 1.8 wt % based on oat grains.

The ethanol was removed from the ethanolic eluate by vacuum, to obtain 2.1 grams of dry ethanol fraction, corresponding to a yield of 1.0 wt % based on oat grains.

In the second part: (B) Another 485 grams of it (6.5 grams of dry extract) was treated as described in (A), to give 500 grams of aqueous extract solution (1.3 wt % dry matter). The pH value of this solution was 6.4 and was not adjusted.

250 grams of Lewatit® VP OC 1064 MD PH resin (Lanxess), washed in accordance with the supplier's instructions and conditioned in water, was filled into a 4 cm diameter glass column, and the aqueous extract solution was submitted to it with no pH adjustment. Adsorption and elution were performed as described in (A).

The water filtrate and washing water were combined and lyophilised, to obtain 4.4 grams of dry water fraction, corresponding to a yield of 2.0 wt % based on oat grains.

The ethanol was removed from the ethanolic eluate by vacuum, to obtain 2.0 grams of dry ethanol fraction, corresponding to a yield of 0.9 wt % based on oat grains.

The dried extract and ethanol eluate fractions were characterised as described above, and the results are summarised in Table 7.

TABLE 7

| Extract | Dry extract yield* [wt %] | Content: Avn C [ppm] | Avn A [ppm] | Avn B [ppm] | Total of Avns A to C [ppm] | Avn L [ppm] | Glucose [wt %] | β-Glucan [wt %] |
|---|---|---|---|---|---|---|---|---|
| Dried aqueous ethanol extract | 2.9 | 619 | 1233 | 1511 | 3363 | n.d. | 0.29 | 1.22 |
| (A) Dried ethanol eluate (pH 3.0) | 1.0 | 1753 | 3390 | 4003 | 9146 | n.d. | 0.63 | 2.36 |
| (B) Dried ethanol eluate (no pH adjustment) | 0.9 | 1922 | 3864 | 4758 | 10544 | n.d. | 0.19 | 2.21 |

*Based on oat grains
n.d. = not determined

The results show that both dried ethanol eluate fractions exhibit a higher content of Avns as compared to the dried aqueous ethanol extract. The dried ethanol eluate fraction obtained from the aqueous extract solution with no pH adjustment, and the dried ethanol eluate fraction obtained from the aqueous extract solution having a pH of 3, contains a 3.1-fold and 2.7-fold higher total content of Avns A to C (10544 and 9146 ppm versus 3363 ppm), respectively.

The dried ethanol eluate fraction obtained from the aqueous extract solution with no pH adjustment, however, contains a 20% (1.2-fold) higher total content of Avns A to C as compared to the one obtained with adjustment to pH 3 (10544 versus 9146 ppm).

Surprisingly, the dried ethanol eluate fraction also contains a 1.9-fold (A) and 1.8-fold (B) higher content of β-glucan than the dried aqueous ethanol extract, even though β-glucans are water-soluble.

With a total content of Avns A to C of 1.05 wt % (10544 ppm) and 2.21 wt % of β-glucan, the dried ethanol eluate fraction obtained from the aqueous extract solution with no pH adjustment (A) interestingly contains both substance classes at a similar content to the dried ethanol eluate fraction obtained at pH 3.0 (B).

In addition to the above experiments, the preparation of a solution containing a total of approximately 500 parts per million of Avns A to C was investigated. 2 grams of 1,3-propanediol were added to 109 milligrams of dried ethanol eluate fraction obtained from (A) and (B), respectively, to give red-brownish solutions which are easy to use and handle, for example in cosmetic preparations.

The antioxidant capacity of the two ethanol dried ethanol eluate fractions was determined using the ABTS assay described in Example 4. The results are shown in Table 8.

TABLE 8

Activity based on the inhibition of radical formation (mean value from at least two independent tests)

| Test sample | IC50 [wt %] | Radical-scavenging activity at 0.005 wt % |
|---|---|---|
| (A) Dried ethanol eluate (pH 3.0) | 0.0033 | 76% |
| (B) Dried ethanol eluate (no pH adjustment) | 0.0033 | 78% |

Comparison of the IC50 values shows that both dried ethanol eluate fractions exhibit comparable anti-oxidant capacity.

Example 6: Preparation of an Extract Fraction of *Avena nuda* (Naked Oat) Grains Containing Avns and β-Glucan—Comparing Extracts from Whole (Non-Milled) and Milled Grains (No pH Adjustment)

500 grams of non-milled organic naked oat grains (bought from Bohlenser Mühle and cultivated in Germany; a different batch to that used in Examples 1, 3 or 5) was extracted using 1200 grams of 50% aqueous ethanol (w/w) for 2 hours at 60° C. with stirring and extracted twice as described in Example 3. The extraction yield was determined as described in Example 5, resulting in an extraction yield of 2.8 wt %.

The ethanol was removed from the aqueous ethanolic extract solution, and additional water was added, to obtain an aqueous extract solution with a dry-matter content of approximately 1 wt %, as described in Example 5.

250 grams of Lewatit® VP OC 1064 MD PH resin (LANXESS) washed in accordance with the supplier's instructions and conditioned in water, was filled into a 4 cm diameter glass column, and the aqueous extract solution (non-adjusted in its pH value) was submitted to it. The solution was passed through the column at a flow of 100 ml/min. The filtrate obtained was re-submitted onto the column twice. Washing with water and elution with ethanol was performed as described in Example 5.

The yield, based on oat grains, of the water filtrate and ethanol eluate was determined by drying and found to be 2.0 and 0.7 wt %, respectively.

The entire process was repeated with milled grains: 0.6 grams of the dried ethanol eluate obtained from the extract of whole (non-milled) grains was dissolved in 49 grams of a 1:1 (wt/wt) mixture of glycerol and water at 30° C. with stirring. The content of Avns was then determined by HPLC.

The dried extracts, dried extract fractions and the glycerol/water solution were characterised as described above, and the results are summarised in Table 9.

TABLE 9

| Extract | Dry extract yield* [wt %] | Content Avn C [ppm] | Avn A [ppm] | Avn B [ppm] | Total of Avns A to C [ppm] | Avn L [ppm] | Glucose [wt %] | β-Glucan [wt %] |
|---|---|---|---|---|---|---|---|---|
| Whole (non-milled grains) | | | | | | | | |
| Dried aqueous ethanol extract | 2.7 | 484 | 804 | 1434 | 2722 | 256 | 0.27 | 0.96 |
| Dried water filtrate | 2.0 | <10 | <10 | <10 | <10 | <10 | 0.14 | 0.25 |
| Dried ethanol eluate | 0.7 | 1344 | 2651 | 4316 | 8311 | 792 | 0.29 | 2.08 |
| Glycerol/water solution of the dried ethanol eluate | — | 18 | 35 | 59 | 113 | 10 | n.d. | n.d. |
| Milled grains | | | | | | | | |
| Dried aqueous ethanol extract | 6.1 | 333 | 514 | 874 | 1721 | 143 | 0.11 | 0.65 |
| Dried water filtrate | 4.5 | 315 | 481 | 756 | 1552 | 48 | 0.19 | 0.67 |
| Dried ethanol eluate | 1.2 | 222 | 608 | 1104 | 1934 | 342 | 0.12 | 0.67 |

*Based on oat grains
n.d. = not determined

The results clearly show that the adsorption step does not provide the expected enrichment of either Avns or β-glucan when performed on the extract obtained using milled grains. Ingredients from the inner part of the oat grains which are co-extracted interfere with adsorption and thereby obstruct fractionation and Avns enrichment.

The dried ethanol eluate fraction obtained from the extract of whole (non-milled) grains again contains a 3.1-fold higher total content of Avns A to C (8311 ppm versus 2722 ppm), a 3.1-fold higher content of Avn L (792 ppm versus 256 ppm) and a 2.2-fold higher content of β-glucan (2.08 versus 0.96%).

Example 7: Scale-Up 500 kilos (kilograms) of non-milled organic naked oat grains (the Oliver cultivar, bought from Bohlenser Mühle and cultivated in Germany; a different batch to that used in Examples 1, 3, 5 or 6) was extracted using a mixture of 860 kilos of ethanol (96.5 vol %) and 800 kg of water for 2 hours at 55 to 60° C. After separation of the extract solution, extraction of the extracted oat grains was repeated using the same amounts of ethanol and water. After separation of the extract solution from the extracted grains, the two extract solutions were combined, and the extraction yield was determined as described in Example 5, by drying an aliquot, and found to be 2.6 wt %.

The ethanol was removed from the aqueous ethanolic extract solution by vacuum distillation, and additional water was added, to obtain an aqueous extract solution with a dry-matter content of approximately 0.5 to 1.0 wt %.

The aqueous extract solution obtained (having a non-adjusted pH value) was submitted to a 20-litre steel column filled with Lewatit® VP OC 1064 MD PH resin (Lanxess), washed in accordance with the supplier's instructions and conditioned in water. The solution was passed through the column at a flow of 10 to 5 l/min. Residual water was then removed from the column by vacuum or by blowing nitrogen through it, and 140 kilos of ethanol (96.5 vol %) was used to elute the adsorbed extract ingredients.

The yield, based on oat grains, of the ethanol eluate was determined by drying an aliquot and found to be 0.2 wt %.

The dried ethanol eluate was analysed by HPLC-DAD-MS measurement using an acetonitrile/water/0.1% formic acid gradient on an ODS-AQ column (YMC) (AmazonSL ion trap in positive and negative ion mode) for Avns. The results are summarized in Table 10.

Figure 3:
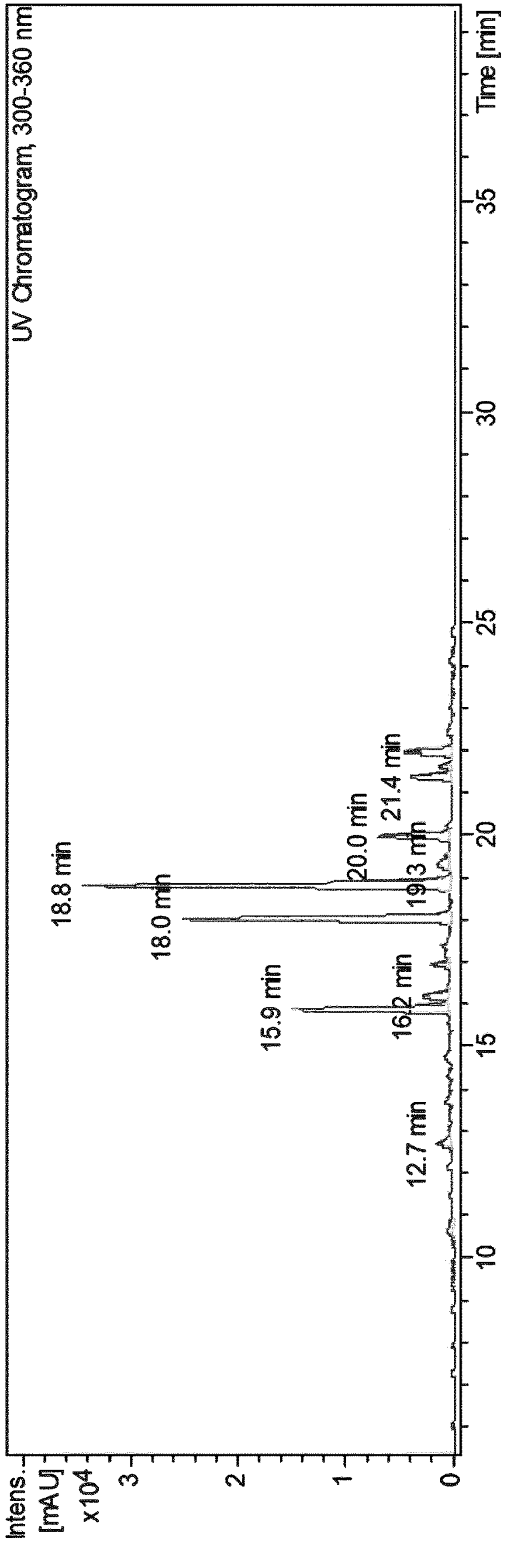
FIG. 3 is a HPLC-chromatogram of the dried ethanol eluate of Example 7.

The HPLC-chromatogram of the dried ethanol eluate at 300-360 nm is represented in FIG. 3.

TABLE 10

| Rt [min] | ESI neg | Molecular weight [g/mol] | ESI pos Avn Fragment | Cinnamic acid part of the Avn | Calculated anthranilic acid fragment | Anthranilic acid part of the Avn | Avn* |
|---|---|---|---|---|---|---|---|
| 14.3 | 330 | 331 | 163 | Caffeic acid | 168 | 4,5-Di-OH-anthranilic acid | Avn CC |
| 15.9 | 314 | 315 | 163 | Caffeic acid | 152 | 5-OH-anthranilic acid | Avn C |
| 16.3 | 314 | 315 | 147 | p-Coumaric acid | 168 | 4,5-Di-OH-anthranilic acid | Avn AA |
| 18.1 | 298 | 299 | 147 | p-Coumaric acid acid | 152 | 5-OH-anthranilic acid | Avn A |
| 18.8 | 328 | 329 | 177 | Ferulic acid | 152 | 5-OH-anthranilic acid | Avn B |
| 19.2 | 328 | 329 | 147 | p-Coumaric acid | 182 | 4-OMe-5-OH-anthranilic acid | Avn X |
| 19.4 | 340 | 341 | 173 | Avenalumic acid | 168 | 4,5-Di-OH-anthranilic acid | Avn OO |
| 19.6 | 298 | 299 | 147 | p-Coumaric acid | 152 | 5-OH-anthranilic acid | Avn G |
| 20.0 | 358 | 359 | 177 | Ferulic acid | 182 | 4-OMe-5-OH-anthranilic acid | Avn 2** (Y*) |
| 20.3 | 328 | 329 | 177 | Ferulic acid | 152 | 5-OH-anthranilic acid | Avn H |
| 21.4 | 324 | 325 | 173 | Avenalumic acid | 152 | 4-OH-anthranilic acid | Avn L** (O*) |
| 21.6 | 298 | 299 | 163 | Caffeic acid | 136 | Anthranilic acid | Avn F |
| 22.0 | 324 | 325 | 173 | Avenalumic acid | 152 | . . . -OH-anthranilic acid | Avn L isomer |
| 22.4 | 354 | 355 | 173 | Avenalumic acid | 182 | 4-OMe-5-OH-anthranilic acid | Avn U |
| 24.2 | 282 | 283 | 147 | p-Coumaric acid | 136 | Anthranilic acid | Avn D |
| 24.9 | 312 | 313 | 177 | Ferulic acid | 136 | Anthranilic acid | Avn E |

*Abbreviations Collins [de Bruijn et al., Food Chemistry (2018), https://doi.Org/10.1016/j.foodchem.2018.11.013, supplementary information Table S1]
**Other common name, non-Collins abbreviations Glycerol and water are common cosmetic solvents, such that directly adding glycerol and water to the ethanol eluate solution and then removing the ethanol is a simple, less time-consuming and less energy-consuming way of preparing a glycerol/water-based solution.

Glycerol at 99.5% and water were added to the ethanol eluate solution, and the ethanol was removed from the mixture by vacuum distillation. Potassium sorbate was then added, and the mixture was adjusted to between pH 4.5 and pH 3.5 by means of lactic acid, for preservative purposes. A 1% oat extract solution in a mixture of 50 wt % water, 48.8 wt % glycerol and 0.2 wt % potassium sorbate was thus obtained. Finally, the solution was filtered over a filter plate, to give a clear-to-slightly-turbid liquid. This provides an easy-to-use, cosmetically accepted product which is easy to formulate in common cosmetic preparations.

The dried extract, dried ethanol eluate fraction and the glycerol/water solution were characterised as described above, and the results are summarised in Table 11.

The results clearly show that the adsorption step provides the expected enrichment of Avns to 16020 parts per million of Avns A to C when performed at a production scale, even though the oat used contained relatively low amounts of Avns, as can be seen from the content of Avns A to C of only 1614 ppm.

The β-glucan content was again also enriched, yielding an extract fraction after the adsorption step having a comparable content of Avns (1.60 wt %) and β-glucan (1.65 wt %).

The process was repeated using 250 kilos of a different batch of naked oat grains from the same supplier and retaining the ratio of oat grains to extracting solvents. A glycerol/water-based solution of the ethanol eluate fraction containing a total of 100 to 120 parts per million of Avns A to C was prepared, as described above, by adjusting the amount of glycerol and water to the dry-matter content of Avns in the ethanol eluate fraction. The results of the two extractions are compared in Table 12 below.

TABLE 11

| Extract | Dry extract yield* [wt %] | Content: Avn C [ppm] | Avn A [ppm] | Avn B [ppm] | Total of Avns A to C [ppm] | Avn L [ppm] | Glucose [wt %] | β-Glucan [wt %] |
|---|---|---|---|---|---|---|---|---|
| Dried aqueous ethanol extract | 2.9 | 268 | 622 | 724 | 1614 | 156 | 0.36 | 0.89 |
| Dried ethanol eluate | 0.2 | 2540 | 6262 | 7218 | 16020 | 1276 | 0.14 | 1.65 |
| Glycerol/water solution of the dried ethanol eluate | — | 20 | 47 | 49 | 116 | 9 | <0.01 | 0.02 |

*Based on oat grains

TABLE 12

| Amount of extracted oat grains | 500 kg | 250 kg |
|---|---|---|
| Extract yield based on dry matter | 2.6% | 2.6% |
| Total content of Avns A to C in the dried extract | 1614 ppm | 5758 ppm |
| Yield of the ethanol eluate fraction based on dry matter | 0.2% | 0.3% |
| Total content of Avns A to C in the dried ethanol eluate fraction | 16020 ppm | 45537 ppm |
| Enrichment factor - ethanol eluate:extract | 9.9 | 7.9 |
| Calculated amount of glycerol/water-based solution containing 120 parts per million of Avns A to C | 138 kg | 288 kg |
| Characteristics of the glycerol/water-based solution: | | |
| Relative density D20/4 | 1.1371 | 1.1319 |
| Refraction index n20/D | 1.4045 | 1.4018 |
| Colour (visual) | dark yellow | yellow-brown |
| Colour a* value (Lab colour system) | −1.20 | −6.80 |
| Colour b* value (Lab colour system) | 36.90 | 34.80 |
| pH value | 4.00 | 4.29 |

As can be seen from the above results, the enrichment of Avns obtained in the adsorption step is achieved efficiently with oat grain extracts of both low and high content of Avns A to C (1614 versus 5758 ppm).

The content of minerals was determined for the dry extracts and dried ethanol eluate fraction by IC, and the results are shown in Table 13.

TABLE 13

| | Extraction of | | | |
|---|---|---|---|---|
| | 500 kilos of oat grains | | 250 kilos of oat grains | |
| Analyte | Extract | Ethanol eluate | Extract | Ethanol eluate |
| $Na^+$ | 0.044 | 0.046 | 0.085 | 0.038 |
| $K^+$ | 2.99 | 0.094 | 3.32 | 0.22 |
| $Cl^-$ | 1.61 | 0.034 | 2.35 | 0.037 |
| $SO_4^{2-}$ | 0.12 | 0.043 | 0.32 | 0.022 |
| $PO_4^{3-}$ | 2.12 | 0.022 | 2.32 | 0.025 |

These results accord with the results given in Example 3. The reduction of minerals (cations and anions) observed is especially beneficial for application in preparations, since salts are known to reduce emulsion stability and cations are known to catalyse oxidative reactions.

Example 8: Liquid Solution of Oat Extract Fractions with 1,2-Pentanediol and Enriched Avn and β-Glucan An aliquot of 100 grams of the oat ethanol eluate obtained as described in Example 7, having a dry-matter content of 0.75 wt % and an Avns A to C content of 16020 ppm in the dry matter, was mixed with 50 grams of glycerol at 99.5%, 5 grams of 1,2-pentanediol (Hydrolite-5, Symrise) and 30 grams of water. The ethanol was removed by vacuum, and water was added to the resulting solution, to give 100 grams. The solution was filtered over a filter plate, yielding a slightly turbid yellow-brown liquid oat extract fraction with enriched Avns and β-glucan, characterised by a content of Avns A to C of 105 ppm (15 parts per million of Avn C, 43 parts per million of Avn A, 47 parts per million of Avn B), an Avn L content of 7 ppm, and 0.02% β-glucan.

Example 9: Stability Test of Different Avn-Containing Liquid Oat Extract Fraction Solutions The oxidative and light stability of the glycerol/water-based solutions of the ethanol eluate fraction obtained in Examples 7 and 8 having a comparable total content of Avns A to C and β-glucan was evaluated against a glycerol/water-based solution of an oat extract fraction obtained by membrane filtration (and thus with β-glucan removed; supplied by Ceapro).

The liquids were either exposed to 5 bars of oxygen for 24 hours at 70° C. using the Oxipress device or irradiated for 6 hours using a Xenotest 440 instrument (60 W, 1294 kJ/$m^2$, wavelength 300-400 nm).

The content of Avns was determined by HPLC, and the colour was measured by colorimetry (Hach Lange Lico 690 instrument) before and after treatment.

TABLE 14

| Oxidative stability (Oxipress) | | | | | | | |
|---|---|---|---|---|---|---|---|
| | Content | | | | Colour | | |
| | Avn C | Avn A | Avn B | Total of Avns A to C | | | |
| Sample | [ppm] | [ppm] | [ppm] | [ppm] | L* | a* | b* |
| Solution of ethanol eluate fraction, containing Avns and β-glucan, in glycerol/water as obtained in Example 7 | | | | | | | |
| Before treatment | 22 | 52 | 64 | 138 | 85.8 | −2.9 | 50.1 |
| After treatment | 14 | 51 | 62 | 127 | 81.2 | 2.1 | 57.7 |
| Delta value after-before | 36% | 2% | 3% | 8% | −4.6 | 5.0 | 7.6 |
| Solution of Avn-containing membrane filtrate fraction, with β-glucan removed, in glycerol/water as commercially available from Ceapro | | | | | | | |
| Before treatment | 17 | 37 | 38 | 92 | 76.7 | 3.9 | 58.5 |
| After treatment | <1 | 37 | 32 | <69 | 69.9 | 12.3 | 71.8 |
| Delta value after-before | 100% | 0% | 16% | >25% | −6.8 | 8.4 | 13.3 |

The results clearly show that the oat extract fraction with enriched Avns and β-glucan and reduced in cation content as obtained according to Example 7 is more stable against oxidative degradation than the Avn-enriched product, as bought from Ceapro, from which, due to the used methodology, anti-oxidant β-glucan is removed whereas oxidative degradation catalysing cations are not removed. This is particularly observable in the Avn C content and the discoloration.

The glycerol/water-based solution of oats obtained from Ceapro is also darker in colour, as can be seen from the Lab colour values, as shown in Table 15.

TABLE 15

Light stability (Xenotest 440)

| Sample | Content: Avn C [ppm] | Content: Avn A [ppm] | Content: Avn B [ppm] | Content: Total of Avns A to C [ppm] | Colour: L* | Colour: a* | Colour: b* |
|---|---|---|---|---|---|---|---|
| Solution of ethanol eluate fraction, containing Avns and β-glucan, in glycerol/water as obtained in Example 7 | | | | | | | |
| Before treatment | 22 | 52 | 64 | 138 | 85.8 | −2.9 | 50.1 |
| After treatment | 21 | 50 | 63 | 134 | 85.7 | −1.8 | 43.7 |
| Delta value after-before | −5% | −4% | −2% | −3% | −0.1 | 1.1 | −6.4 |
| Solution of Avn-containing membrane filtrate fraction, with β-glucan removed, in glycerol/water as commercially available from Ceapro | | | | | | | |
| Before treatment | 17 | 37 | 38 | 92 | 76.7 | 3.9 | 58.5 |
| After treatment | 15 | 36 | 36 | 87 | 77.6 | 3.7 | 56.4 |
| Delta value after-before | −12% | −3% | −5% | −5% | 0.9 | −0.2 | −2.1 |

The results show that the oat extract fraction with enriched Avns and β-glucan as obtained according to Example 7 is also slightly more stable against light-induced degradation than the Avn-enriched product with removed β-glucan and not removed cations, as bought from Ceapro. This is particularly observable in the Avn C content.

Example 10: Spray-Dried Oat Extraction Fraction 440 grams of water was added to an aliquot of 220 grams of the oat ethanol eluate obtained as described in Example 7, having a dry-matter content of 0.75 wt % and a content of Avns A to C of 16020 ppm in the dry matter. 198 grams of corn-derived maltodextrin DE 17-20 was then dissolved in the aqueous ethanolic solution, to give a slightly turbid but homogeneous yellowish solution which was then spray-dried, yielding 160 grams of a white powder having the particle size distribution (Mastersizer 2000, Malvern) shown in FIG. 1, wherein 10% of the particles are d(0.1)=2.868 μm, 50% of the particles are d(0.5)=8.518 μm, 90% of particles are d(0.9)=18.294 μm, and the specific surface area is 1.34 $m^2/g$.

Figure 2:
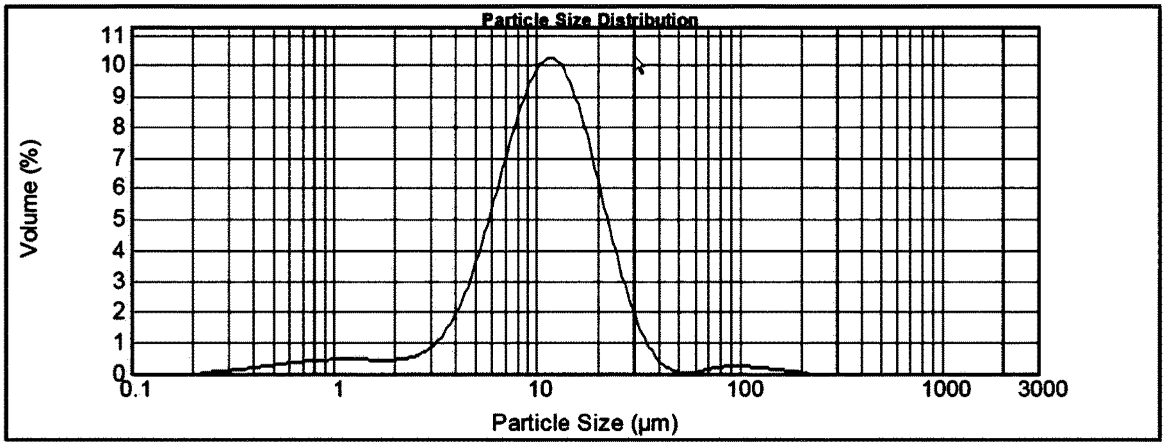
FIG. 2 is a diagram showing the particle size distribution of a spray-dried oat extraction fraction in combination with maltodextrin DE 8.

The same experiment was repeated using corn-derived maltodextrin DE 8, yielding 160 grams of a white powder having the particle size distribution (Mastersizer 2000, Malvern) shown in FIG. 2, wherein 10% of the particles are d(0.1)=4.440 μm, 50% of the particles are d(0.5)=11.022 μm, 90% of particles are d(0.9)=22.736 μm, and the specific surface area is 0.96 $m^2/g$.

TABLE 16

| Extract | Content: Avn C [ppm] | Avn A [ppm] | Avn B [ppm] | Total of Avns A to C [ppm] | Avn L [ppm] | β-Glucan [wt %] |
|---|---|---|---|---|---|---|
| Spray-dried ethanol eluate on maltodextrin DE 17-20 | 17 | 46 | 52 | 115 | 10 | 0.06 |
| Spray-dried ethanol eluate on maltodextrin DE 8 | 16 | 48 | 51 | 115 | 7 | 0.07 |

Using the same drying technology an oat ethanol fraction concentrate powder was prepared: 1200 g maltodextrin DE 17-20 were dissolved in 1500 g of water. To the clear solution, 300 g of a 10 wt % solution of an oat ethanol eluate in ethanol/water 1:1 (w/w) obtained using the methodology as described above containing 802 ppm Avn C, 1429 ppm Avn A, 2203 ppm Avn B (sum Avn A–C=4434 ppm) and 202 ppm Avn L were added under stirring. The obtained turbid but homogeneous brownish solution was then spray-dried to give 970 g of a light beige powder containing 196 ppm Avn C, 360 ppm Avn A, 562 ppm Avn B (sum Avns A to C=1118 ppm) and 63 ppm Avn L and characterized by color values of L*=91.60, a*=−0.12, b*=11.36.

Spray-dried solid powders or granulates have the advantage that they are easy to handle and dose. Spray-drying is a very gentle drying technique, as it requires only a very short exposure (of less than one minute) to higher temperatures, making it particularly suitable for sensitive ingredients. It is also a relatively cheap technique which also allows solutions with low dry matter and low viscosity to be dried. Spray-drying is a well-established drying technology, available at commercial scale, which also allows the use of additives such as dextrins or cyclodextrins, other modified starches or gum acacia, to influence the product parameters.

The particle size can also be adapted from smaller particles (around 0.07 mm) to larger particles (up to around 0.4 mm) depending on the respective needs and requirements, for example by producing agglomerated powders using for example spray bed drying technology. This allows free-flowing and almost dust-free powders to be prepared.

Example 11: Stability of the Spray-Dried Oat Extract Fraction with Enriched Avns and β-Glucan The oxidative and light stability of the spray-dried oat extract fraction with enriched Avns and β-glucan, as obtained in Example 10, were evaluated by exposing them to 5 bars of oxygen for 72 hours at 60° C. using the Oxipress device or by irradiating them for 6 hours using a Xenotest 440 instrument (60 W, 1294 kJ/m$^2$, wavelength 300-400 nm).

The content of Avns was determined by HPLC, and the colour was measured by colorimetry before and after treatment.

TABLE 17

Oxidative stability (Oxipress)

| Sample | Avn C [ppm] | Avn A [ppm] | Avn B [ppm] | Total of Avns A to C [ppm] | Avn L [ppm] | Colour L* | a* | b* |
|---|---|---|---|---|---|---|---|---|
| | Content | | | | | | | |
| Spray-dried ethanol eluate on maltodextrin DE 17-20 (Example 10) | | | | | | | | |
| Before treatment | 17 | 46 | 52 | 115 | 10 | 96.7 | −0.8 | 4.5 |
| After treatment | 16 | 46 | 52 | 114 | 10 | 96.7 | −0.8 | 4.8 |
| Delta value after-before | −1 | 0 | 0 | −1 | 0 | 0 | 0 | 0.3 |

The results clearly show that the spray-dried oat extract fraction with enriched Avns and β-glucan, as obtained according to Example 10, is completely stable against oxidative degradation, since the content of Avns was not affected and no discoloration was observed.

TABLE 18

Light stability (Xenotest 440)

| Sample | Avn C [ppm] | Avn A [ppm] | Avn B [ppm] | Total of Avns A to C [ppm] | Avn L [ppm] | Colour L* | a* | b* |
|---|---|---|---|---|---|---|---|---|
| | Content | | | | | | | |
| Spray-dried ethanol eluate on maltodextrin DE 17-20 (Example 10) | | | | | | | | |
| Before treatment | 17 | 46 | 52 | 115 | 10 | 96.7 | −0.8 | 4.5 |
| After treatment | 17 | 46 | 52 | 115 | 10 | 96.5 | −0.8 | 4.1 |
| Delta value after-before | 0 | 0 | 0 | 0 | 0 | −0.2 | 0 | −0.4 |

The results clearly show that the spray-dried oat extract fraction with enriched Avns and β-glucan, as obtained according to Example 10, is completely stable against light exposure, since the content of Avns was not affected and no discoloration was observed.

Comparable results for oxidative and light exposure were obtained for the spray-dried ethanol eluate on maltodextrin DE 8, obtained according to Example 10, showing that the DE value of the maltodextrin used does not influence stability.

Example 12: Preparation of an Extract Fraction of *Avena sativa* (Common Oat) Grains Containing Avns and β-Glucan—Comparing pH 3.0 and Non-Adjusted pH 950 grams of non-milled organic common oat grains (obtained from Nordlicht Naturkost and cultivated in Germany) was extracted twice as described in Example 3 using 1800 and 1200 grams of 50% aqueous ethanol (w/w) in the first and second extraction, respectively, in each case for 2 hours at 60° C. with stirring. The extraction yield was determined as described in Example 5, resulting in an extraction yield of 2.2 wt %.

The water filtrate and washing water were combined and lyophilised, to obtain 4.5 grams of dry water fraction, corresponding to a yield of 1.1 wt % based on oat grains.

The ethanol was removed from the ethanolic eluate by vacuum, to obtain 3.0 grams of dry ethanol fraction, corresponding to a yield of 0.7 wt % based on oat grains.

In the second part:

(B) Another 930 grams of it (8.8 grams of dry extract) was treated as described in (A), to give 800 grams of aqueous extract solution (1.1 wt % dry matter). The pH value of this solution was not adjusted.

250 grams of Lewatit® VP OC 1064 MD PH resin (Lanxess), washed in accordance with the supplier's instructions and conditioned in water, was filled into a 4 cm diameter glass column, and the aqueous extract solution was submitted to it with no pH adjustment. Adsorption and elution were performed as described in (A).

The water filtrate and washing water were combined and lyophilised, to obtain 6.3 grams of dry water fraction, corresponding to a yield of 1.6 wt % based on oat grains.

The ethanol was removed from the ethanolic eluate by vacuum, to obtain 2.1 grams of dry ethanol fraction, corresponding to a yield of 0.5 wt % based on oat grains.

The dried extracts and fractions were characterised as described above, and the results are summarised in Table 19.

TABLE 19

| Extract | Dry extract yield* [wt %] | Content: Avn C [ppm] | Avn A [ppm] | Avn B [ppm] | Total of Avns A to C [ppm] | Avn L [ppm] | Glucose [wt %] | β-Glucan [wt %] |
|---|---|---|---|---|---|---|---|---|
| Dried aqueous ethanol extract | 2.2 | 328 | 340 | 781 | 1449 | n.d. | 0.19 | 0.87 |
| (A) Dried water filtrate (pH 3.0) | 1.1 | <10 | <10 | <10 | <10 | n.d. | 3.1 | <0.1 |
| (A) Dried ethanol eluate (pH 3.0) | 0.7 | 965 | 998 | 2226 | 4189 | n.d. | 0.54 | 1.89 |
| (B) Dried water filtrate (not pH-adjusted) | 1.6 | <10 | <10 | <10 | <10 | n.d. | n.d | n.d. |
| (B) Dried ethanol eluate (not pH-adjusted) | 0.5 | 1229 | 1250 | 2816 | 5294 | n.d. | n.d. | n.d. |

*Based on oat grains

The remaining 1920 grams of extract solution was divided into two parts. In the first part:

(A) The ethanol was removed from 990 grams of it (9.4 grams of dry extract) by vacuum using an evaporator, to give 400 grams which were diluted by adding water to give 800 grams of aqueous extract solution (1.2 wt % dry matter). The pH value was then adjusted to 3.0 by means of hydrochloric acid.

250 grams of Lewatit® VP OC 1064 MD PH resin (Lanxess), washed in accordance with the supplier's instructions and conditioned in water, was filled into a 4 cm diameter glass column, and the pH-adjusted aqueous extract solution was submitted to it. The solution was passed through the column at a gravity-induced flow. The filtrate obtained was re-submitted onto the column twice. The column was then washed with 300 grams of water, and excess water was removed by vacuum or by blowing nitrogen through the resin. The adsorbed extract ingredients were then eluted from the resin using 600 grams of ethanol.

The results show that both dried ethanol eluate fractions exhibit a higher content of Avns as compared to the dried aqueous ethanol extract. The dried ethanol eluate fraction obtained from the aqueous extract solution with no pH adjustment contains a 3.8-fold higher total content of Avns A to C, and the dried ethanol eluate fraction obtained from the aqueous extract solution with adjustment to pH 3 contains a 3.0-fold higher total content of Avns A to C (5294 and 4189 ppm versus 1385 ppm).

However, the dried ethanol eluate fraction obtained from the aqueous extract solution with no pH adjustment contains a 26% (1.26-fold) higher total content of Avns A to C, compared to the one with adjustment to pH 3 (5294 versus 4189 ppm).

Surprisingly, the dried ethanol eluate fraction (A) also contains a 2.2-fold higher content of β-glucan than the dried aqueous ethanol extract, even though β-glucans are water-soluble.

Example 13: Extraction of Non-Milled Naked Oat (*Avena nuda*) Grains with Different Extracting Solvents (Extractants)

100 g naked oat grains (bought from Bohlenser Mühle, cultivated in Germany, cultivar Oliver) were extracted with 300 g of extractant as given in the following table (w/w) for 2 hours at 55° C. under stirring. The mixture was cooled down to room temperature and the grains were separated from the extract solution by centrifugation and filtration. The extracted grains were extracted with a second portion of 300 g extractant gain for 2 h at 55° C. and extract solution was separated from grains as described above. The two extract solutions were combined, the extracting solvents were removed under vacuum by use of an evaporator and the obtained dry extracts were weight to determine the extraction yields. Avns were quantified in the dry extracts as described in Example 1.

TABLE 20

Characterization of naked oat extracts obtained with different extracting solvents (extractants)

| Extractant (w/w) | Dry extract yield* [wt.- %] | Content | | | | | | |
|---|---|---|---|---|---|---|---|---|
| | | Avn C [ppm] | Avn A [ppm] | Avn B [ppm] | Total of Avns A to C [ppm] | Avn L [ppm] | Avn L iso** [ppm] | β-Glucan [%] |
| Water | 10.3 | n.d. | 12 | 14 | 26 | n.d. | n.d. | n.d. |
| Methanol/water 3:7 | 2.2 | 110 | 737 | 1183 | 2030 | 128 | 105 | 1.88 |
| Methanol/water 1:1 | 2.6 | 364 | 1029 | 1471 | 2864 | 276 | 195 | 1.90 |
| Methanol/water 7:3 | 2.3 | 349 | 967 | 1441 | 2757 | 311 | 194 | 1.67 |
| Ethanol/water 1:1 | 3.0 | 373 | 1051 | 1471 | 2895 | 328 | 188 | n.a. |
| Ethanol/water 1:4 | 2.9 | 61 | 157 | 534 | 752 | 5 | 35 | 2.73 |
| Isopropanol/water 3:7 | 3.4 | 471 | 1118 | 1673 | 3262 | 347 | 227 | 1.72 |
| Isopropanol/water 1:1 | 3.1 | 423 | 1049 | 1535 | 3007 | 353 | 231 | 1.25 |
| Isopropanol/water 7:3 | 2.4 | 492 | 1151 | 1639 | 3282 | 422 | 216 | 1.38 |
| Acetone/water 3:7 | 3.0 | 344 | 1080 | 1655 | 3079 | 265 | 220 | 1.78 |
| Acetone/water 1:1 | 3.7 | 437 | 1063 | 1539 | 3039 | 270 | 194 | 1.26 |
| Acetone/water 7:3 | 2.6 | 627 | 1527 | 2194 | 4348 | 423 | 287 | 1.85 |

*Based on oat grains

**Structural isomer of Avn L with same molecular weight and fragmentation pattern according to HPLC-MS measurement, see also Example 7, Table 10, quantified by HPLC as Avn L n.d. = not detectable n.a. = not analyzed The results clearly show that extraction by water alone does not give a suitable extract as Avns contents are low and β-glucan was not detectable. All extracts obtained by mixtures of organic solvent and water are suitable as they simultaneously contain Avns and β-glucans making them generally suitable to be fractionated by adsorption step as described in the examples before. Extract yield was between 2.2 and 3.7% and extracts contained between 1.25 and 2.73% β-glucan and between 752 and 4348 ppm Avns A C in sum.

Example 14: Comparison Oat Extract According to the Present Invention (Example 7) and Oat Extract According to WO 2004/047833 A1

Extraction of an anthranilic acid amide-containing extract from cultivated oat straw (*Avena sativa*) as described in Example 3 in WO 2004/047833 A1:

143 kg ethanol/water 7:3 (v/v) are added to 9 kg cultivated oat straw and the mixture is macerated for 3 days at room temperature. After filtration, the extract is concentrated to the aqueous phase under vacuum (17.4 kg, solids content: 2.5%; sum of Avenanthramides A, B and C in dry extract: 0.093%).

The aqueous solution is extracted in portions (2 kg) by stirring with Amberlite XAD-16 (270 g). The adsorber resin is separated off via a frit, washed with water and eluted with methanol/water 1:1 (v/v). The combined eluates are freed from solvent under vacuum. Dry extract: 8.5 g; sum Avenanthramides A, B and C: 1.2%.

This dry extract is taken up in ethanol/water 1:1 (v:v) and adjusted to an avenanthramide content, i.e. sum Avenanthramides A, B and C of 500 ppm by dilution with ethanol/water 1:1 (v/v).

As it is described in the literature, oat straw also contains β-glucan: Hager Rom 2006, Hagers Handbuch der Drogen und Arzneistoffe: Avenae stramentum (oat straw): Ingredients: carbohydrates, β-glucanes [8], cellulose, xylanes and the oligosaccharides kestose, neokestose, bifurcose, neobifurcose; [7] avenarin [53], pektines 0.8% [17] or D. M. Gibeaut et al., Plant Physiol. 1990, 94, 411-416: β-glucanes in leaf-sheath pulvinus [=a joint-like thickening at the base of a plant leaf or leaflet that facilitates growth-independent movement (Wikipedia)] of oat, and, thus, also in oat straw.

TABLE 21

| Oat extract according to Example 7 | Oat extract according to Example 3 in WO 2004/047833 |
|---|---|
| 500 kg oat grains; EtOH/water (1:1); 2 × 2 h, 55-60° C. | 9 kg oat straw; EtOH/water (7:3); 3 days at room temperature |
| Yield: 2.5% according to 13 kg dry extract | 17.4 kg of a extract solution (2.5%), corresponding to 0.435 kg dry extract |
| Sum of Avenanthramides A to C: 1614 ppm = 0.1614% | Sum of Avenanthramides A to C: 0.093% |
| Corresponds to an absolute amount of Avenanthramides A to C in sum of 0.02098 kg | Corresponds to an absolute amount of Avenanthramides A to C in sum of 0.404 g |
| Adsorption step with Lewatit: yield: 0.2% corresponding to 1 kg dry extract (based on oat grains) | Adsorption step with XAD-16: 8.5 g dry extract corresponding to 0.094% (based on oat straw) |
| Avenanthramides A to C in sum: 16020 ppm = 1.6020% | Avenanthramides A to C in sum: 1.2% |
| Corresponds to an absolute amount of Avenanthramides A to C in sum of 0.01602 kg | Corresponds to an absolute amount of Avenanthramides A to C in sum of 0.102 g |
| Recovery of Avenanthramides A to C from oat source = 76.4% | Recovery of Avenanthramides A to C from oat source = 25.2% |

The comparison clearly shows that the recovery of avenanthramides from the oat source is much more efficient by using the process according to Example 7 (76.4% versus only 25.2% by the process according to Example 3 in WO 2004/047833).

The dried methanol/water 1:1 (v/v) eluate of the oat straw extract according to WO 2004/047833 A1 was analysed by HPLC-DAD-MS measurement using an acetonitrile/water/0.1% formic acid gradient on an ODS-AQ column (YMC) (Bruker Esquire ion trap in positive and negative ion mode) for Avns. The results are summarized in Table 22.

Figure 4:
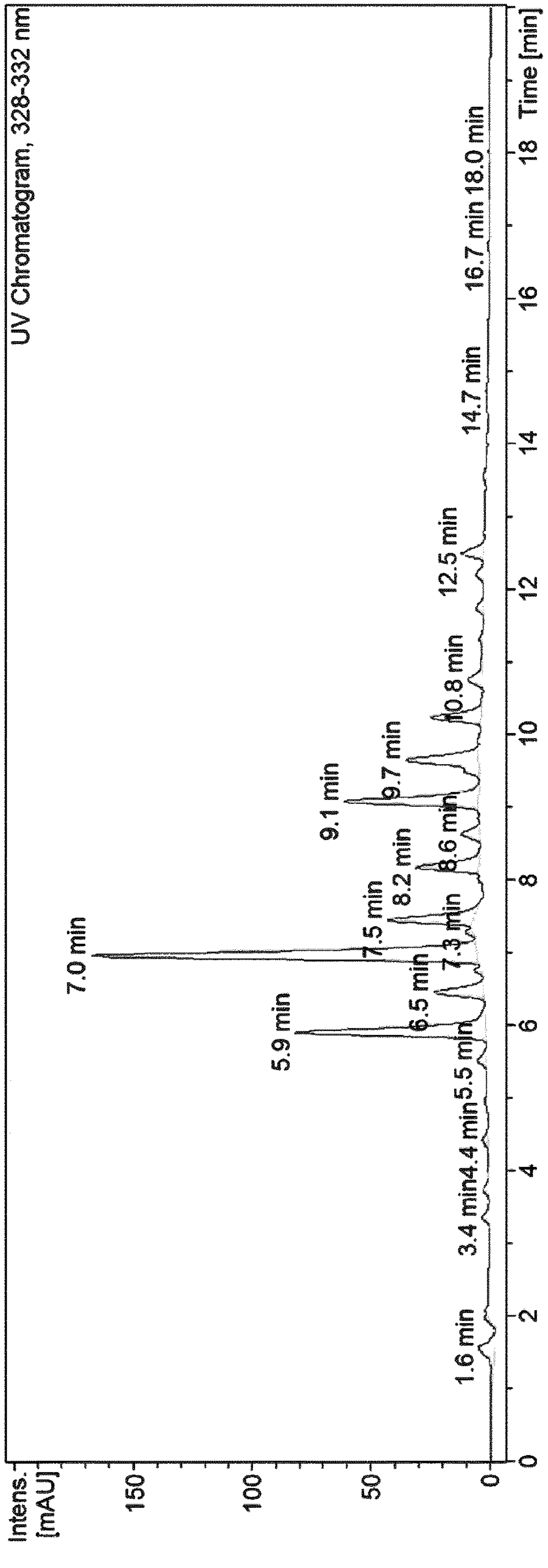
FIG. 4 is a HPLC-chromatogram of the dried methanol/water eluate of the oat straw extract according to WO 2004/047833 A1 of Example 14.

The HPLC-chromatogram of the dried methanol/water 1:1 (v/v) eluate at 328-332 nm is represented in FIG. 4.

TABLE 22

Avns composition of the oat straw methanol/water 1:1 (v/v) eluate according to Example 3 in WO 2004/047833

| Rt [min] | ESI neg | Molecular weight [g/mol] | ESI pos Avn Fragment | Cinnamic acid part of the Avn | Calculated anthranilic acid fragment | Anthranilic acid part of the Avn | Avn* |
|---|---|---|---|---|---|---|---|
| 4.4 | 314 | 315 | 163 | Caffeic acid | 152 | 5-OH-anthranilic acid | Avn C |
| 5.5 | 314 | 315 | 163 | Caffeic acid | 152 | 4-OH-anthranilic acid | Avn K |
| 5.9 | 298 | 299 | 147 | p-Coumaric acid | 152 | 5-OH-anthranilic acid | Avn A |
| 6.5 | 328 | 329 | 177 | Ferulic acid | 152 | 5-OH-anthranilic acid | Avn B |
| 6.7 | 328 | 329 | 147 | p-Coumaric acid | 182 | 4-OMe-5-OH-anthranilic acid | Avn X |
| 6.9 | 298 | 299 | 147 | p-Coumaric acid | 152 | 5-OH-anthranilic acid | Avn G |
| 7.2 | 358 | 359 | 177 | Ferulic acid | 182 | 4-OMe-5-OH-anthranilic acid | Avn 2** (Y*) |
| 7.5 | 328 | 329 | 177 | Ferulic acid | 152 | 5-OH-anthranilic acid | Avn H |
| 8.2 | 324 | 325 | 173 | Avenalumic acid | 152 | 4-OH-anthranilic acid | Avn L** (O*) |
| 8.6 | 324 | 325 | 173 | Avenalumic acid | 152 | . . . -OH-anthranilic acid | Avn L isomer |
| 9.2 | 324 | 325 | 173 | Avenalumic acid | 152 | 5-OH-anthranilic acid | Avn R |
| 9.6 | 324 | 325 | 173 | Avenalumic acid | 152 | . . . -OH-anthranilic acid | Avn R isomer |
| 9.9 | 282 | 283 | 131 | Cinnamic acid | 152 | 5-OH-anthranilic acid | CAS number 207742-91-4 |
| 10.2 | 282 | 283 | 147 | p-Coumaric acid | 136 | Anthranilic acid | Avn D |
| 10.8 | 312 | 313 | 177 | Ferulic acid | 136 | Anthranilic acid | Avn E |
| 12.5 | 308 | 309 | 173 | Avenalumic acid | 136 | Anthranilic acid | Avn L |

*Abbreviations Collins [de Bruijn et al., Food Chemistry (2018), https://doi.org/10.1016/j.foodchem.2018.11.013, supplementary information Table S1]

**Other common name, non-Collins abbreviations

Example 15: Content of Avenanthramides, β-Glucan and Salts in Oat Extract Fractions

TABLE 23

Weight ratio of avenanthramides to β-glucan

| | Content HPLC [ppm] | | | | | | | | weight ratio Avns to β-glucan (β-glucan = 1) | |
|---|---|---|---|---|---|---|---|---|---|---|
| | Sum Avns | | | | | Glucan Kit | | | sum Avns | lowest Avn |
| Extract | A-C | Avn C | Avn A | Avn B | Avn L | β-glucan | Glucose | Examples | A to C | given* |
| SymTrap EtOH Eluate (pH3) | 22239 | 4840 | 7862 | 9537 | n.b. | 2.79 | 0.17 | 3 | 0.80 | 0.17 |
| SymTrap EtOH Eluate (pH3) | 9146 | 1753 | 3390 | 4003 | n.b. | 2.36 | 0.63 | 5 | 0.39 | 0.07 |
| SymTrap EtOH Eluate (pH not adjusted) pH = 6.4 | 10544 | 1922 | 3864 | 4758 | n.b. | 2.21 | 0.19 | | 0.48 | 0.09 |
| SymTrap EtOH Eluate | 8311 | 1344 | 2651 | 4316 | 792 | 2.08 | 0.29 | 6 | 0.40 | 0.04 |
| EtOH-Eluate | 16020 | 2540 | 6262 | 7218 | 1276 | 1.65 | 0.14 | 7 | 0.97 | 0.08 |

The weight ratio of the at least one avenanthramide or the total avenanthramides to β-glucan is in a range of 0.25:1 to 4:1, more preferred in a range of 0.3:1 to 3:1.

TABLE 24

Salt content

| | EtOH Eluate | | |
|---|---|---|---|
| Salts** | Example 3 | Example 7 | |
| Na | 0.01 | 0.046 | 0.038 |
| K | 0.01 | 0.094 | 0.22 |
| Cl | 0.15 | 0.034 | 0.037 |
| $SO_4^{2-}$ | 0.01 | 0.043 | 0.022 |
| $PO_4^-$ | 0.02 | 0.022 | 0.025 |
| Sum: | 0.20 | 0.239 | 0.342 |

The content of salts in the oat extract is ≤1 wt %, in particular ≤0.5 wt %.

Example 16: Formulation Examples

In the formulation examples 1 to 11 the following two perfume oils PFO1 and PFO2 were each used as fragrance (DPG=dipropylene glycol).

TABLE 25

Perfume oil PFO1 with rose smell (amounts in parts by weight)

| Component | Amount |
|---|---|
| Acetophenone, 10% in DPG | 10.00 |
| n-Undecanal | 5.00 |
| Aldehyde C14, so-called (peach aldehyde) | 15.00 |
| Allylamyl glycolate, 10% in DPG | 20.00 |
| Amyl salicylate | 25.00 |
| Benzyl acetate | 60.00 |
| Citronellol | 80.00 |
| d-Limonene | 50.00 |
| Decenol trans-9 | 15.00 |
| Dihydromyrcenol | 50.00 |
| Dimethylbenzylcarbinyl acetate | 30.00 |

TABLE 25-continued

Perfume oil PFO1 with rose smell (amounts in parts by weight)

| Component | Amount |
|---|---|
| Diphenyloxide | 5.00 |
| Eucalyptol | 10.00 |
| Geraniol | 40.00 |
| Nerol | 20.00 |
| Geranium oil | 15.00 |
| Hexenol cis-3, 10% in DPG | 5.00 |
| Hexenyl salicylate cis-3 | 20.00 |
| Indole, 10% in DPG | 10.00 |
| Alpha-ionone | 15.00 |
| Beta-ionone | 5.00 |
| Lilial ® (2-methyl-3-(4-tert-butyl-phenyl)propanal) | 60.00 |
| Linalool | 40.00 |
| Methylphenyl acetate | 10.00 |
| Phenylethyl alcohol | 275.00 |
| Styrolyl acetate | 20.00 |
| Terpineol | 30.00 |
| Tetrahydrolinalool | 50.00 |
| Cinnamyl alcohol | 10.00 |
| Total: | 1,000.00 |

TABLE 26

Perfume oil PFO2 with white blossom and musk smell (amounts in parts by weight)

| Component | Amount |
|---|---|
| Benzyl acetate | 60.00 |
| Citronellyl acetate | 60.00 |
| Cyclamenaldehyde (2-methyl-3-(4-isopropylphenyl)propanal | 20.00 |
| Dipropylene glycol (DPG) | 60.00 |
| Ethyllinalool | 40.00 |
| Florol (2-isobutyl-4-methyltetrahydro-2H-pyran-4-ol) | 30.00 |
| Globanone ® [(E/Z)-8-cyclohexadecen-1-one] | 180.00 |
| Hedione ® (methyldihydrojasmonate) | 140.00 |
| Hexenyl salicylate, cis-3 | 10.00 |
| Vertocitral (2,4-dimethyl-3-cyclohexenecarboxaldehyde) | 5.00 |
| Hydratropaaldehyde, 10% in DPG | 5.00 |
| Isodamascone (1-(2,4,4-trimethyl-2-cyclohexen-1-yl)-2-buten-1-one, 10% in DPG | 5.00 |

TABLE 26-continued

| Perfume oil PFO2 with white blossom and musk smell (amounts in parts by weight) | |
|---|---|
| Component | Amount |
| Isomuscone (cyclohexadecanone) | 40.00 |
| Jacinthaflor (2-methyl-4-phenyl-1,3-dioxolane) | 10.00 |
| Cis-jasmone, 10% in DPG | 20.00 |
| Linalool | 50.00 |
| Linalyl acetate | 30.00 |
| Methyl benzoate, 10% in DPG | 25.00 |
| para-Methyl cresol, 10% in DPG | 10.00 |
| Nerol | 20.00 |

TABLE 26-continued

| Perfume oil PFO2 with white blossom and musk smell (amounts in parts by weight) | |
|---|---|
| Component | Amount |
| Phenylpropylaldehyde | 5.00 |
| 2-Phenylethyl alcohol | 82.00 |
| Tetrahydrogeraniol | 13.00 |
| 2,2-Dimethyl-3-cyclohexyl-1-propanol | 80.00 |
| Total: | 1,000.00 |

TABLE 27

Cosmetic formulations (amounts in parts by weight)
1 = Skin calming balm for sensitive skin
2 = Tinted anti-aging face balm, SPF 15
3 = After-sun moisturizing spray O/W
4 = Night cream W/O
5 = Skin cleansing gel
6 = After-shave hydrogel
7 = Anti-dandruff hair shampoo
8 = Anti-perspirant pump spray
9 = Skin lightening day care fluid O/W
10 = Skin barrier improving cream O/W
11 = Sun care lotion SPF 24 (UVA/UVB balance)

| Ingredients | 1 | 2 | 3 | 4 | 5 | 6 | 7 | 8 | 9 | 10 | 11 |
|---|---|---|---|---|---|---|---|---|---|---|---|
| Ethanol eluate fraction in glycerin/water standardized to 100-130 ppm Avns A to C in sum | | | | | | | | | | | |
| Water (Aqua), Glycerin, Avena nuda (oat) kernel extract Ethanol eluate fraction in glycerin/water standardized to ≥ 100 ppm Avns in sum | | 2 | | 1 | | 2.5 | | | 1.5 | | 0.5 |
| Water (Aqua), Glycerin, Avena sativa (oat) kernel extract Spray-dried ethanol eluate fraction on maltodextrin standardized to ≥ 1000 ppm Avns A to C in sum | | | 4 | | | | 5 | 0.5 | | | |
| Maltodextrin, Avena nuda (oat) kernel extract Actipone ® Laminaria Saccharina | 1 | | | | 0.5 | | | | | 0.1 | |
| Glycerin, Water (Aqua), Laminaria Saccharina Extract Allantoin | | | | | | 0.3 | | | | | |
| Allantoin Aloe Vera Gel Conc.10:1 | 0.1 | | | | | 0.1 | | | | | |
| Aloe Barbadensis(Aloe) Leaf Juice Aluminium Stearate | | | | | | 1 | | | | | |
| Aluminium Stearate | | | | 1.2 | | | | | | | |

TABLE 27-continued

Cosmetic formulations (amounts in parts by weight)
1 = Skin calming balm for sensitive skin
2 = Tinted anti-aging face balm, SPF 15
3 = After-sun moisturizing spray O/W
4 = Night cream W/O
5 = Skin cleansing gel
6 = After-shave hydrogel
7 = Anti-dandruff hair shampoo
8 = Anti-perspirant pump spray
9 = Skin lightening day care fluid O/W
10 = Skin barrier improving cream O/W
11 = Sun care lotion SPF 24 (UVA/UVB balance)

| Ingredients | 1 | 2 | 3 | 4 | 5 | 6 | 7 | 8 | 9 | 10 | 11 |
|---|---|---|---|---|---|---|---|---|---|---|---|
| Beta-Arbutin | | | | | | | | | | | |
| Arbutin | | | | | | | | | 1 | | |
| Arlypon ® F | | | | | | | | | | | |
| Laureth-2 | | | | | | | 2 | | | | |
| Avocado Oil | | | | | | | | | | | |
| Persea Gratissima (Avocado) Oil | | | 3 | | | | | | | | |
| Betulin 90% | | | | | | | | | | | |
| Betulin | | | | | | | | | | 0.1 | |
| Biotive L-Arginine | | | | | | | | | | | |
| Arginine | | 0.6 | | | | | | | | | 0.5 |
| Biotive Troxerutin | | | | | | | | | | | |
| Troxerutin | | 0.5 | | | | | | | | | 0.5 |
| (−)-alpha-Bisabolol | | | | | | | | | | | |
| Bisabolol | | | | | | | | | | | 0.1 |
| Carbopol Aqua SF-1 Polymer | | | | | | | | | | | |
| Acrylates Copolymer | | | | | 5 | | | | | | |
| Carbopol ® Ultrez-10 | | | | | | | | | | | |
| Carbomer | | 0.2 | | | | 0.4 | | | 0.2 | | |
| CeramideBIO ® | | | | | | | | | | | |
| Cetylhydroxyproline Palmitamide | | | | | | | | | | 0.5 | |
| Citric acid 10% in water | | | | | 0.2 | | 0.5 | | | | |
| Covi-Ox ® T-70 | | | | | | | | | | | |
| Tocopherol | | | 0.1 | | | | | | | | |
| Crinipan ® AD | | | | | | | | | | | |
| Climbazole | | | | | | | 0.3 | | | | |
| Cutina ® PES | | | | | | | | | | | |
| Pentaerythrityl Distearate | | 2 | | | | | | | | | |
| D-Panthenol | | | | | | | | | | | |
| Panthenol | 1 | | 1 | | | 0.5 | 0.5 | | | | |
| Dehyton K | | | | | | | | | | | |
| Cocamidopropyl Betaine | | | | | 8 | | 8 | | | | |
| Dermacryl ® AQF | | | | | | | | | | | 2 |
| Acrylates Copolymer | | | | | | | | | | | |
| Dow Corning 200(100cs) | | | | | | | | | | | |
| Silicone Fluid Dimethicone | 2 | 2 | | | | | | | 0.5 | 0.5 | |
| Dow Corning 246 Fluid | | | | | | | | | | | |
| Cyclohexasiloxane, Cyclopentasiloxane | | | 2 | | | | | | | | 3 |

TABLE 27-continued

Cosmetic formulations (amounts in parts by weight)
1 = Skin calming balm for sensitive skin
2 = Tinted anti-aging face balm, SPF 15
3 = After-sun moisturizing spray O/W
4 = Night cream W/O
5 = Skin cleansing gel
6 = After-shave hydrogel
7 = Anti-dandruff hair shampoo
8 = Anti-perspirant pump spray
9 = Skin lightening day care fluid O/W
10 = Skin barrier improving cream O/W
11 = Sun care lotion SPF 24 (UVA/UVB balance)

| Ingredients | 1 | 2 | 3 | 4 | 5 | 6 | 7 | 8 | 9 | 10 | 11 |
|---|---|---|---|---|---|---|---|---|---|---|---|
| Dracorin ® CE | | | | | | | | | | | |
| Glyceryl Stearate Citrate | | | | | | | | | | 1.5 | |
| Dracorin ® GMS | | | | | | | | | | | |
| Glyceryl Stearate | | | | | | | | | | 2 | |
| Dracorin ® GOC | | | | | | | | | | | |
| lyceryl Oleate Citrate, Caprylic/Capric Triglyceride | | | 2 | | | | | | | | |
| Dragocid ® Liquid | | | | | | | | | | | |
| Phenoxyethanol, Methylparaben, Ethylparaben, Butylparaben, Propylparaben, Isobutylparaben | | | | | | | | | 0.8 | | |
| Dragoderm ® | | | | | | | | | | | |
| Glycerin, Triticum Vulgare (Wheat) Gluten, Water(Aqua) | | | | | | | 0.5 | | | | |
| Dragosan ® W/O P | | | | | | | | | | | |
| Sorbitan Isostearate, Hydrogenated Castor Oil, Ceresin, Beeswax (Cera Alba) | | | | 8 | | | | | | | |
| Dragosantol ® 100 | | | | | | | | | | | |
| Bisabolol | | | | | 0.2 | | | | | | |
| Dragosine ® | | | | | | | | | | | |
| Carnosine | | 0.2 | | | | | | | | | |
| Dragoxat ® 89 | | | | | | | | | | | |
| Ethylhexyl Isononanoate | | 5 | | 7 | | | | | | 2 | 2 |
| Disodium EDTA | 0.1 | 0.1 | | | | | | | 0.1 | | 0.1 |
| Emulsiphos ® | | | | | | | | | | | |
| Potassium Cetyl Phosphate, Hydrogenated Palm Glycerides | | 2 | | | | | | | 1.5 | 2 | 2 |
| Ethanol | | | 5 | | | 8 | | | | | |
| Extrapone ® Aloe vera | | | | | | | | | | | |
| Water (Aqua), Aloe Barbadensis, Propylene Glycol, Alcohol | | | | | | 2 | | | | | |
| Extrapone ® Witch Hazel | | | | | | | | | | | |
| Propylene Glycol, Hamamelis Virginiana (Witch Hazel) Water, Water (Aqua), Hamamelis Virginiana (Witch Hazel) Extract | 1 | | | | | | | | | | |

TABLE 27-continued

Cosmetic formulations (amounts in parts by weight)
1 = Skin calming balm for sensitive skin
2 = Tinted anti-aging face balm, SPF 15
3 = After-sun moisturizing spray O/W
4 = Night cream W/O
5 = Skin cleansing gel
6 = After-shave hydrogel
7 = Anti-dandruff hair shampoo
8 = Anti-perspirant pump spray
9 = Skin lightening day care fluid O/W
10 = Skin barrier improving cream O/W
11 = Sun care lotion SPF 24 (UVA/UVB balance)

| Ingredients | 1 | 2 | 3 | 4 | 5 | 6 | 7 | 8 | 9 | 10 | 11 |
|---|---|---|---|---|---|---|---|---|---|---|---|
| Extrapone ® Rosemary | | | | | | | | | | | |
| Glycerin, Water (Aqua), Rosmarinus Officinalis (Rosemary) Leaf Extract | | | | | | | 0.3 | | | | |
| Extrapone ® Seaweed Water | | | | | | | | | | | |
| (Aqua), Butylene Glycol, Fucus Vesiculosus Extract | | | | | | 0.5 | | | | | |
| Farnesol DT | | | | | | | | | | | |
| Phenoxyethanol, Farnesol, Bisabolol | | | | | | | | 0.2 | | | |
| Food colour brown | | | | | | | | | | | |
| E172 + E171 Powder | | 2 | | | | | | | | | |
| Frescolat ® MGA | | | | | | | | | | | |
| Menthone Glycerin Acetal | | | 0.1 | | | | | | | | |
| Frescolat ® ML | | | | | | | | | | | |
| Menthyl Lactate | | | 0.5 | | | 0.3 | 0.2 | | | | |
| Frescolat ® X-Cool | | | | | | | | | | | |
| Menthyl Ethylamido Oxalate | | | | | | | | | | 0.2 | |
| Genapol ® LRO Liquid | | | | | | | | | | | |
| Sodium Laureth Sulfate | | | | | | | 37 | | | | |
| Givobio ® GZN | | | | | | | | | | | |
| Zinc Gluconate | | | | | | | | | | 0.5 | |
| Glycerin | 1.5 | | 4 | 3 | | | | | 3.5 | 3 | 3 |
| Hydrolite ® 5 | | | | | | | | | | | |
| Pentylene Glycol | 3 | | 5 | | 2 | 5 | | 5 | | | 2 |
| Hydroviton-24 ® | | | | | | | | | | | |
| Water (Aqua), Pentylene Glycol, Glycerin, Lactic Acid, Sodium Lactate, Serine, Urea, Sorbitol, Sodium Chloride, Allantoin | | | | 1 | | | | | | | |
| Hydroviton ® Plus 2290 | | | | | | | | | | | |
| Water (Aqua), Pentylene Glycol, Glycerin, Fructose, Urea, Citric acid, Sodium Hydroxide, Maltose, Sodium PCA, Sodium Chloride, Sodium Lactate, Trehalose, Allantoin, Sodium Hyaluronate, Glucose | | | | | | | | 1 | | 2 | |

TABLE 27-continued

Cosmetic formulations (amounts in parts by weight)
1 = Skin calming balm for sensitive skin
2 = Tinted anti-aging face balm, SPF 15
3 = After-sun moisturizing spray O/W
4 = Night cream W/O
5 = Skin cleansing gel
6 = After-shave hydrogel
7 = Anti-dandruff hair shampoo
8 = Anti-perspirant pump spray
9 = Skin lightening day care fluid O/W
10 = Skin barrier improving cream O/W
11 = Sun care lotion SPF 24 (UVA/UVB balance)

| Ingredients | 1 | 2 | 3 | 4 | 5 | 6 | 7 | 8 | 9 | 10 | 11 |
|---|---|---|---|---|---|---|---|---|---|---|---|
| Isoadipate | | | | | | | | | | | |
| Diisopropyl Adipate | | | | | | | | | 2 | | |
| Isodragol ® | | | | | | | | | | | |
| Triisononanoin | 1 | | | | | | | | | 3 | 2 |
| Jojoba Oil | | | | | | | | | | | |
| Simmondsia Chinensis (Jojoba) Seed Oil | | | | 2 | | | | | | | |
| Potassium sorbate | | | 0.1 | | | | | | | | |
| Keltrol ® CG-RD | | | | | | | | | | | |
| Xanthan Gum | | 0.2 | | | | | | | 0.2 | | 0.4 |
| Kojic acid | | | | | | | | | 0.5 | | |
| Lanette ® 16 | | | | | | | | | | | |
| Cetyl Alcohol | | | | | | | | | 1.5 | | 1 |
| Lanette ® O | | | | | | | | | | | |
| Cetearyl Alcohol | | | | | | | | | | 2 | 0.5 |
| Lara Care ® A-200 | | | | | | | | | | | |
| Galactoarabinan | | | | | | | | | | | 0.3 |
| Locron ® L | | | | | | | | | | | |
| Aluminium Chlorohydrate | | | | | | | | 16 | | | |
| Magnesiumsulfate | | | | 0.7 | | | | | | | |
| Mineral Oil | | | | 8 | | | | | | | |
| Sodium ascorbylphosphate | | | | | | | | | 1 | | |
| Sodium chloride | | | | | | | 0.1 | | | | |
| Sodium hydroxide 10% in water | 1 | | | | 2 | 0.7 | | | 0.2 | 0.3 | |
| Neo Heliopan ® 303 | | | | | | | | | | | |
| Octocrylene | | 4 | | | | | | | | | 10 |
| Neo Heliopan ® 357 | | | | | | | | | | | |
| Butylmethoxydi-benzoyl-methane | | 2 | | | | | | | 2 | | 3 |
| Neo Heliopan ® AP, | | | | | | | | | | | |
| 15% solution, neutralized with L-Arginin Aqua, Disodium Phenyl Dibenzimidazole Tetrasulfonate, Arginine | | 6.7 | | | | | | | | | 6.7 |
| Neo Heliopan ® AV | | | | | | | | | | | |
| Ethylhexyl Methoxycinnamate | | | | | | | | | 7.5 | | |
| Neo Heliopan ® BB | | | | | | | | | | | |
| Benzophenone-3 | | | | | | | | | 3 | | |
| Neo Heliopan ® E 1000 | | | | | | | | | | | |
| Isoamyl p.Methoxycinnamate | | | | | | | | | | | 1 |
| Neo Heliopan ® HMS | | | | | | | | | | | |
| Homosalate | | | | | | | | | 10 | | 5 |

TABLE 27-continued

Cosmetic formulations (amounts in parts by weight)
1 = Skin calming balm for sensitive skin
2 = Tinted anti-aging face balm, SPF 15
3 = After-sun moisturizing spray O/W
4 = Night cream W/O
5 = Skin cleansing gel
6 = After-shave hydrogel
7 = Anti-dandruff hair shampoo
8 = Anti-perspirant pump spray
9 = Skin lightening day care fluid O/W
10 = Skin barrier improving cream O/W
11 = Sun care lotion SPF 24 (UVA/UVB balance)

| Ingredients | 1 | 2 | 3 | 4 | 5 | 6 | 7 | 8 | 9 | 10 | 11 |
|---|---|---|---|---|---|---|---|---|---|---|---|
| Neo Heliopan ® OS | | | | | | | | | | | |
| Ethylhexyl Salicylate | | 3 | | | | | | | 5 | | |
| Neo Heliopan ® Hydro | | | | | | | | | | | |
| 20% solution neutralized with Biotive Arginine Aqua, Phenylbenzimidazole, Sulphonic Acid, Arginin | | 10 | | | | | | | | | 10 |
| Neo-PCL Water Soluble N | | | | | | | | | | | |
| Trideceth-9, PEG-5 Ethylhexanoate, Water (Aqua) | | | | | | 1 | 1.5 | 2 | | | |
| Neutral Oil | | | | | | | | | | | |
| Caprylic/Capric Triglyceride | | | 5 | | | | | | | 10 | |
| Niacinamide | | | | | 1 | | | | | | |
| Ozokerite Wax 2389 | | | | | | | | | | | |
| Ozokerite | | | | 2 | | | | | | | |
| Parfum oil PFO1 or PFO2 | | | | | | | | | | | |
| Parfum | 0.05 | 0.3 | 0.25 | 0.3 | | 0.1 | 0.5 | 0.7 | 0.3 | 0.1 | 0.2 |
| PCL-Liquid 100 | | | | | | | | | | | |
| Cetearyl Ethylhexanoate | 3 | 2 | 4 | 5 | | | | | | | |
| PCL-Solid | | | | | | | | | | | |
| Stearyl Heptanoate, Stearyl Caprylate | 1 | | 0.5 | | | | | | | | |
| Pemulen ® TR-2 | | | | | | | | | | | |
| Acrylates/C10-30 Alkyl Acrylate Crosspolymer | 0.6 | | 0.25 | | | | | | | | |
| Phenethylalkohol | | | | | 0.2 | | | | | | |
| Phenoxyethanol | | | | | | | | | | | 0.2 |
| Phytoconcentrole ® | | | | | | | | | | | |
| Shea Butter | 1 | | | | | | | | | | |
| Glycine Soja (Soybean) Oil, Butyrospermum Parkii (Shea Butter) | | | | | | | | | | | |
| Polymer JR 400 | | | | | | | | | | | |
| Polyquaternium-10 | | | | | | | 0.4 | | | | |
| Propylenglycol-1,2 | | | | | | | | | | | |
| Propylene Glycol | | | | | | 5 | | 3 | | | |
| Silcare Silicone 41M65 | | | | | | | | | | | |
| Stearyl Dimethicone | | | | | | | | | | | 1 |
| Solubilizer | | | | | | | | | | | |
| PEG-40 Hydrogenated Castor Oil, Trideceth-9, Propylene Glycol, Water (Aqua) | | | | | | | | 3 | | | |

TABLE 27-continued

Cosmetic formulations (amounts in parts by weight)
1 = Skin calming balm for sensitive skin
2 = Tinted anti-aging face balm, SPF 15
3 = After-sun moisturizing spray O/W
4 = Night cream W/O
5 = Skin cleansing gel
6 = After-shave hydrogel
7 = Anti-dandruff hair shampoo
8 = Anti-perspirant pump spray
9 = Skin lightening day care fluid O/W
10 = Skin barrier improving cream O/W
11 = Sun care lotion SPF 24 (UVA/UVB balance)

| Ingredients | 1 | 2 | 3 | 4 | 5 | 6 | 7 | 8 | 9 | 10 | 11 |
|---|---|---|---|---|---|---|---|---|---|---|---|
| Sulfetal LA | | | | | | | | | | | |
| Ammonium Lauryl Sulfate | | | | | 12 | | | | | | |
| SymCalmin ® | | | | | | | | | | | |
| Butylene Glycol, Pentylene Glycol, Hydroxyphenyl Propamidobenzoic Acid | 1 | | | | | | 0.1 | | | 0.1 | |
| SymClariol ® | | | | | | | | | | | |
| Decylene Glycol | | 0.5 | | | 1 | | | | 0.3 | | |
| SymDecanox HA | | | | | | | | | | | |
| Caprylic/Capric Triglyceride, Hydroxymethoxyphenyl Decanone | | | 2 | | | | | | | | |
| SymDeo ® B125 | | | | | | | | | | | |
| 2-Methyl 5-Cyclohexylpentanol | | | | | | | | 0.2 | | | |
| SymDeo ® MPP | | | | | | | | | | | |
| Dimethyl Phenyl 2-Butanol | | | | | | | | 0.5 | | | |
| Symdiol ® 68 | | | | | | | | | | | |
| 1.2-Hexanediol, Caprylyl Glycol | 1 | 0.5 | | | | | | | | | 0.3 |
| SymFinity ® 1298 | | | | | | | | | | | |
| Echinacea Purpurea Extract | | | | 0.05 | | | | | | | |
| SymGlucan ® | | | | | | | | | | | |
| Water (Aqua), Glycerin, β-glucan | 1 | | 5 | | | | | | | | 2 |
| SymHair ® Force 1631 | | | | | | | | | | | |
| Pentylene Glycol, Isochrysis galbana Extract | | | | | | | 2 | | | | |
| SymHelios ® 1031 | | | | | | | | | | | |
| Benzylidene Dimethoxydi-methylindanone | | 0.5 | | | | | | | | | |
| SymLift | | | | | | | | | | | |
| Water, trehalose, glycerin, pentylene glycol, β-glucan, hordeum vulgare seed extract, sodium hyaluronate, 1,2-Hexanediol, caprylyl glycol, sodium benzoate, maltodextrine | | 2 | | | | | | | | | |

TABLE 27-continued

Cosmetic formulations (amounts in parts by weight)
1 = Skin calming balm for sensitive skin
2 = Tinted anti-aging face balm, SPF 15
3 = After-sun moisturizing spray O/W
4 = Night cream W/O
5 = Skin cleansing gel
6 = After-shave hydrogel
7 = Anti-dandruff hair shampoo
8 = Anti-perspirant pump spray
9 = Skin lightening day care fluid O/W
10 = Skin barrier improving cream O/W
11 = Sun care lotion SPF 24 (UVA/UVB balance)

| Ingredients | 1 | 2 | 3 | 4 | 5 | 6 | 7 | 8 | 9 | 10 | 11 |
|---|---|---|---|---|---|---|---|---|---|---|---|
| SymMatrix | | | | | | | | | | | |
| Maltodextrin, Rubus Fruticosus (Blackberry) Leaf Extract | | 0.1 | 0.3 | | | | | | | | |
| SymMollient ® W/S | | | | | | | | | | | |
| Trideceth-9, PEG-5 Isononanoate, Water (Aqua) | | | | | 2 | | 2 | | | | |
| SymOcide ® C | | | | | | | | | | | |
| o-Cymen-5-ol | | | | | | 0.1 | | | | | |
| SymOcide ® PH | | | | | | | | | | | |
| Phenoxyethanol, Hydroxyacetophenone, Caprylyl Glycol, Water (Aqua) | | | | | | | 1.0 | | | | |
| SymOcide ® PS | | | | | | | | | | | |
| Phenoxyethanol, Decylene Glycol, 1,2-Hexanediol | | | | | | | | | | 0.8 | |
| SymOcide ® PT | | | | | | | | | | | |
| Phenoxyethanol, Tropolone | | | | 0.8 | | | | | | | |
| SymPeptide ® 225 | | | | | | | | | | | |
| Glycerin, Water (Aqua), Myristoyl Pentapeptide-11 | | | | 1 | | | | | | | |
| SymRelief ® 100 | | | | | | | | | | | |
| Bisabolol, Zingiber Officinale (Ginger) Root Extract | | | | | | 0.2 | | | | | |
| SymRelief S | | | | | | | | | | | |
| Bisabolol, Hydroxymethoxyphenyl Decanone | | | | | | | | | | 0.1 | |
| SymRepair ® 100 | | | | | | | | | | | |
| Hexyldecanol, Bisabolol, Cetylhydroxyproline Palmitamide, Stearic Acid, Brassica Campestris (Rapeseed) Sterols | | 1 | | 3 | | | | | | | |
| SymSave ® H | | | | | | | | | | | |
| Hydoxyacetophenone | | 0.5 | | | 0.8 | 0.5 | | | | | 0.5 |
| SymSol ® PF-3 | | | | | | | | | | | |
| Water (Aqua), Pentylene Glycol, Sodium Lauryl Sulfoacetate, Sodium Oleoyl Sarcosinate, Sodium Chloride, Disodium Sulfoacetate, | | | | | | 1.3 | | | | | |

TABLE 27-continued

| Cosmetic formulations (amounts in parts by weight)<br>1 = Skin calming balm for sensitive skin<br>2 = Tinted anti-aging face balm, SPF 15<br>3 = After-sun moisturizing spray O/W<br>4 = Night cream W/O<br>5 = Skin cleansing gel<br>6 = After-shave hydrogel<br>7 = Anti-dandruff hair shampoo<br>8 = Anti-perspirant pump spray<br>9 = Skin lightening day care fluid O/W<br>10 = Skin barrier improving cream O/W<br>11 = Sun care lotion SPF 24 (UVA/UVB balance) | | | | | | | | | | | |
|---|---|---|---|---|---|---|---|---|---|---|---|
| Ingredients | 1 | 2 | 3 | 4 | 5 | 6 | 7 | 8 | 9 | 10 | 11 |
| Sodium Oleate, Sodium Sulfate | | | | | | | | | | | |
| SymSitive ® 1609 | | | | | | | | | | | |
| Pentylene Glycol, 4-t-Butylcyclohexanol | | | 0.5 | | | | | | 0.5 | | |
| SymVital ® AgeRepair 3040 | | | | | | | | | | | |
| Zingiber Officinale (Ginger) Root Extract | | | 0.1 | | | | | | | | |
| SymWhite ® 377 | | | | | | | | | | | |
| Phenylethyl Resorcinol | | | | | | | | | 0.5 | | |
| Tamasterol ® | | | | | | | | | | | |
| Phytosterols | | | | | | | | | | 0.3 | |
| Tapioca Pure | | | | | | | | | | | |
| Tapioca Starch | | | | | | | | | | | 5 |
| Tegosoft ® PC 31 | | | | | | | | | | | |
| Polyglyceryl-3 Caprate | | | | | | | | | | 0.3 | |
| Triethanolamine | | | 0.3 | | | | | | | | |
| Vitamin A Palmitate | | | | | | | | | | | |
| Retinyl Palmitate | | | | 0.1 | | | | | | | |
| Vitamin E Acetate | | | | | | | | | | | |
| Tocopheryl Acetate | | 0.5 | | 0.2 | | | | | | 0.3 | 0.5 |
| Zetesol LA-2 | | | | | | | | | | | |
| Ammonium Laureth Sulfate | | | | | 26 | | | | | | |
| Water | | | | | | ad 100 | | | | | |

TABLE 28

| Gel dental cream | | | |
|---|---|---|---|
| Ingredients | I (%) | II (%) | III (%) |
| Sodium carboxymethylcellulose | 0.40 | 0.40 | 0.40 |
| Sorbitol 70% in water | 72.00 | 72.00 | 72.00 |
| Polyethylenglycol (PEG) 1500 | 3.00 | 3.00 | 3.00 |
| Sodium saccharinate | 0.07 | 0.07 | 0.07 |
| Sodium fluoride | 0.24 | 0.24 | 0.24 |
| p-Hydroxybenzoic acid (PHB) ethylester | 0.15 | 0.15 | |
| SymDiol 68 | | | 0.5 |
| SymSave H | | | 0.25 |
| Peppermint flavour | 1.00 | 1.00 | 1.00 |
| Oat kernel ethanol eluate fraction in glycerin/water standardized to 100-130 ppm Avns A to C in sum | 2.5 | | 0.5 |
| Naked oat kernel ethanol eluate fraction on maltodextrin standardized to ≥1000 ppm Avns in sum | | 0.3 | |
| Abrasive Silica | 11.00 | 11.00 | 11.00 |
| Thickening Silica | 6.00 | 6.00 | 6.00 |
| Sodium dodecylsulfate (SDS) | 1.40 | 1.40 | 1.40 |
| Distilled water | ad 100.00 | ad 100.00 | ad 100.00 |

TABLE 29

| Ready-to-use mouthwash with fluoride | | | |
|---|---|---|---|
| Ingredients | I (%) | II (%) | III (%) |
| Ethanol | 7.00 | 7.00 | |
| Glycerin | 12.00 | 12.00 | |
| Sodium fluoride | 0.05 | 0.05 | 0.18 |
| Pluronic F-127 ® (BASF, surface active substance) | 1.40 | 1.40 | |
| Sodium phosphate buffer pH 7.0 | 1.10 | 1.10 | |
| Sorbic acid | 0.20 | 0.20 | |
| Sodium saccharinate | 0.10 | 0.10 | 0.10 |
| Cinnamon/menthol flavour | 0.15 | 0.15 | 0.15 |
| Oat kernel ethanol eluate fraction in glycerin/water standardized to 100-130 ppm Avns A to C in sum | 1.00 | | 3.00 |
| Naked oat kernel ethanol eluate fraction on maltodextrin standardized to ≥1000 ppm Avns in sum | | 0.5 | |
| Colour | 0.01 | 0.01 | 0.01 |
| Sorbitol 70% | | | 10 |
| Cremophor RH455 | | | 1.8 |
| SymDiol 68 | | | 0.5 |

TABLE 29-continued

| Ready-to-use mouthwash with fluoride | | | |
|---|---|---|---|
| Ingredients | I (%) | II (%) | III (%) |
| SymSave H | | | 0.2 |
| Distilled water | ad 100.00 | ad 100.00 | ad 100.00 |

TABLE 30

| Chewing gums | I (%) | II (%) | III (%) |
|---|---|---|---|
| Chewing gum base | 21.00 | 21.00 | 21.00 |
| Glucose syrup | 16.50 | 16.50 | 16.50 |
| Glycerin | 0.50 | 0.50 | 0.50 |
| Powdered sugar | 60.45 | 60.36 | 60.27 |
| Spearmint aroma | 1.50 | 1.50 | 1.50 |
| Naked oat kernel ethanol eluate fraction on maltodextrin standardized to ≥1000 ppm Avns in sum | 0.05 | 0.5 | 0.2 |

TABLE 31

| Sugar-free chewing gums against bad breath | I (%) | II (%) | III (%) |
|---|---|---|---|
| Chewing gum base | 30.00 | 30.00 | 30.00 |
| Sorbitol, powder | 38.45 | 38.40 | 38.30 |
| Palatinite | 9.50 | 9.50 | 9.50 |
| Xylitol | 2.00 | 2.00 | 2.00 |
| Mannitol | 3.00 | 3.00 | 3.00 |
| Aspartame | 0.10 | 0.10 | 0.10 |
| Acesulfame K | 0.10 | 0.10 | 0.10 |
| Emulgum/emulsifier | 0.30 | 0.30 | 0.30 |
| Sorbitol 70%, in water | 14.00 | 14.00 | 14.00 |
| Glycerin | — | 0.50 | 0.75 |
| Cinnamon/menthol aroma | 1.50 | 1.50 | 1.50 |
| Oat kernel ethanol eluate fraction in glycerin/water standardized to 100-130 ppm Avns A to C in sum | 2.00 | 1.00 | 0.50 |

TABLE 32

| Fruit gums | I (%) | II (%) |
|---|---|---|
| Water | to 100 | to 100 |
| Saccharose | 34.50 | 34.50 |
| Glucose syrup, DE 40 | 31.89 | 31.89 |
| Iso Syrup C* Tru Sweet 01750 (Cerestar GmbH) | 1.50 | 2.10 |
| Gelatine 240 Bloom | 8.20 | 9.40 |
| Colorant | 0.01 | 0.01 |
| Citric acid | 0.10 | 0.10 |
| Citrus flavour | 0.20 | — |
| Cherry flavour | — | 0.1 |
| Oat kernel ethanol eluate fraction on maltodextrin standardized to ≥150 ppm Avns in sum | | 1.00 |
| Naked oat kernel ethanol eluate fraction on maltodextrin standardized to ≥1000 ppm Avns in sum | 0.25 | |

TABLE 33

| Yoghurt with low fat content | I (%) | II (%) | III (%) |
|---|---|---|---|
| Sucrose | 110 | 8 | — |
| Sucralose | — | 0.02 | 0.2 |
| Saccharin | — | | 0.3 |
| Sour cherry extract | 0.2 | 0.1 | 0.2 |
| Cherry flavor | — | 0.01 | — |
| Oat kernel ethanol eluate fraction on maltodextrin standardized to ≥150 ppm Avns insum | — | 1.00 | — |
| Naked oat kernel ethanol eluate fraction on maltodextrin standardized to ≥1000 ppm Avns in sum | 0.25 | — | 1.0 |
| Yoghurt, 0.1% fat | ad 100 | ad 100 | ad 100 |

The invention claimed is:

1. A composition or oat extract comprising
0.5 to 7.0 wt % of total avenanthramides,
1.0 to 3.3 wt % of β-glucan,
≤1.0 wt % of salts,
0.5 to 1.5 wt % of total free amino acids,
>0.05 wt % of phenylalanine, and
>0.25 wt % of tryptophan,
based on the dry weight of the composition or the dry weight of the oat extract.

2. The composition or oat extract according to claim 1, wherein the weight ratio of the total avenanthramides to the β-glucan is in a range of 1:3 to 3:1.

3. The composition or oat extract according to claim 1, wherein an oat source of the oat extract is milled or non-milled grains of the species *Avena sativa* or *Avena nuda* or oat straw.

4. The composition or oat extract according to claim 1, wherein the total avenanthramides comprise avenanthramides selected from the group of avenanthramide A, B, C, G, H, K, L, and R.

5. The composition or oat extract according to claim 1, wherein the composition or oat extract comprises:
1.0 to 6.5 wt % of total avenanthramides;
1.5 to 2.8 wt % of β-glucan;
≤0.5 wt. % of salts;
0.6 to 0.9 wt % of total free amino acids;
>0.075 wt % of phenylalanine; and
>0.3 wt % of tryptophan;
based on the dry weight of the composition or the dry weight of the oat extract.

6. The composition or oat extract according to claim 1, wherein the composition or oat extract has a radical-scavenging activity of at least 70% as determined by ABTS assay.

7. The composition or oat extract according to claim 1, further comprising 1,2-pentanediol.

8. A food, food supplement, cosmetic, pharmaceutical, or veterinary preparation comprising the composition or oat extract of claim 1.

9. The food, food supplement, cosmetic, pharmaceutical, or veterinary preparation, of claim 8 comprising the composition or the oat extract in an amount of 0.0001 to 10 wt %, based on the total weight of the food, food supplement, cosmetic, pharmaceutical, or veterinary preparation.

* * * * *